United States Patent
Isaacs et al.

(10) Patent No.: US 8,299,269 B2
(45) Date of Patent: Oct. 30, 2012

(54) NOR-SECO-BIS-NOR-SECO, TRIS-NOR-SECO, AND HIGHER NOR-SECO-CUCURBIT[N]URIL COMPOUNDS

(75) Inventors: Lyle David Isaacs, Beltsville, MD (US); Wei-Hao Huang, College Park, MD (US)

(73) Assignee: University of Maryland, College Park, MD (US)

( * ) Notice: Subject to any disclaimer, the term of this patent is extended or adjusted under 35 U.S.C. 154(b) by 848 days.

(21) Appl. No.: 12/224,504

(22) PCT Filed: Oct. 20, 2006

(86) PCT No.: PCT/US2006/041116
§ 371 (c)(1),
(2), (4) Date: Aug. 28, 2008

(87) PCT Pub. No.: WO2007/106144
PCT Pub. Date: Sep. 20, 2007

(65) Prior Publication Data
US 2009/0072191 A1    Mar. 19, 2009

Related U.S. Application Data

(60) Provisional application No. 60/743,369, filed on Feb. 28, 2006.

(51) Int. Cl.
C07D 257/10    (2006.01)
C07D 235/00    (2006.01)
(52) U.S. Cl. ..................... 548/301.7; 540/472
(58) Field of Classification Search .......... 540/472; 548/301.7
See application file for complete search history.

(56) References Cited

U.S. PATENT DOCUMENTS
2005/0080068 A1 *   4/2005   Isaacs et al. ............... 514/183

OTHER PUBLICATIONS

Day et al. "Controlling Factors in the Synthesis of Cucurbituril and Its Homologues" J. Org. Chem. 2001, 8094-8100.*
Lee et al. "Cucurbituril Homologues and Derivatives: New Opportunities in Supramolecular Chemistry" Acc. Chem. Res. 2003, 621-630.*

* cited by examiner

*Primary Examiner* — Joseph Kosack
(74) *Attorney, Agent, or Firm* — William E. Beaumont

(57) ABSTRACT

Nor-seco-type cucurbit[n]uril compounds and methylene bridged glycoluril oligomers are produced by reacting glycoluril and formaldehyde in strong organic or mineral acid at a temperature adequate to condense the reactants. These compounds are characterized by lacking —$CH_2$— groups rendering their internal cavities more open and, for example, more responsive to guest compounds.

14 Claims, 29 Drawing Sheets

NOR-SECO-BIS-NOR-SECO, TRIS-NOR-SECO, AND HIGHER NOR-SECO-CUCURBIT[N]URIL COMPOUNDS

CROSS REFERENCE TO RELATED CASES

This application claims priority to Provisional Application Ser. No. 60/743,369, filed Feb. 28, 2006.

The work leading up to the present invention was funded, at least in part, by the National Science Foundation (CHE-0615049). As such, the federal government may have certain rights in the present invention pursuant to 35 U.S.C. 203 et seq.

BACKGROUND OF THE INVENTION

1. Field of the Invention

The present invention relates to nor-seco-, bis-nor-seco- as well as tris-nor-seco- and even higher nor-seco-cucurbit[n]uril compounds, including racemates and enantiomers thereof, and methods of making and using the same.

2. Description of the Background

In 1905, Behrend and co-workers reported the condensation of glycoluril (1 eq.) and formaldehyde (2 eq.) under aqueous acidic conditions (HCl, 100° C.). The product of this reaction—known in the literature as Behrend's polymer—was insoluble in nearly all solvents, but could be recrystallized from hot sulfuric acid from which a well-defined substance was obtained. In 1981, Mock and co-workers reported the structural characterization of this substance as cucurbituril (CB[6]). In recent years, various cucurbit[n]uril, i.e., CB[n], compounds have been prepared, isolated and characterized as shown below in Scheme 1.

Scheme 1. Synthesis of cucurbit[6]uril and cucurbit[n]uril.

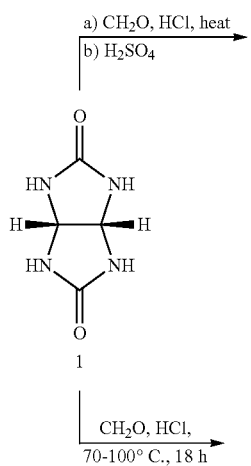

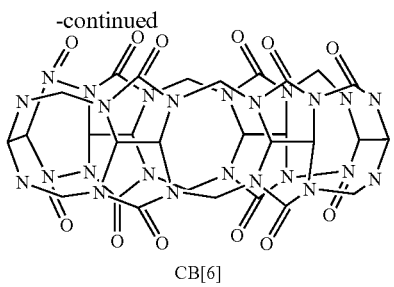

CB[6]

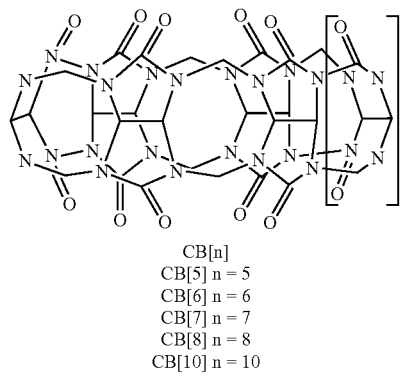

CB[n]
CB[5] n = 5
CB[6] n = 6
CB[7] n = 7
CB[8] n = 8
CB[10] n = 10

These CB[n] compounds, with their large cavity volumes, function as host compounds which bind a wide range of chemically and biologically important guest molecules. These CB[n] compounds may be described as "extroverted" inasmuch as the H-atoms convex on the face of the glycoluril rings point outward therefrom. CB[n] compounds participate in a variety of interesting applications as diverse as fluorophore stabilization, chemical sensing, supramolecular vesicles, supramolecular dendrimers, molecular machines and complex self-sorting systems. For a review of cucurbit[n]uril homologues and derivatives, see Lee, W. et al. Acc. Chem. Res. 2003, 36, 621-630, and Lagona, J. et al. Angew. Chem. Int. Ed. 2005, 44, 4844-4870.

Subsequent to Mock's pioneering work, the groups of Kim and Day independently performed the condensation of glycoluril (1 eq.) and formaldehyde (2 eq.) under milder conditions (e.g. 70-100° C.) and were able to isolate the macrocycles containing 5, 7, and 8 glycoluril rings (CB[5], CB[7], and CB[8]), respectively, by fractional recrystallization procedures (Kim, J. et al. JACS, 2000, 122, 540-541 and Day, A. I. et al. J. Org. Chem., 2001, 66, 8094-8100). The Day group also reported the isolation of the cucurbit[10]uril as its inclusion complex with cucurbit[5]uril (CB[5]@CB[10]), see Day, A. I. et al. Angew. Chem. Int. Ed., 2002, 41, 275-277. The Isaacs group subsequently reported a method to remove the CB[5] from the CB[5]@CB[10] complex and thus have isolated CB[10] in uncomplexed form (Liu, S. et al. JACS, 2005, 127, 16798-16799).

More recently, (bis)phthalhydrazides have been used as glycoluril surrogates in the formation of cucurbit[n]uril analogs. This approach allows for a tailor-made synthesis of cucurbit[n]uril analogs, having phthalhydrazide units in a macrocycle wall thereof, with control over the size, shape and chemical functionality of the formed cucurbit[n]urils to a level not previously possible. See U.S. Ser. No. 10/933,538. These analogs are described as extroverted cucurbit[n]urils inasmuch as substituents on the convex face of the glycoluril protrude outwards from the internal molecular cavity.

Even more recently, inverted CB[n] compounds were discovered. See Isaacs, L. et al., JACS, 2005, 127, 18000-18001. These compounds are characterized by having at least one pair of hydrogen atoms protruding into the internal cavity of the cucurbit[n]uril compounds and, as such, are diastereomers of the extroverted CB[n] compounds. Inverted cucurbit[n]urils have one or more "inverted" glycoluril rings where at least two H-atoms or other substituents on the convex face of the glycoluril rings point into the cavity of the macrocycle.

Inverted cucurbit[n]urils or i-CB[n] compounds have the following type of structure, wherein the protruding hydrogen atoms are conspicuous:

The recognition properties of these inverted macrocycles are modulated in a useful way, i.e., enhanced kinetics and selectivity for aromatic guests like p-xylylene diamine by the structural change resulting therefrom. We determined that the use of p-xylylene diamine as probe of the crude CB[n] forming reaction mixture is particularly powerful since each cucurbit[n]uril or related compound gives a distinct resonance in the 6-7 ppm region of the $^1$H NMR spectrum. This allows for the facile identification of individual CB[n]-type compounds in crude reaction mixtures containing many different CB[n]-type compounds.

However, a need exists for nor-seco-type cucurbit[n]urils as these compounds lack —$CH_2$— groups rendering their internal cavities more open and, thus, more responsive, for example, to guest compounds intended for use in the cavities.

SUMMARY OF THE INVENTION

It is an object of the present invention to provide nor-seco-, bis-nor-seco- as well as tris-nor-seco- and even higher nor-seco-cucurbit[n]uril compounds, which are structurally distinct from either extroverted or inverted cucurbit[n]uril compounds and analogs.

It is, moreover, an object of this invention to afford racemates and enantiomers of these compounds.

It is also an object of the present invention to provide a method of making the various nor-seco-type cucurbit[n]uril compounds.

It is moreover, an object of the present invention to provide methylene-bridged oligomers of glycoluril for making the nor-seco-type and higher nor-seco-cucurbit[n]uril compounds of the present invention.

Additionally, it is an object of the present invention to provide a method of making the nor-seco-type CB[n] compounds of the present invention, as well as a method of purifying these compounds once formed.

The above objects and others which are described hereinbelow are provided by a nor-seco-, bis-nor-seco-, tris-nor-seco- or higher nor-seco-cucurbit[n]uril compound, including racemates and enantiomers thereof.

DETAILED DESCRIPTION OF THE PREFERRED EMBODIMENTS

Figure 1:
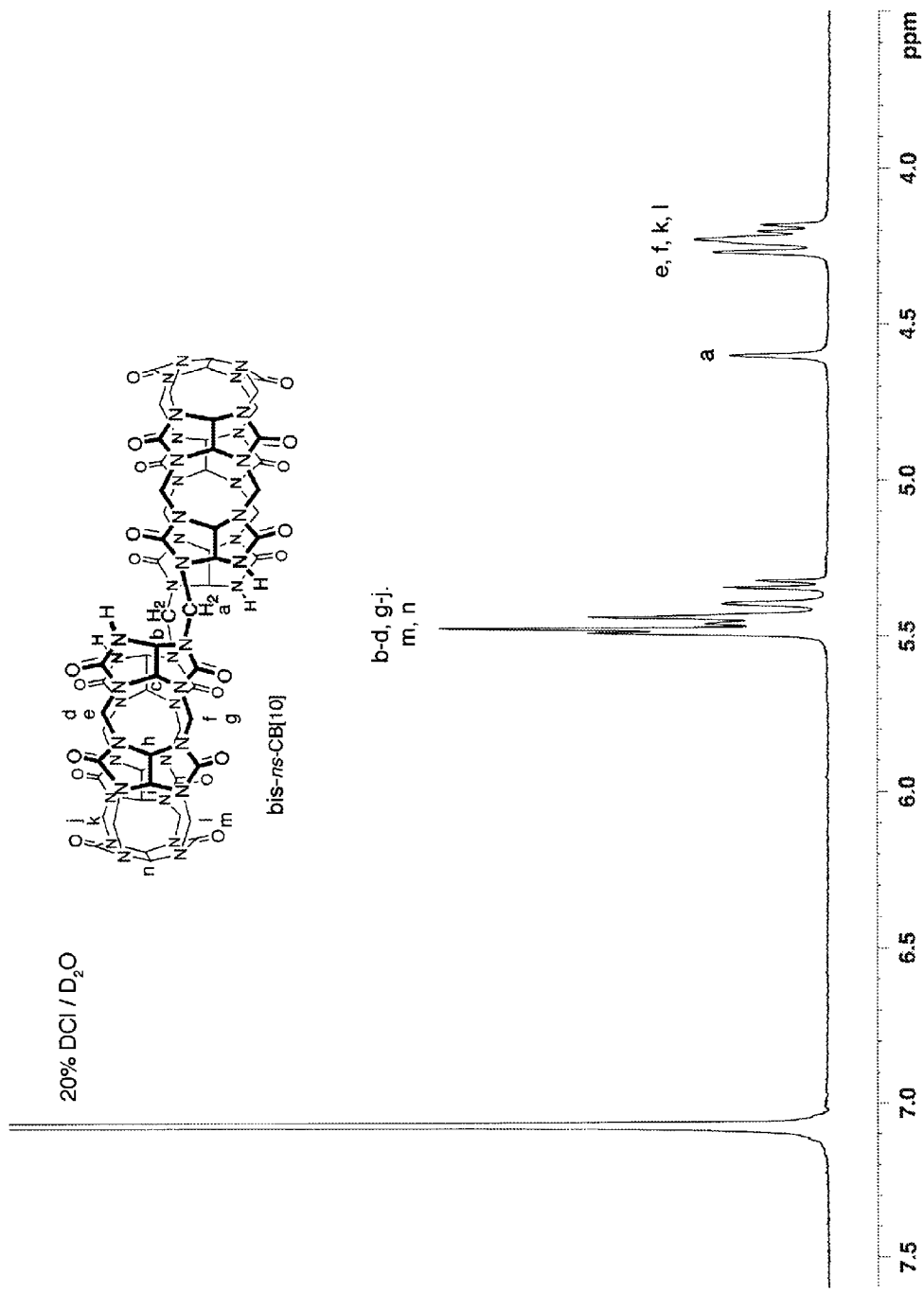
FIG. 1 is a $^1$H NMR spectrum for bis-ns-CB[10] in 20% DCl/$D_2O$ (400 MHz, RT).

The present invention provides new types of cucurbit[n] uril compounds, and, in particular, nor-seco-cucurbit[n]uril, bis-nor-seco cucurbit[n]urils, tris-nor-seco cucurbit[n]urils and even higher nor-seco-cucurbit[n]urils. As used herein, the abbreviation "ns" is used to mean nor-seco, and bis-ns and tris-ns to mean bis-nor-seco- and tris-nor-seco, respectively.

The present invention also provides chiral nor-seco-, bis-nor-seco-, tris-nor-seco- and higher nor-seco-cucurbit[n]uril compounds. These chiral compounds may be resolved to afford each of their enantiomeric components.

Additionally, the present invention also provides methylene bridged oligomers of glycoluril which are condensed to prepare various nor-seco-cucurbit[n]uril compounds.

The present invention is based, at least in part, upon the recognition that different ratios of glycoluril:formaldehyde afford oligomers of different length. Generally, the ratios of glycoluril:formaldehyde used are preferably from about 1:1 to less than about 1:2. However, it is acceptable if ratios as low as 1:0.5 be used. Generally, ratios of "less than about 1:2" means ratios of up to not more than about 1:1.9, and preferably up to not more than about 1:1.8. It is even more preferable if the ratio is up to not more than about 1:1.7. For example, in Scheme 2, dimer 6 is composed of 2 equivalents of glycoluril and 2 equivalents of formaldehyde for a 2:2 (equivalently 1:1 ratio. Similarly, trimer 7 is composed of 3 equivalents of glycoluril and 4 equivalents of formaldehyde for a 3:4 (1:1. 33) ratio. Tetramer, pentamer, hexamer, heptamer, and n-mer have idealized glycoluril:formaldehyde ratios of 4:6 (1:1.5), 5:8 (1:1.6), 6:10 (1:1.66), 7:12 (1:1.71), and n:2n-2), respectively. For the preparation of a specific oligomer, a calculated ratio of glycoluril:formaldehyde is used. This discovery, in combination with the use of p-xylylene diamine as a probe of the crude reaction mixtures, lead to the discovery of the nor-seco-type CB[n] family of macrocycles, which is the subject of the present invention.

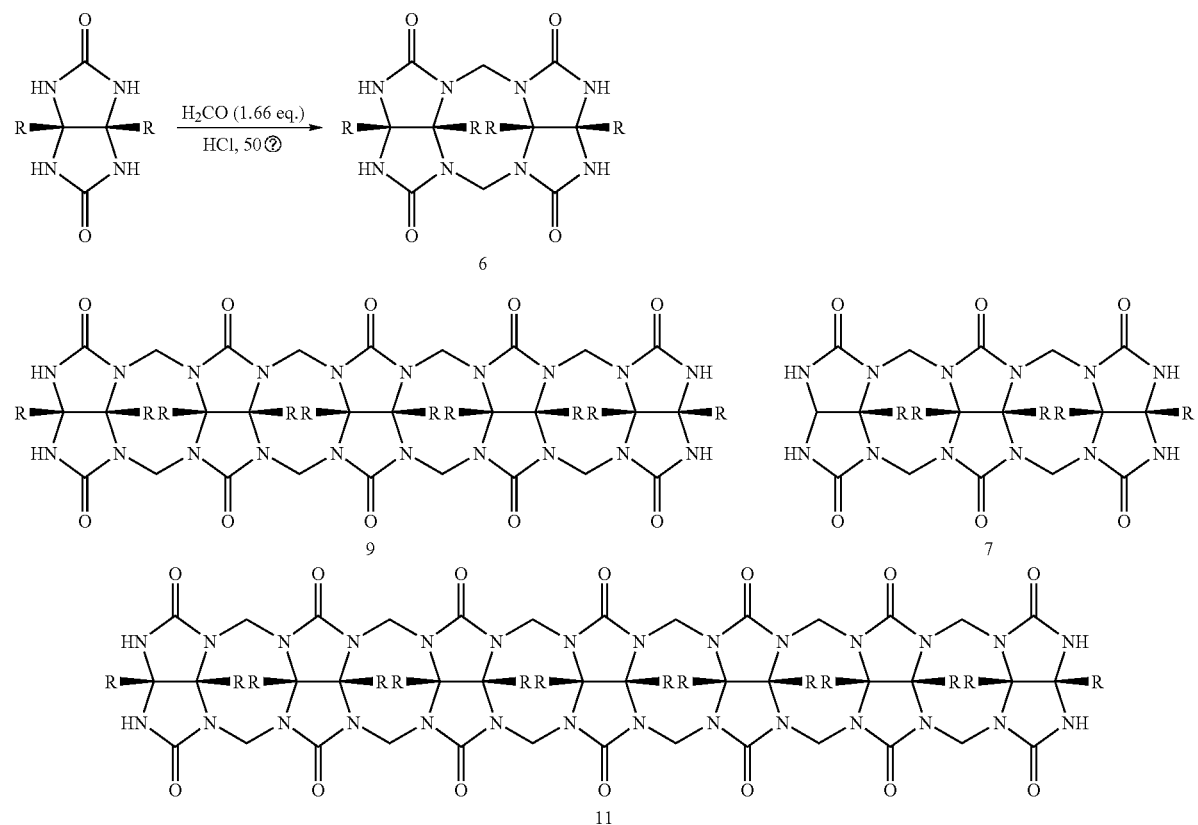

Scheme 2. Synthesis of glycoluril oligomers.

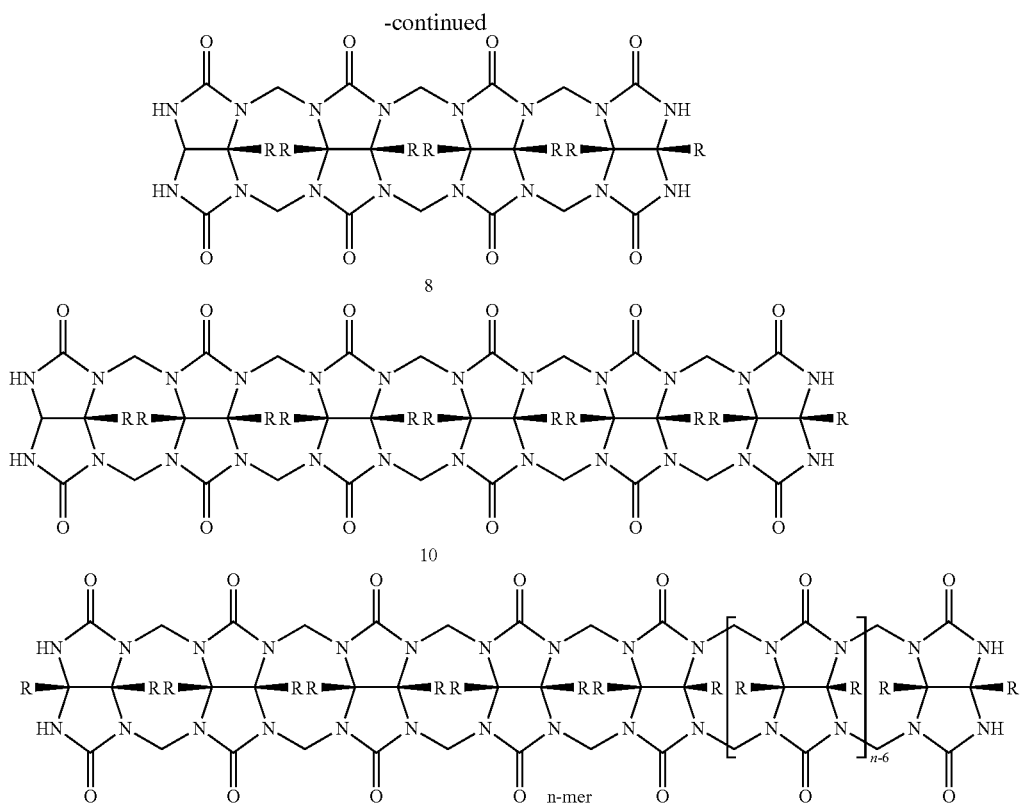

In Scheme 2, each R may be hydrogen or a substituent group, such as lower alkyl, aryl, heteroaryl, alkoxy, or carboxylic acid derivatives, such as esters, amides, and imides.

The present invention provides, in part, nor-seco-, bis-nor-seco-, tris-nor-seco- or even higher nor-seco-cucurbit[n]uril compounds. Generally, the nor-seco (or ns-) or bis-nor-seco (or bis ns) CB[n] compounds of the present invention have formulae as exemplified below:

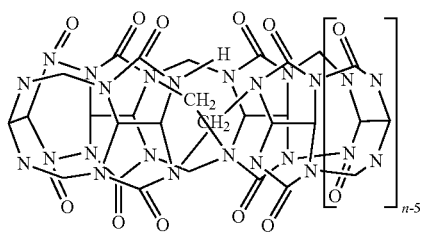

Type 5 compounds
(±)-Bis-Nor-seco-CB-5) (n = 0)
(±)-Bis-Nor-seco-CB-6) (n = 1)
(±)-Bis-Nor-seco-CB-7) (n = 2)
(±)-Bis-Nor-seco-CB-8) (n = 3)
(±)-Bis-Nor-seco-CB-10) (n = 5)

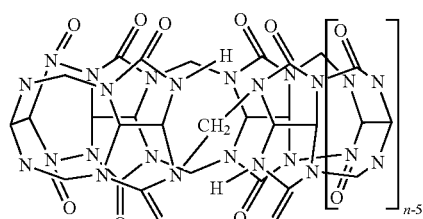

Type 7 compounds
(±)-Nor-seco-CB-5) (n = 0)
(±)-Nor-seco-CB-6) (n = 1)
(±)-Nor-seco-CB-7) (n = 2)
(±)-Nor-seco-CB-8) (n = 3)
(±)-Nor-seco-CB-10) (n = 5)

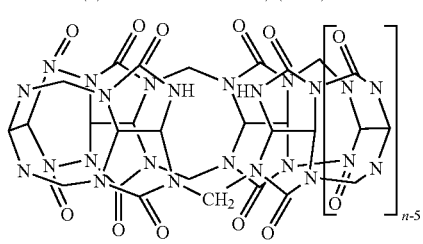

Type 3 compounds
Nor-seco-CB[5] (n = 0)
Nor-seco-CB[6] (n = 1)
Nor-seco-CB[7] (n = 2)
Nor-seco-CB[8] (n = 3)
Nor-seco-CB[10] (n = 5)

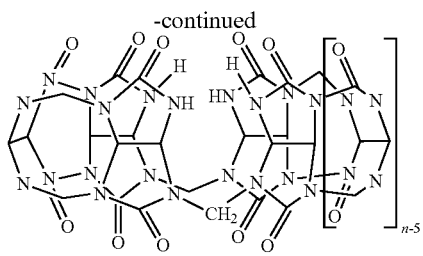

Type 1 Compounds
Bis-Nor-seco-CB[5] (n = 0)
Bis-Nor-seco-CB[6] (n = 1)
Bis-Nor-seco-CB[7] (n = 2)
Bis-Nor-seco-CB[8] (n = 3)
Bis-Nor-seco-CB[10] (n = 5)

The above compound structures are merely a few examples of the nor-seco-type cucurbit[n]uril-type compounds which are the subject of the present invention. For example, as used herein, the (±) nor-seco-compounds in the upper left column may be described as "Type 7" linkage compounds. The (±)-bis-nor-seco compounds in the upper right column may be described as "Type 5" linkage compounds. The nor-seco-compounds in the lower left column may be described as "Type 3" linkage compounds, and the bis-nor-seco compounds in the lower right column may be described as "Type 1" compounds. Not shown in the above nor-seco- and bis-nor-seco-structures, but explicitly contemplated as being within the scope of the present invention, are tris-nor-seco compounds, (±)-tris-nor-seco compounds and higher nor-seco and higher (±)-nor-seco-compounds such as tetrakis-nor-seco compounds, (±)-tetrakis-nor-seco compounds and pentakis-nor-seco- and (±)-pentakis-nor-seco compounds.

Generally, in the above four nor-seco-type CB[n] formulae (e.g. CB[n]), "n" may have a value of 3 to 40. All values included are specifically contemplated, i.e., for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40.

Thus, in accordance with the present invention, a desired nor-seco-type CB[n] compound may be prepared by varying the ratio of glycoluril and formaldehyde reactants. For example, heating a mixture of glycoluril and formaldehyde (1:1-1:1.9) in a strong organic acid or mineral acid (HCl, methanesulfonic acid, sulfuric acid, p-toluenesulfonic acid, phosphoric acid, HBr, trifluoroacetic acid, HI, for example) affords a mixture of glycoluril oligomers ((e.g. 6-11 and n-mer, Scheme 2) that can be separated by several different methods, such as fractional recrystallization, gel permeation chromatography, ion exchange chromatography, or silica gel chromatography.

Generally, the compound that can form methylene bridges between glycoluril units is most preferably formaldehyde, paraformaldehyde, trioxane, hexamethylenetetramine or one or more precursors for formaldehyde. For convenience, the invention will hereinafter be described with reference to the case where formaldehyde is used. Thus, in accordance with the present invention; formaldehyde itself may be used as well as any compound which generates formaldehyde in situ.

In addition to the oligomeric compounds described above, we have also discovered that the crude reaction mixture contains new macrocyclic members of the cucurbit[n]uril family which lack one, two or more $CH_2$ groups. The prefix "nor-seco" is used in IUPAC nomenclature to indicate the removal of $CH_2$ groups from a parent compound. Hence, we refer to, and describe herein, these new compounds as nor-seco-cucurbiturils (ns-CB[n]). The designation of bis-nor-seco indicates the removal of two $CH_2$ groups.

Generally, several factors determine the size of the nor-seco-type CB[n] compounds obtained. First, as noted above, the glycoluril:formaldehyde ratio is important. In general, as the ratio of glycoluril formaldehyde increases from about 1:1 to up to about 1:2, nor-seco-type CB[n] of larger n sizes are obtained. Second, the choice of solvent is important. We have found, for example, that HCl (aq) affords more ns-CB[10] than does $MeSO_3H$. The presence of water appears to be important such that with HCl (aq), a relatively large amount of water is present and equilibrium is facile. In contrast, in $MeSO_3H$, little water is present, and kinetics becomes more important. Third, the acidic strength influences the course of reaction as does also reaction time and temperature. Generally, a reaction temperature from room temperature or about 20° C. to about 120° C. is used. Fourth, the presence or absence of templating compounds and ions may also influence the reaction and, hence, formation of product.

Additionally, some templates may cause precipitation of a single nor-seco-type CB[n] compound which advantageously leads to straightforward isolation by filtration. Related and known procedures are and have been used for the industrial scale purification of various cyclodextrins.

In general, when a slower rate of reaction is obtained, it is easier to stop the reaction at the appropriate time to obtain and isolate a given nor-seco-type CB[n] compound or oligomer.

Generally, for the maximized production of a given nor-seco-type CB[n] compound, selections of glycoluril:formaldehyde ratio, temperature, and concentration of glycoluril and acid are made. Precipitated products may be separated by centrifugation, for example from the mother liquor, and then washed one or more times. For example, for bis-ns-CB[10], the precipitate is first washed by HCl:$H_2O$, and then by aqueous $Na_2SO_4$. The product is then preferably washed a third time with $H_2O$.

For bis-ns-CB[10], it is preferred that the first wash HCl:$H_2O$ be approximately (1:1, v/v) and that the second wash aqueous $Na_2SO_4$ be approximately 0.2 M.

However, some nor-seco-type CB[n] products remain in solution in the reaction mixture and are not isolable as a precipitate. For such nor-seco-type CB[n] product compounds, a different procedure is used to recover product. Specifically, the crude reaction mixture is generally poured into a polar, organic solvent, such as MeOH or acetone, to cause precipitation. The precipitate is then filtered and dried to afford a crude solid. The crude solid may then be processed in several different ways using well-known procedures including, for example, recrystallization (from different acids), gel permeation chromatography, washing with various salt or guest solutions, or Dowex ion exchange chromatography. We have obtained good results using Dowex ion exchange chromatography routinely. See the exemplary preparatory procedure for Dowex ion exchange chromatography in the Experimental Detail section.

Thus, the present invention provides, in part, various oligomer compounds as exemplified above as compounds 7-11 and n-mer in Scheme 2. We have also isolated compound 6 by these procedures. Certain compounds having the general formula of Compound 6 were previously reported by Day. See Zhao et al., Chin. Sci. Bull., 2004, 49, 1111-1116. See WO 2005/090351 A1.

Further, the present oligomer compounds may then be condensed to yield various types of nor-seco-type CB[n] compounds as exemplified below in Scheme 3.

The exemplary compounds shown in Scheme 3 illustrate the types of linkages formed as well as the various types of compounds that can be prepared by the condensation of glycoluril oligomers.

These compounds and their inter-relation are depicted below in Scheme 3.

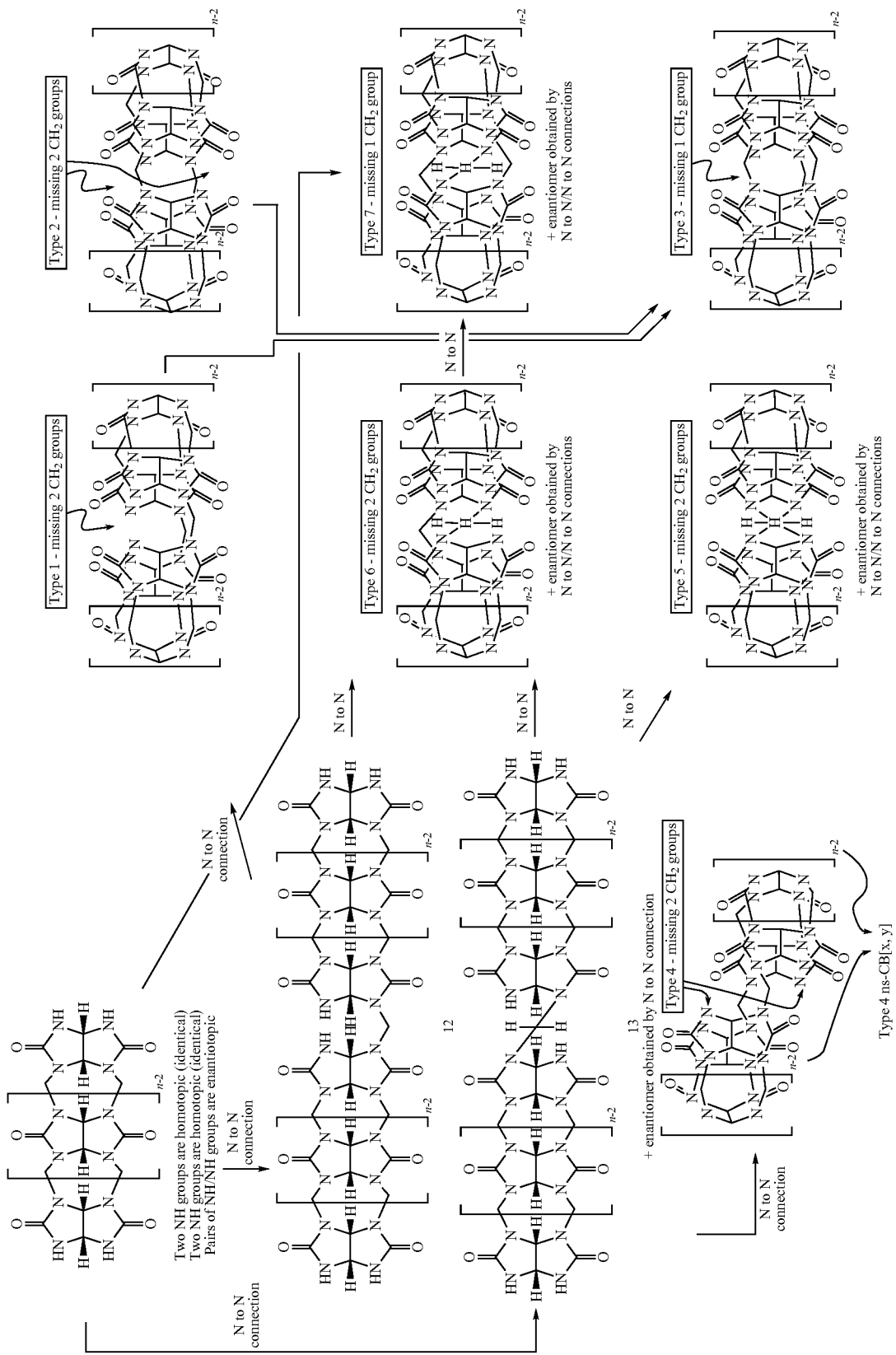
Scheme 3

Generally, a glycoluril or glycoluril oligomer (e.g. 6-11, n-mer) is mixed with formaldehyde in a 1:1 to up to 1:2 ratio in an appropriate strong organic or mineral acid (e.g. HCl, MeSO₃H, etc.) and heated in the temperature range of from about room temperature to about 120° C., and preferably in the temperature range about 40 to about 60° C., such as at 50° C., for example. The reaction mixture is monitored using p-xylylene diamine as a probe and the reaction is stopped when the desired nor-seco-type CB[n] compound has reached its maximum abundance. The reaction mixture is then poured into MeOH to precipitate the crude mixture of nor-seco-type CB[n] and the solid is washed with MeOH/acetone and dried overnight under high vacuum. The obtained solid is chromatographed on Dowex ion exchange resin eluting with formic acid: HCl (aq) (1:1), with a gradient of HCl concentration of from 0 to 2 M.

By way of further explanation, as an example glycoluril may be condensed with formaldehyde in a 1:1.8 ratio, i.e., 10 units of glycoluril and 18 units of formaldehyde to prepare bis-ns-CB [10].

Alternatively, and advantageously, bis-ns-CB[10] may also be prepared by condensing pentamer (compound 9 in Scheme 2) with formaldehyde in a 2:2 ratio (1:1). The calculated 1:1 ratio affords a larger dynamic range of ratios to optimize the yield of the desired bis-ns-CB[10], i.e., more flexibility as well as control of the reaction.

It is important in preparing the various nor-seco-type CB[n] compounds to target them using building blocks of glycoluril oligomers/formaldehyde in a ratio of up to 1:2, and preferably less. We have observed that with glycoluril oligomer/formaldehyde ratio of very close to 1:2, i.e., 1:1.98, that substantial amounts of extroverted cucurbit[n]urils are formed.

Therefore, in order to target decakis-ns-CB[40], for example, 40 molecules of glycoluril and 70 molecules of formaldehyde (1:1.75) could be condensed, or 10 molecules of tetramer (compound 8 in Scheme 2) and 10 molecules of formaldehyde (1:1) could be condensed to obtain a better yield of decakis-ns-CB[40].

Generally, it is preferable for the preparation of nor-seco-type CB[n] compounds having large n values, to have a higher number of missing —CH₂— groups, such as tetrakis- or higher in order to minimize strain.

As another example, in order to target tetrakis-ns-CB[20], 20 equivalents of glycoluril and 36 equivalents of formaldehyde (1:1.8) may be condensed, or 4 equivalents of the same pentamer as above and 4 equivalents of formaldehyde (1:1) to form tetrakis-ns-CB[20]. In view of the reactant ratio in the latter, the latter is preferred.

Generally, as noted above, it is preferred that a glycoluril/formaldehyde ratio be used of not more than (1:1.8), and more preferably not more than (1:1.7).

Thus, with the present disclosure, one skilled in the art may select a particular ratio of glycoluril or glycoluril/oligomer formaldehyde reactants to target a specific nor-seco-type CB[n] compound. For a given target compound, the required ratio of reactants will determine whether glycoluril or a glycoluril oligomer will be reacted with formaldehyde.

Further, as noted from the previous formulae of exemplary Type 1, Type 3, Type 5 and Type 7 compounds, nor-seco- and bis-nor-seco-cucurbit[n]uril compounds which are chiral (e.g. existing in enantiomeric (+)- and (−)-forms) may be prepared. These formulae are only exemplary, and the present specification clearly and explicitly contemplates the preparation of tris-nor-seco- and higher-nor-seco-cucurbit[n]uril compounds, both chiral and achiral.

The chiral nor-seco-, bis-nor-seco-, tris-nor-seco- and higher nor-seco-cucurbit[n]uril of the present invention may be resolved into their respective enantiomers in several ways, all of which rely on use known methodologies. For example, the racemic mixture may be chromatographed on Dowex using formic acid:aq. HCl 1:1 that contains an enantiomerically pure amine as mobile phase additive. Diastereomers are therefore formed in the mobile phase and those diastereomers separate on the column. Recovery of the enantiomerically pure nor-seco-type CB[n] occurs by the addition of base or acetic anhydride followed by washing with organic solvents. Alternatively, the racemic mixture can be chromatographed on a variety of chiral stationary phases; specific mention is made of the cyclodextrin phases offered by Astec and organic chiral phases offered by Regis Technologies. A third alternative method is based on the classic resolution techniques involving chiral alkaloids. Such enantiomerically pure alkaloids form diastereomers when they bind to racemic nor-seco-type CB[n]. Accordingly, the diastereomers can generally be separated by crystallization of the less soluble diastereomer while the more soluble diastereomer remain in solution. Simple filtration gives the pure diastereomer. The enantiomerically pure nor-seco-type CB[n] is then generated by the addition of base or acetic anhydride followed by washing with organic solvents.

The above procedures may be used to resolve any of the racemates of the present invention into their respective enantiomers. Thus, the present invention explicitly contemplates isolated enantiomers of all chiral nor-seco type compounds described herein. By "nor-seco-type compounds" is meant all ns-type compounds described herein i.e., all nor-seco-, bis-nor-seco-, tris-nor-seco- and higher nor-seco-type CB[n] compounds.

The present invention will now be further described by certain Examples which are provided solely for purposes of illustration and which are not intended to be limitative.

In some of the following Examples, reference is made to certain compounds identified below by number, which function as guest compounds to facilitate structural elucidation by NMR. To avoid confusion with oligomer numbers, these guest compounds are referred to subsequently in the specification by a "guest #" designation, i.e., "guest #10."

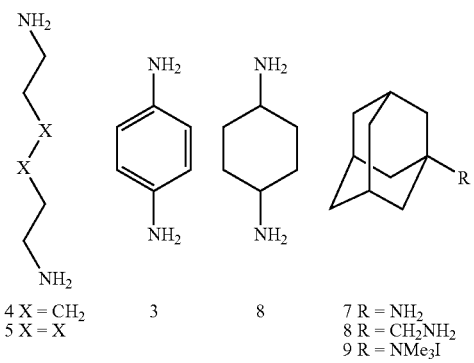

4 X = CH₂
5 X = X

3

8

7 R = NH₂
8 R = CH₂NH₂
9 R = NMe₃I

-continued

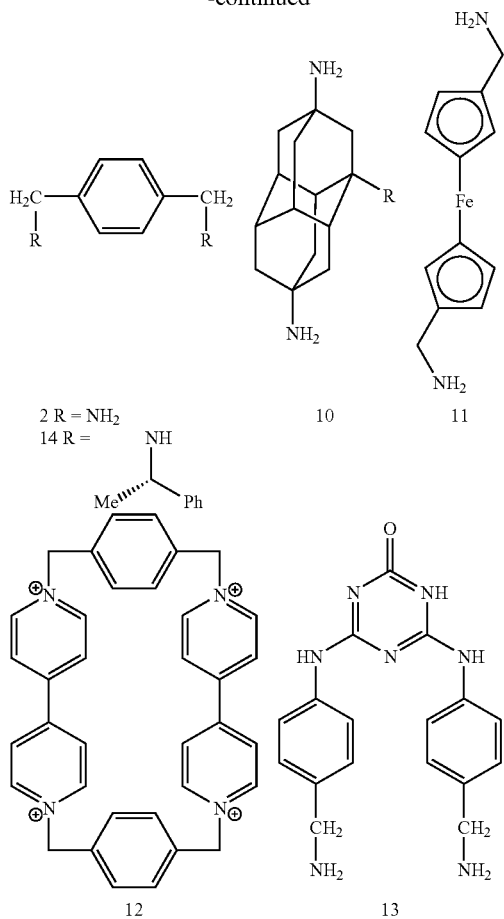

Exemplary Guest Compounds and their Respective Guest Number Designations

Example 1

Synthesis Examples for bis-ns-CB[10]

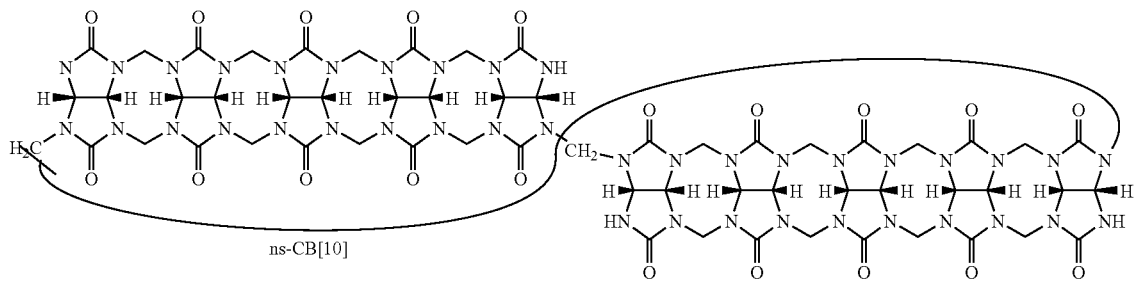

A mixture of glycoluril (1.42 g, 9.99 mmol), paraformaldehyde (0.50 g, 16.69 mmol), and conc. HCl (4 mL) was heated at 50° C. for 3 days. The resulting precipitate was separated by centrifugation to yield a crude solid (300 mg). The crude solid was washed with HCl:H$_2$O (1:1, v/v), 0.2M Na$_2$SO4, and finally H$_2$O to yield bis-ns-CB[10] (238 mg, 0.145 mmol, 15%) as a white solid. M.p>300° C. IR (KBr, cm$^{-1}$): 3280 m, 3219 m, 1699 s, 1461 s, 1323 s, 1219 s, 1190 s, 962 s, 797 s, 757 s. $^1$H NMR (400 MHz, 20% DCl/D$_2$O): 5.47 (m, 28H), 5.40 (s, 4H), 5.33 (d, J=4.0, 4H), 4.60 (s, 4H), 4.60 (s, 4H), 4.20 (m, 16H). See FIG. 1. $^{13}$C NMR (100 MHz, 20% DCl/D$_2$O, ext. dioxane reference): 154.0, 151.6, 151.0, 150.8, 15.0.7, 66.6, 64.9, 57.4, 46.3, 46.0, 45.8, 41.3 (only 12 of the 16 expected resonances were observed). MS (ES): m/z 819 (100, [M+2H]$^{2+}$, m/z spacing=0.5 confirmed for molecular ion). HR-MS (ES) m/z 819.2547 ([M+2H]$^{2+}$), C$_{58}$H$_{62}$N$_{20}$O$_{20}$, calcd. 819.2532. X-ray crystal structure of bis-ns-CB[10]•phenylenediamine$_2$.

Figure 31:
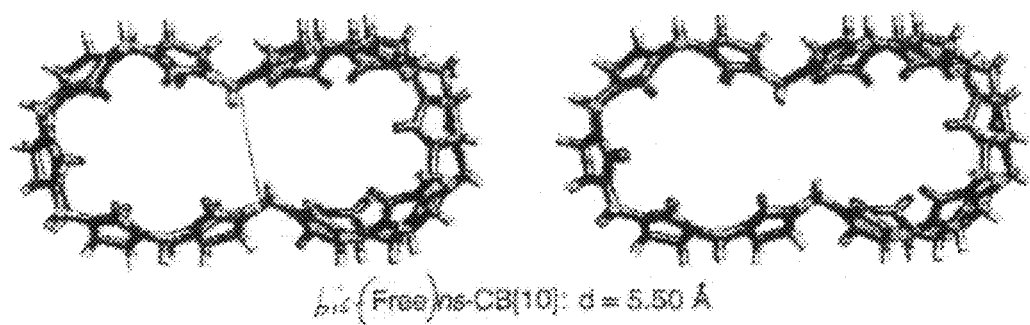
FIG. 31 illustrates on MMFF minimized model (Spartan) of bis-ns-CB[10]: d=5.50 Å.

FIG. 31 illustrates a MMFF minimized model (Spartan) of bis-ns-CB[10]: d=5.50 Å, rendered with CrystalMaker. Value given for d refers to the non-bonded H$_2$C•••CH$_2$ distance.

Synthesis Example for the Formation of Complexes of bis-ns-CB[10]

The solid forms of a given guest (5.0 μmoles) and an excess of bis-ns-CB[0] (3.0 μmoles, 6 mg) were mixed in a 5 mL vial. To the vial was added 0.6 mL D$_2$O. The heterogenous mixture was then sonicated for 1 minute, filtered, and transferred to an NMR tube for analysis. This procedure was conducted with many guest compounds including p-xylylene diamine, 1,5-diaminonaphthalene, diaminobenzidine, diaminoacridine, diaminomelamine, dimethylaminomethyl ferrocene, aminocoumarin, nile blue perchlorate, dimethyldiazapyrenium iodide, 4-aminophenylalanine, L-tryptophan, L-arginine, dodecylmethyl ephedrinium bromide and 1-aminoadamantane, for example.

In fact, the nor-seco-type cucurbit[n]uril compounds of the present invention form host-guest complexes with a wide variety of guest compounds.

Figure 2:
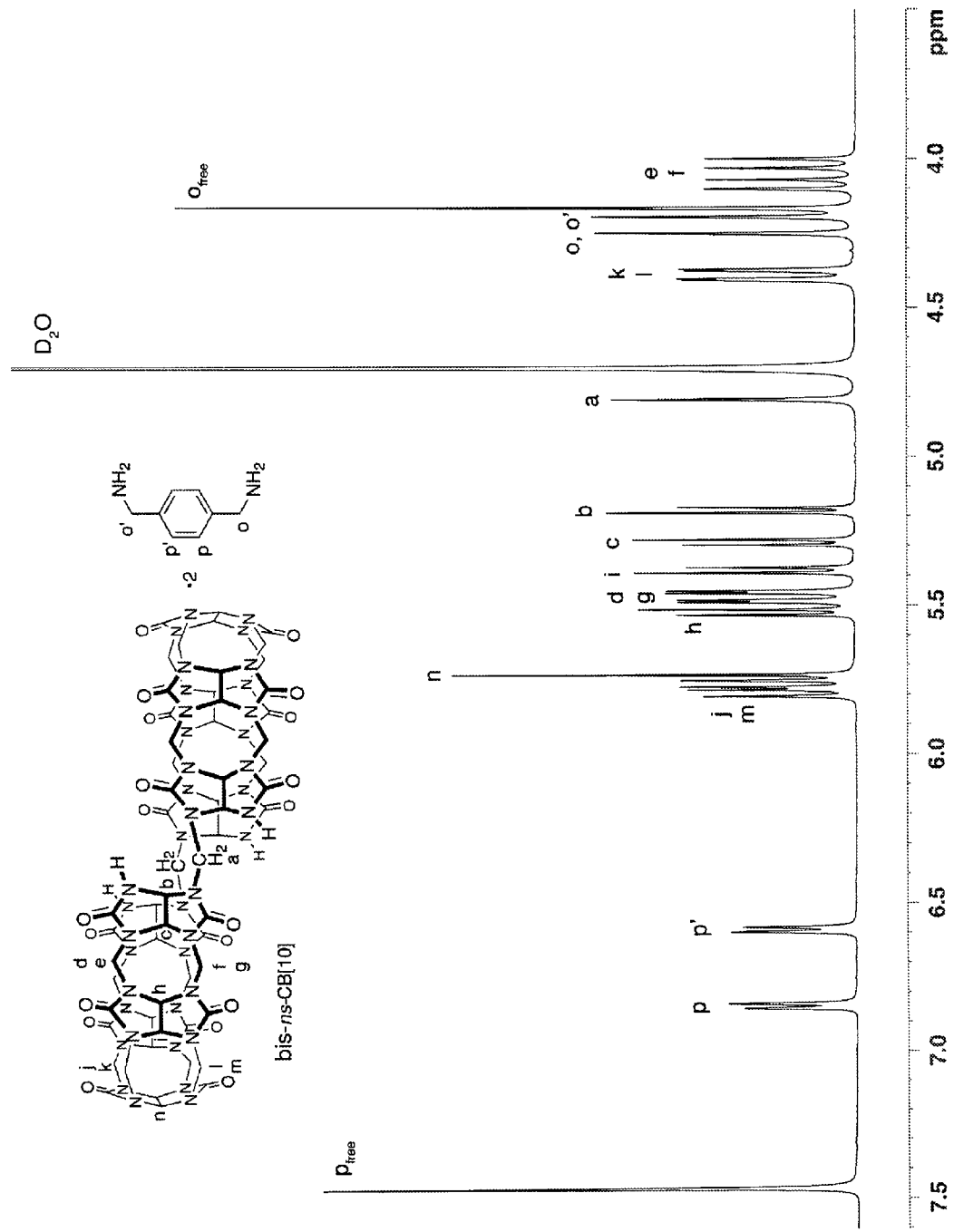
FIG. 2 is a $^1$H NMR spectrum for bis-ns-CB[10]•guest #2$_2$ and excess 2 in $D_2O$.

FIG. 2 is a $^1$H NMR spectrum for bis-ns-CB[10]•guest #2$_2$ and excess 2 in D$_2$O.

Figure 3:
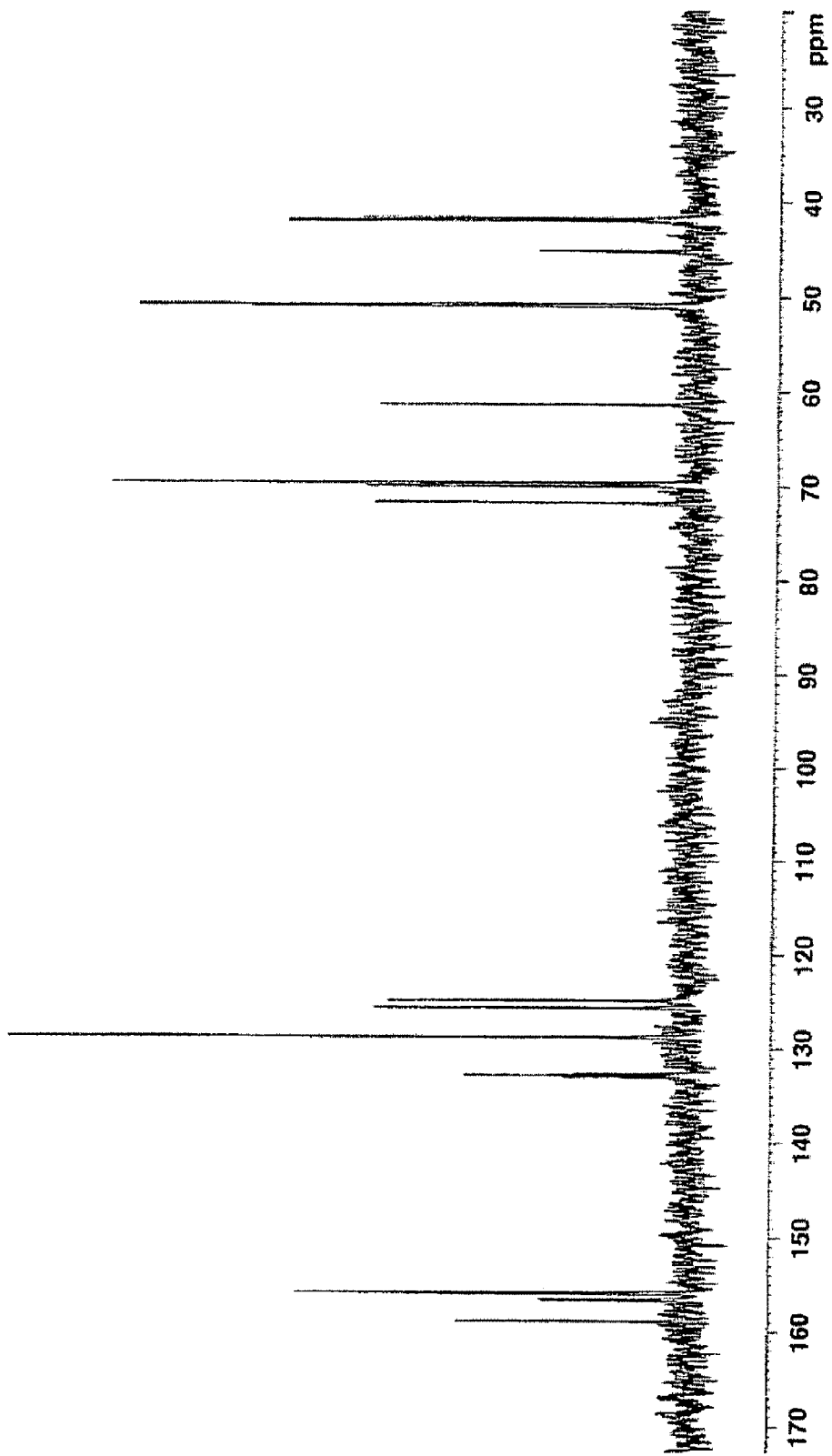
FIG. 3 is a $^{13}$C NMR spectrum for bis-ns-CB[10]•guest #2$_2$ and excess 2 in $D_2O$.

FIG. 3 is a $^{13}$C NMR spectrum for bis-ns-CB[10]•guest #2$_2$ and excess 2 in D$_2$O.

Figure 4:
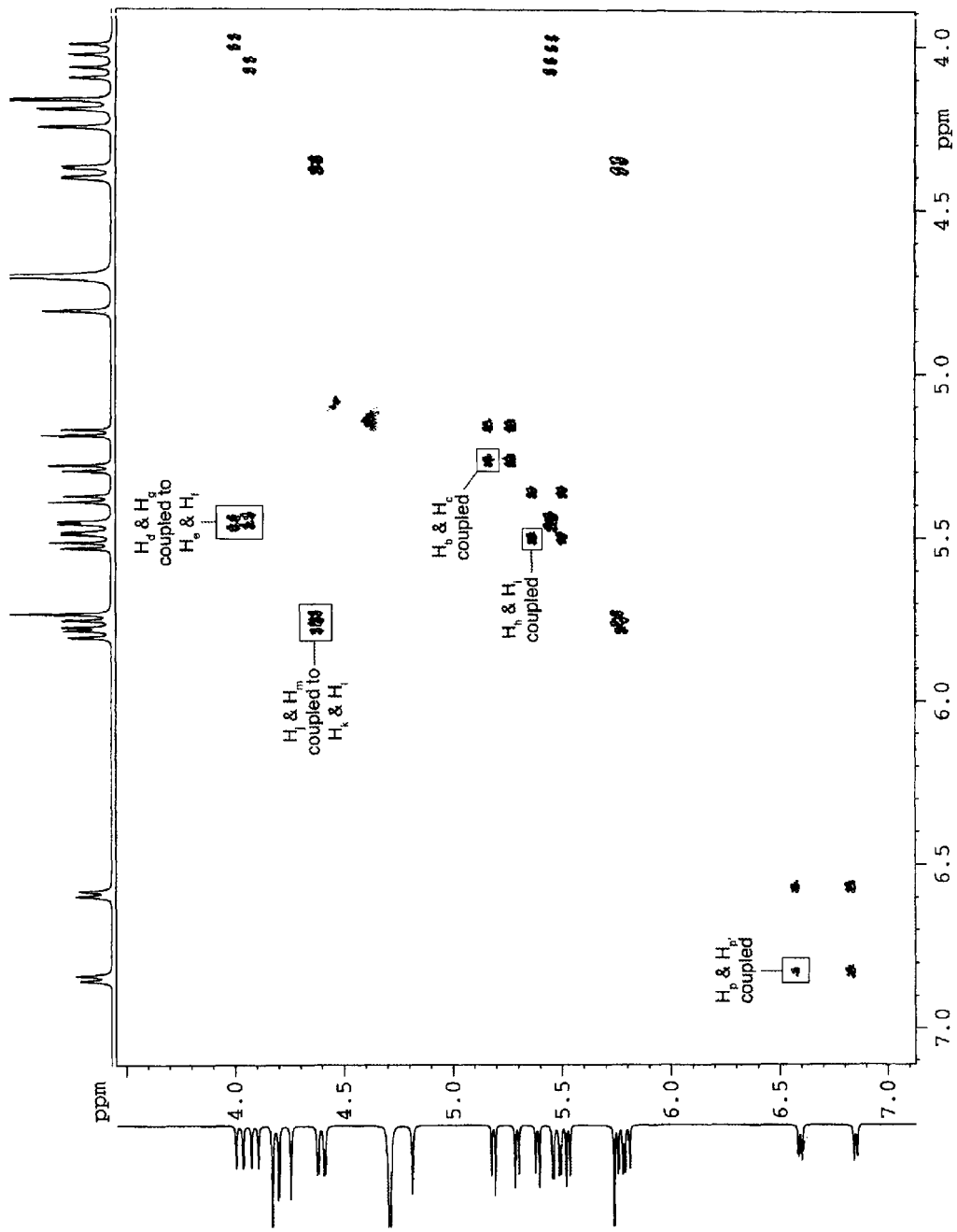
FIG. 4 is a $^1$H-$^1$H COSY spectrum for bis-ns-CB[10]•guest #2$_2$ with excess 2 in $D_2O$.

FIG. 4 is a $^1$H-$^1$H-COSY spectrum for bis-ns-CB[10]•guest #2$_2$ and excess 2 in D$_2$O.

Figure 5:
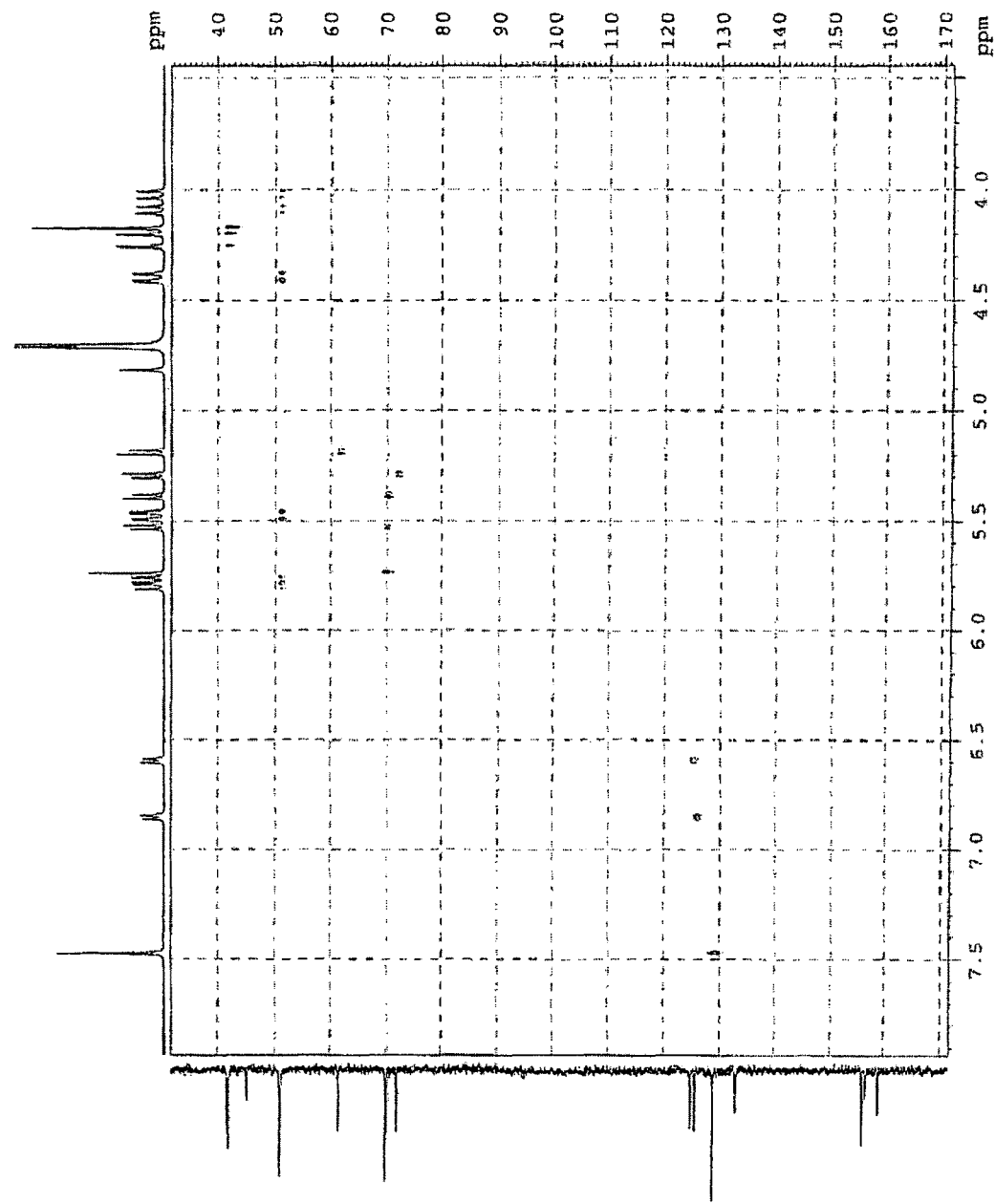
FIG. 5 is a $^1$H-$^{13}$C HSQC spectrum for bis-ns-CB[10]•guest #2$_2$ in $D_2O$.

FIG. 5 is a $^1$H-$^{13}$C HSQC spectrum for bis-ns-CB[10]•guest #2$_2$ in D$_2$O.

Figure 6:
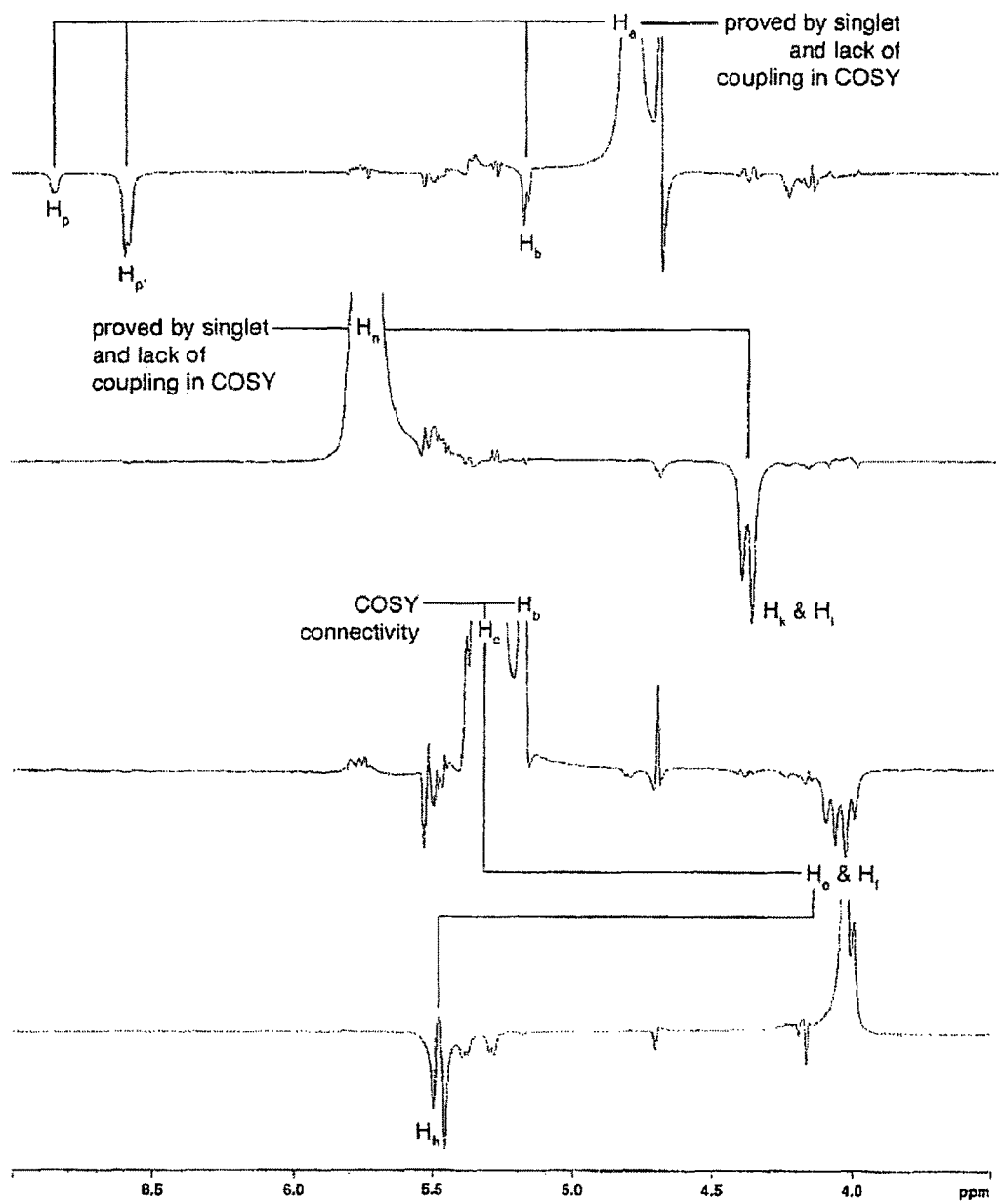
FIG. 6 illustrates traces from the 2D ROESY spectrum for bis-ns-CB[10]•guest #2$_2$ (500 MHz, $D_2O$, RT) used in conjunction with the COSY-spectrum (FIG. 4) to assign the $^1$H NMR resonances as shown in FIG. 1.

FIG. 6 illustrates traces from the 2D ROESY spectrum for bis-ns-CB[10]•guest #2.

Figure 7:
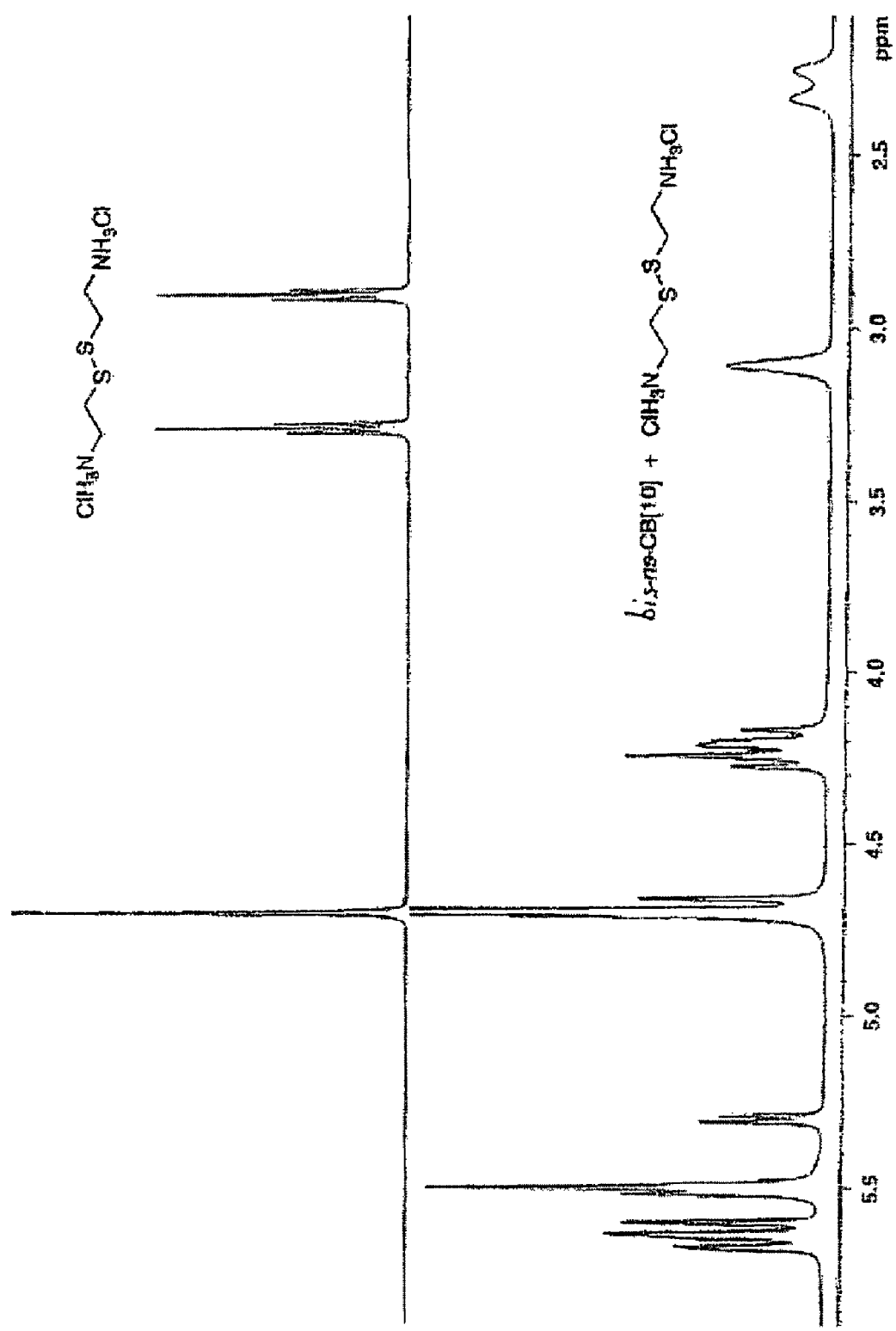
FIG. 7 shows $^1$H NMR spectra for cystamine (guest #5, as the dichloride) and its complex with bis-ns-CB[10] (500 MHz, $D_2O$, RT).

FIG. 7 is a $^1$H NMR spectrum for cystamine (guest #5, as the dichloride) and its complex with bis-ns-CB[10].

Figure 8:
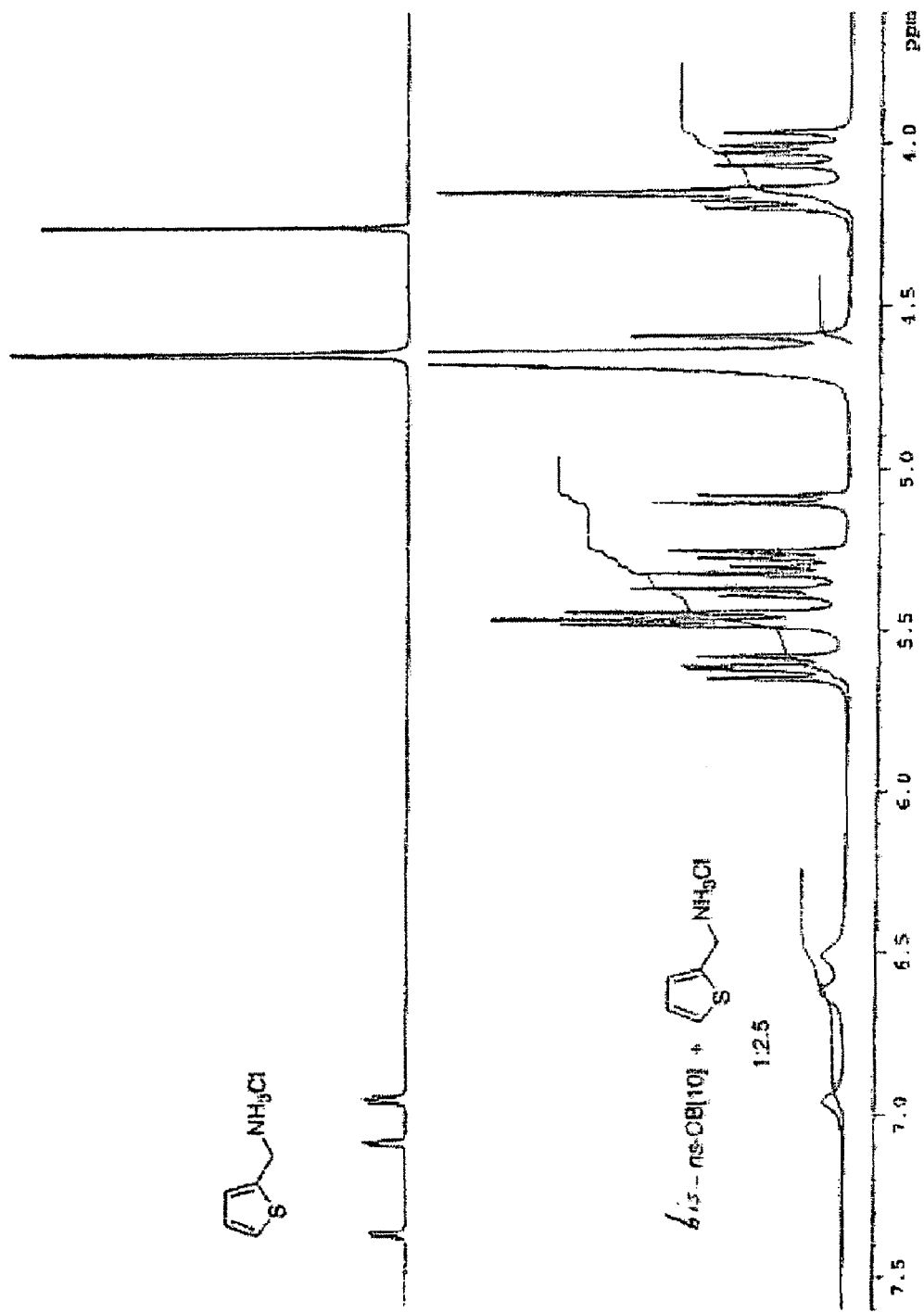
FIG. 8 shows $^1$H NMR spectra for thiophene methyl amine (as the chloride) and its complex with bis-ns-CB[10] (500 MHz, $D_2O$, RT).

FIG. 8 is a $^1$H NMR spectrum for thiophene methyl amine (as the chloride) and its complex with bis-ns-CB[10].

Figure 9:
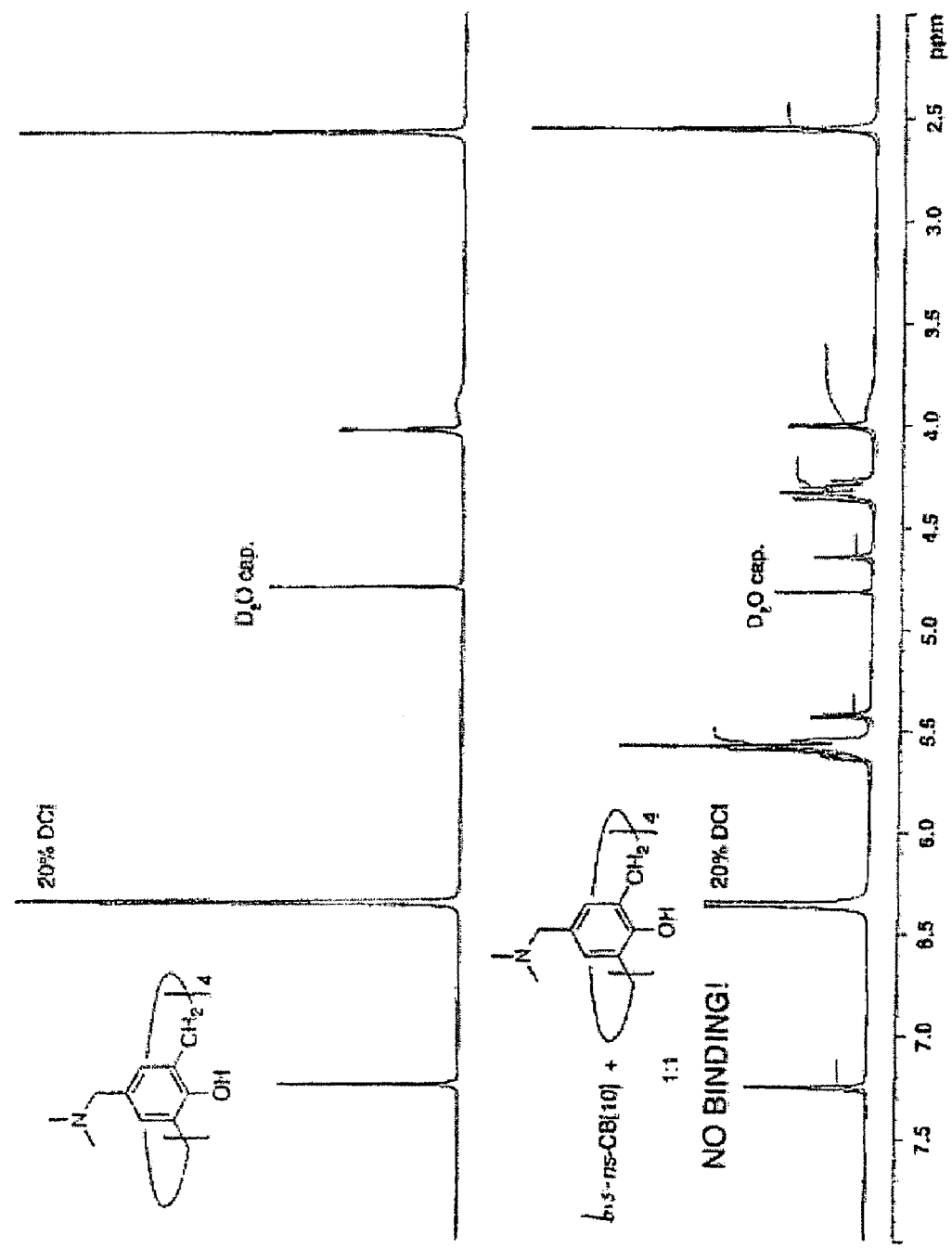
FIG. 9 shows a $^1$H NMR spectra recorded for cationic calix[4] arene and its non-binding mixture with bis-ns-CB[10] (500 MHz, $D_2O$, RT).

FIG. 9 is a $^1$H NMR spectrum recorded for cationic calix[4] arene and its non-binding mixture with bis-ns-CB[10].

Figure 10:
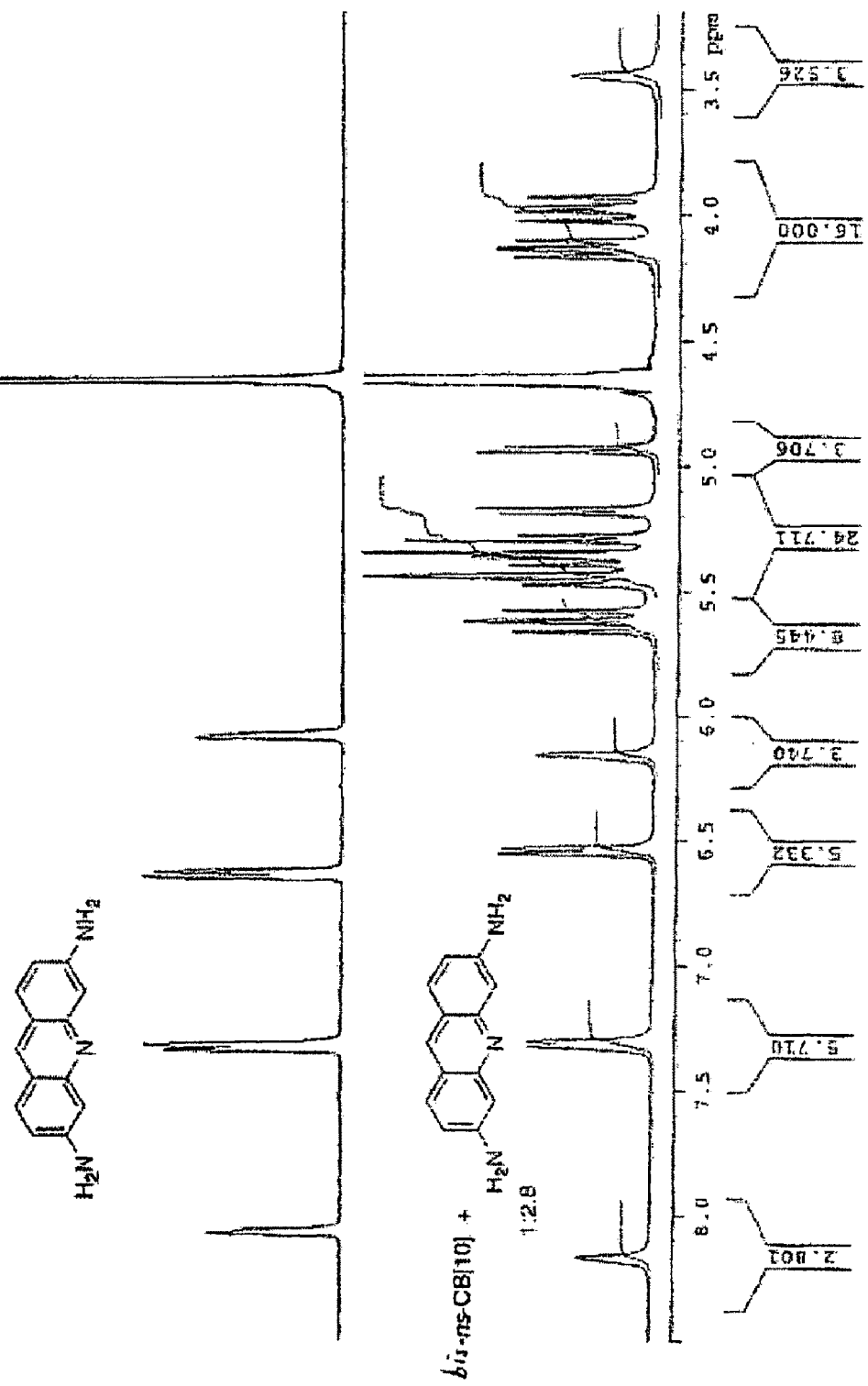
FIG. 10 is a $^1$H NMR spectrum recorded for diaminoacridine and its complex with bis-ns-CB[10] (400 MHz, $D_2O$, RT).
Figure 11:
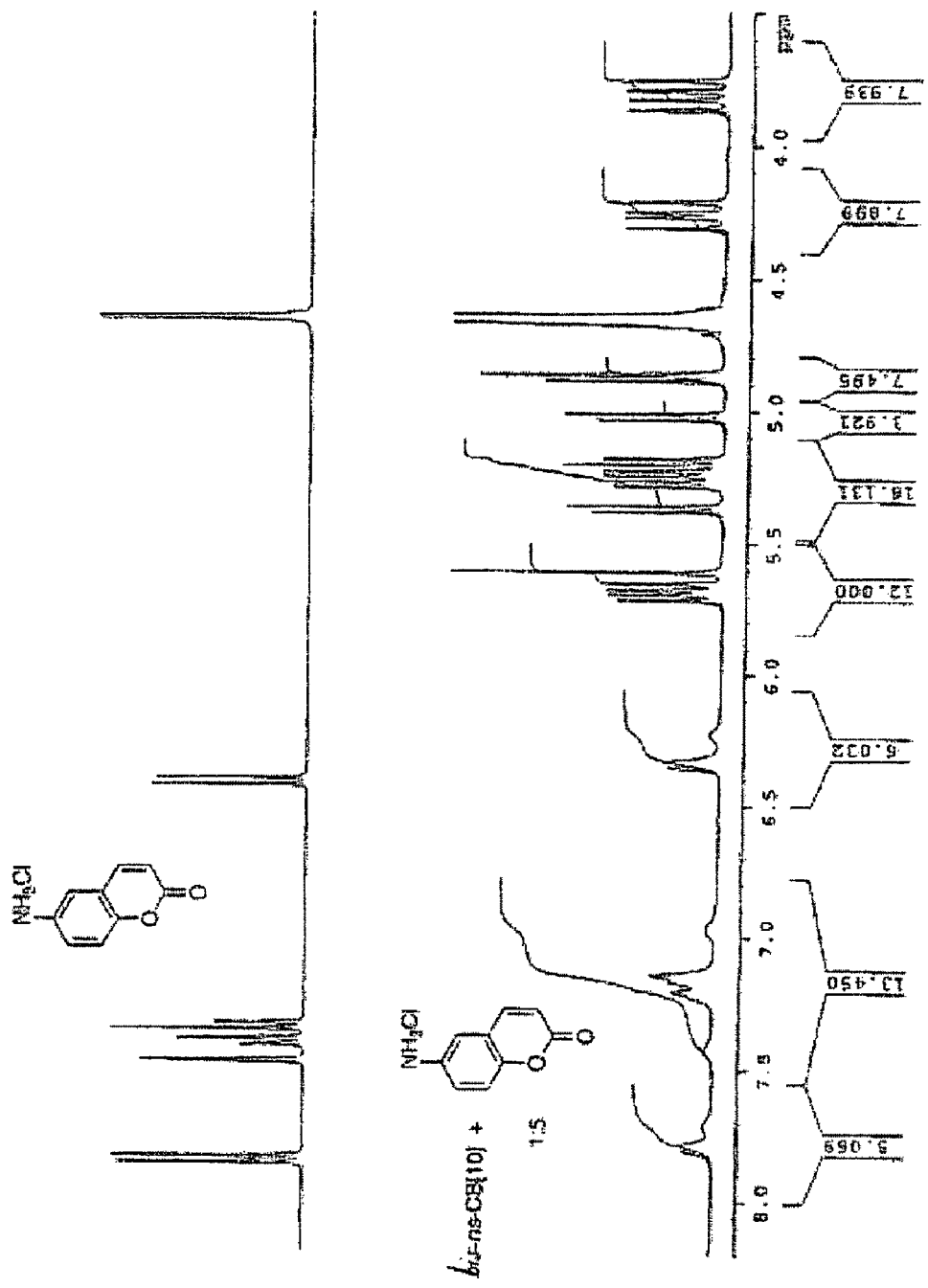
FIG. 11 is a $^1$H NMR spectrum recorded for aminocoumarin and its complex with bis-ns-CB[10] (400 MHz, $D_2O$, RT).
Figure 12:
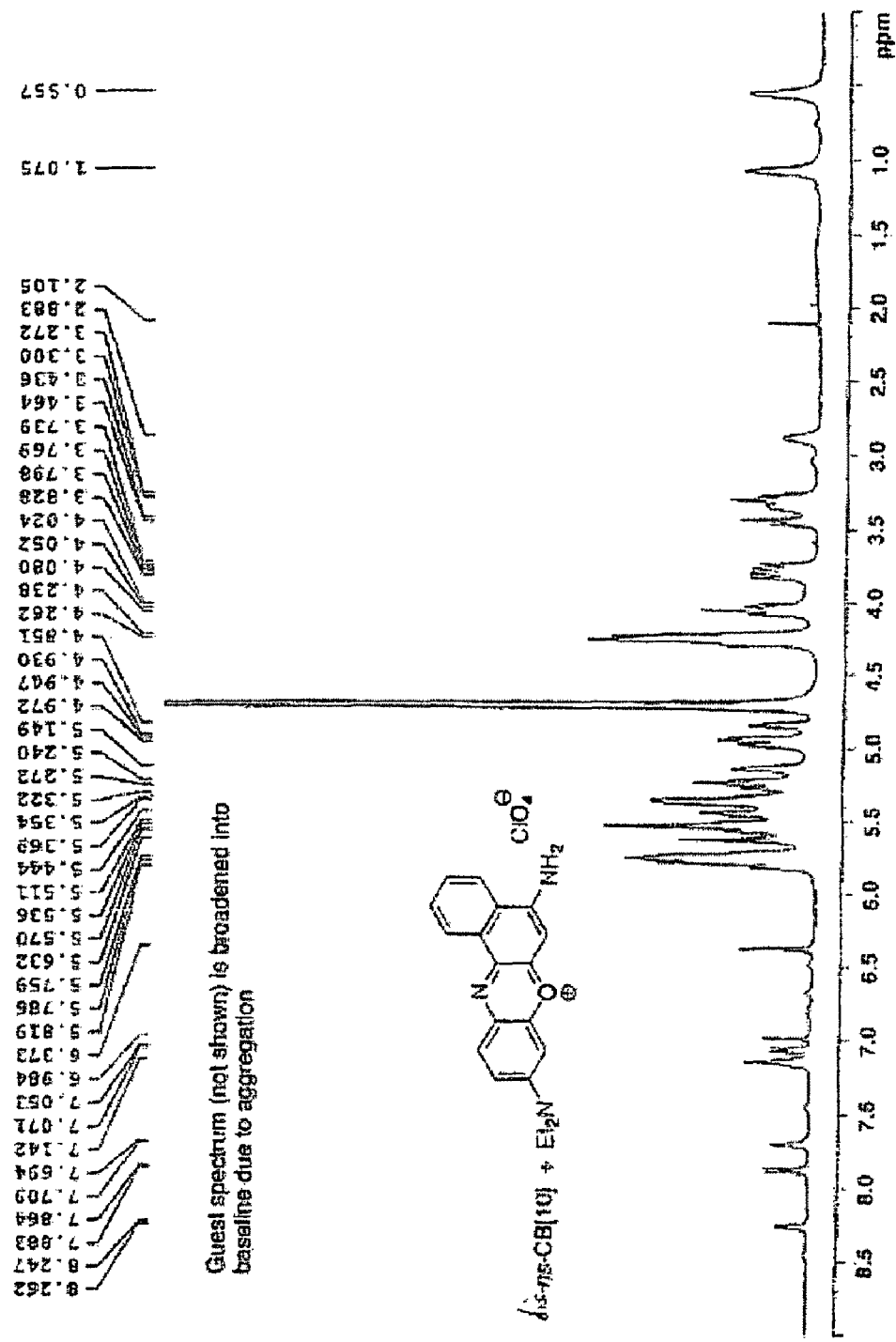
FIG. 12 is a $^1$H NMR spectrum recorded for nile blue perchlorate and its complex with bis-ns-CB[10] (500 MHz, $D_2O$, RT).

FIGS. 10, 11 and 12 show binding with a commonly used dye species. The complexation of the dye with the host compound stabilizes the dye against decomposition and extends the life of the dye.

Figure 13:
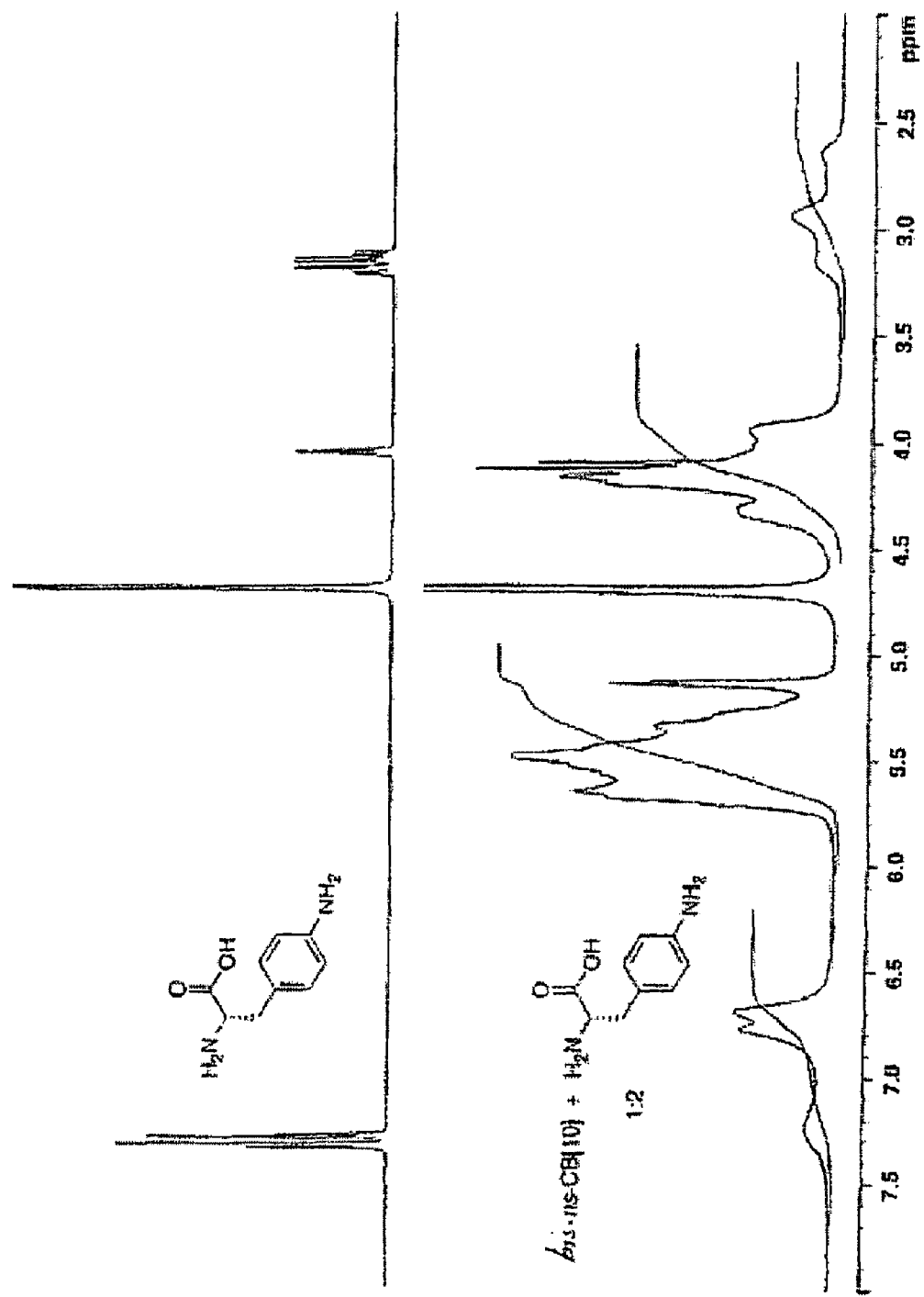
FIG. 13 is a $^1$H NMR spectrum recorded for 4-aminophenylalanine and its complex with bis-ns-CB[10] (500 MHz, $D_2O$, RT).
Figure 14:
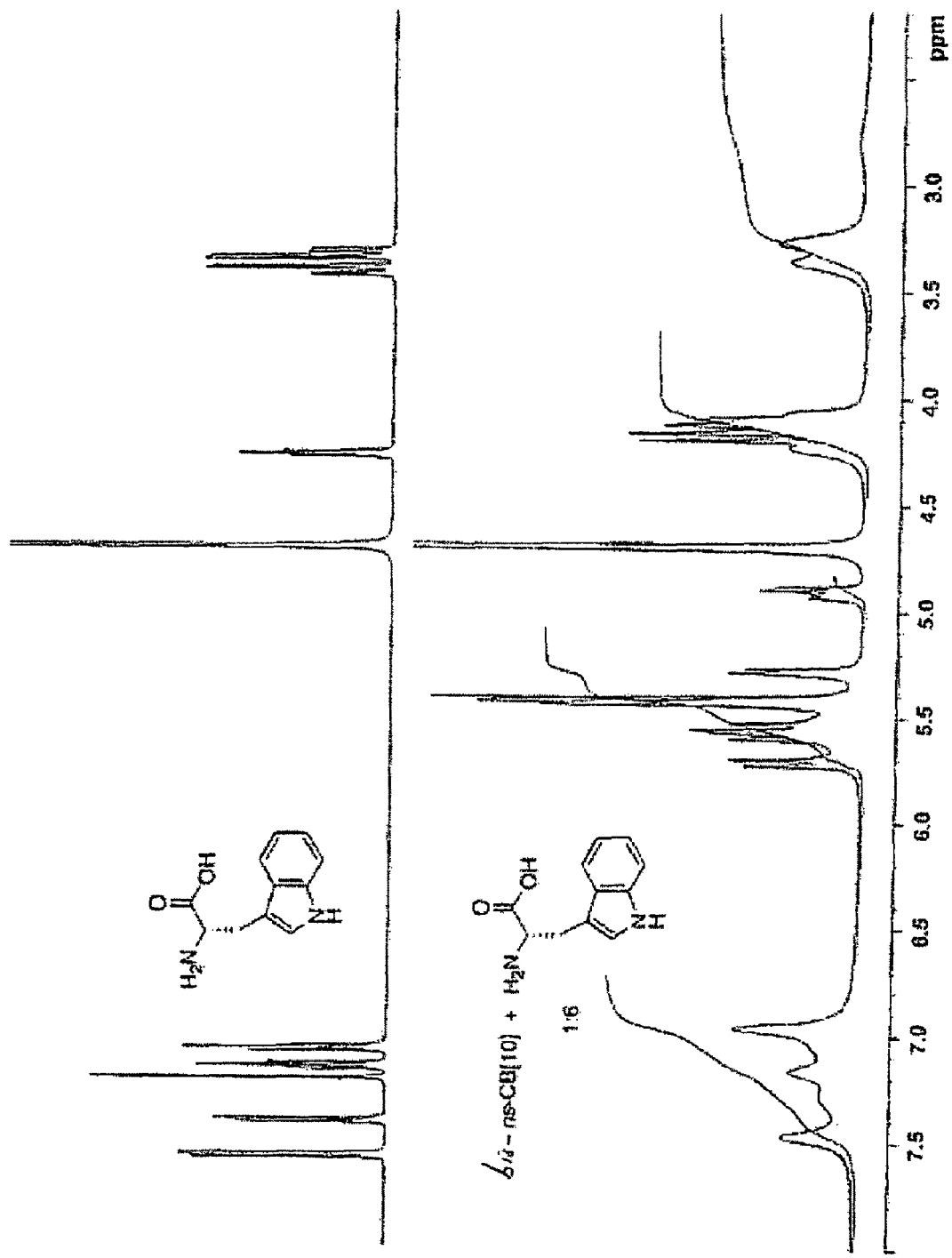
FIG. 14 is a $^1$H NMR spectrum recorded for L-tryptophan and its complex with bis-ns-CB[10] (500 MHz, $D_2O$, RT).
Figure 15:
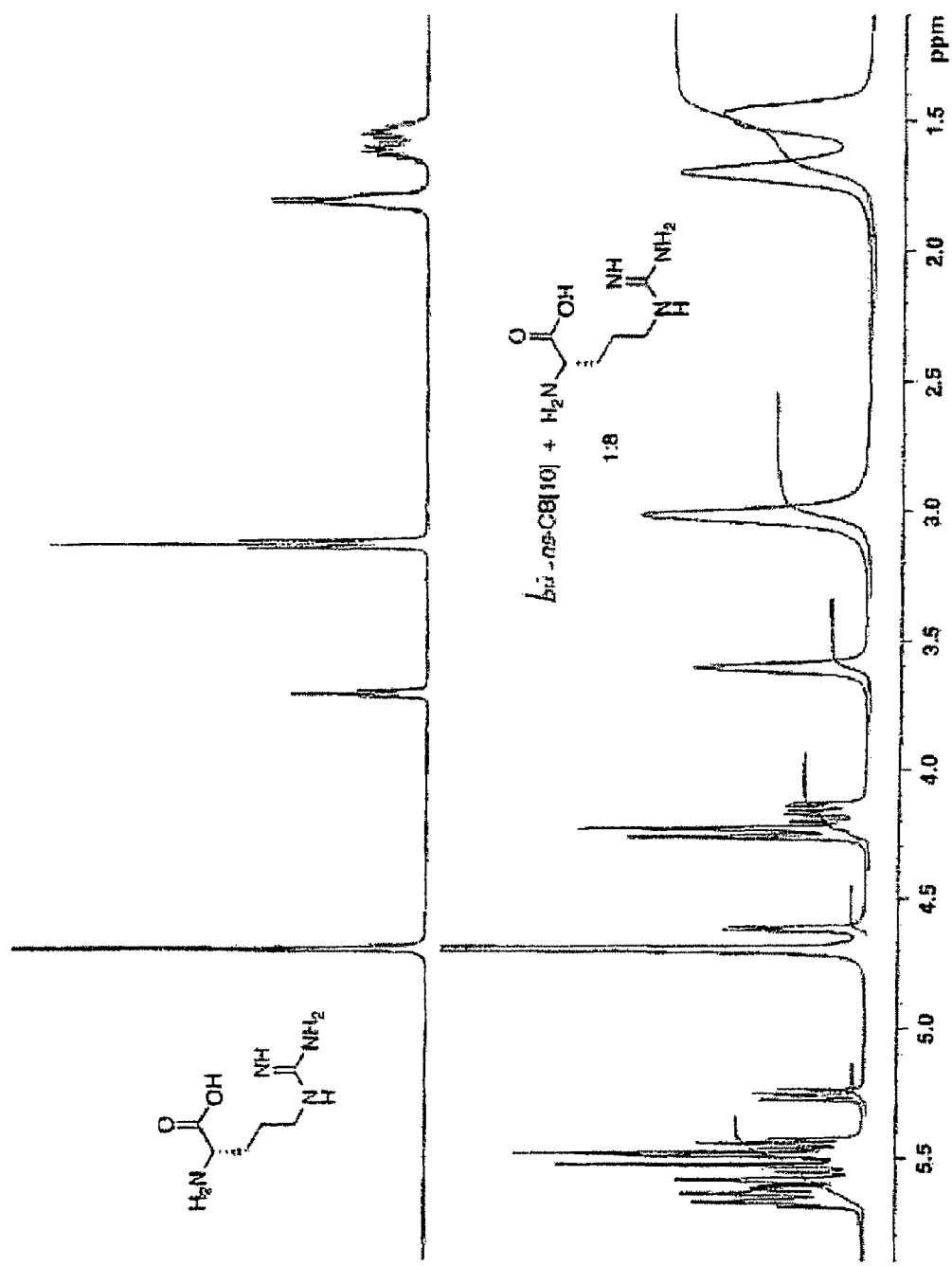
FIG. 15 is a $^1$H NMR spectrum recorded for L-arginine and its complex with bis-ns-CB[10] (500 MHz, $D_2O$, RT).

FIGS. 13-15 show binding to amino acids. This indicates that nor-seco-type CB[n] compounds are useful in modifying the properties of proteins, in drug delivery, in immobilization on solid supports (e.g. Biochips), and in chromatographic applications with (chiral) drugs.

Figure 16:
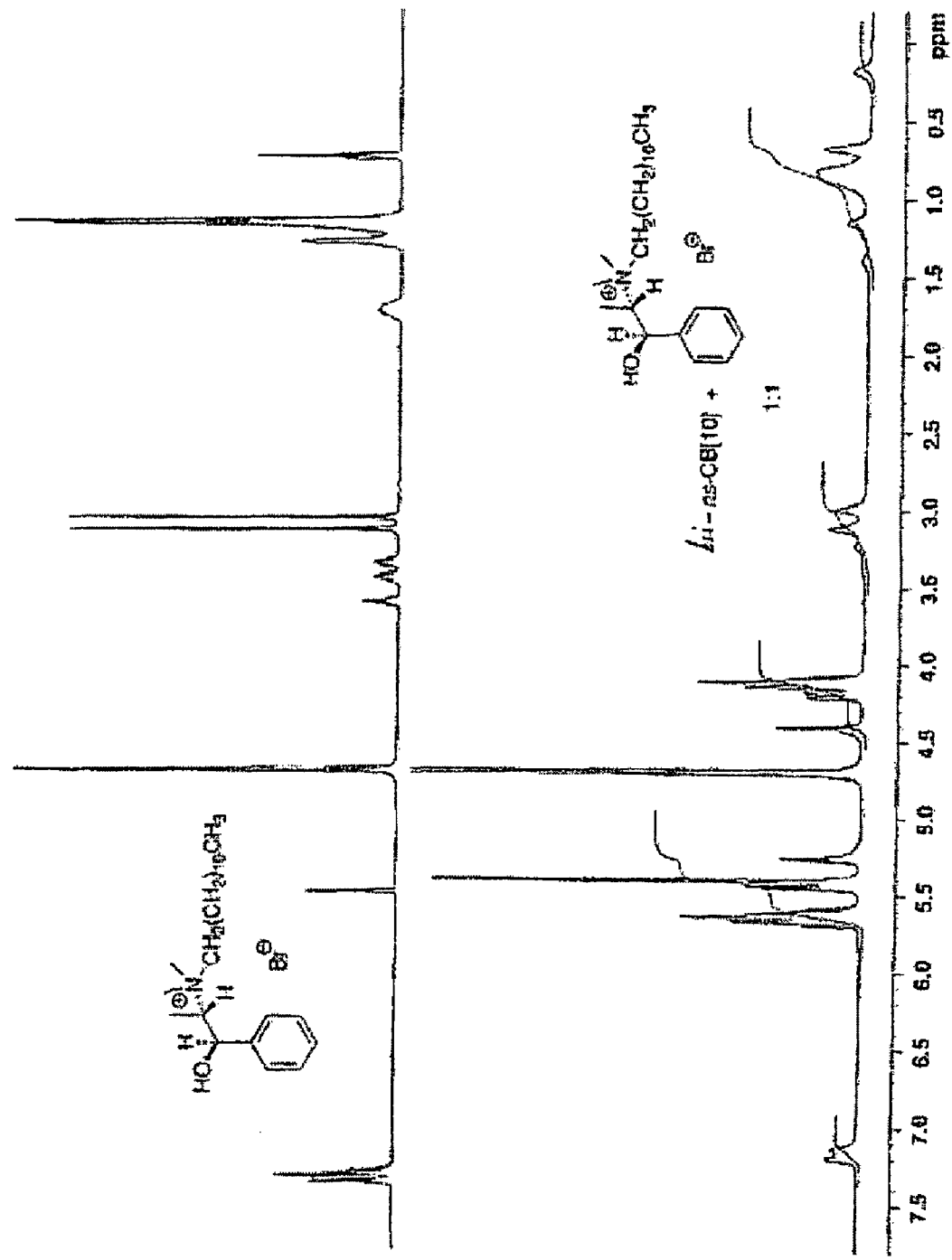
FIG. 16 is a $^1$H NMR spectrum recorded for dodecyl ephedrinium bromide and its complex with bis-ns-CB[10] (500 MHz, $D_2O$, RT).
Figure 17:
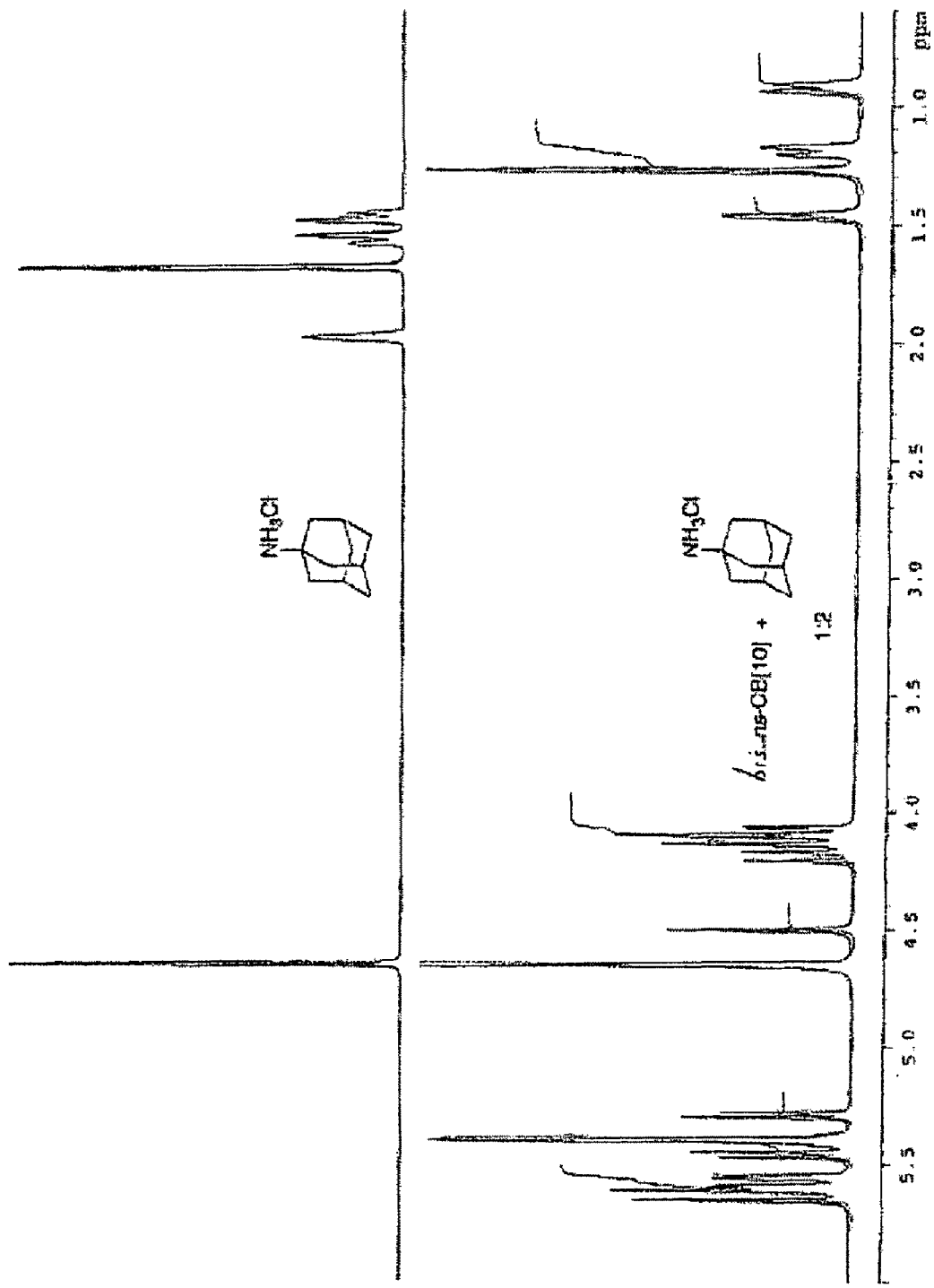
FIG. 17 is a $^1$H NMR spectrum recorded for 1-aminoadamantane and its complex with bis-ns-CB[10] (500 MHz, $D_2O$, RT).
Figure 18:
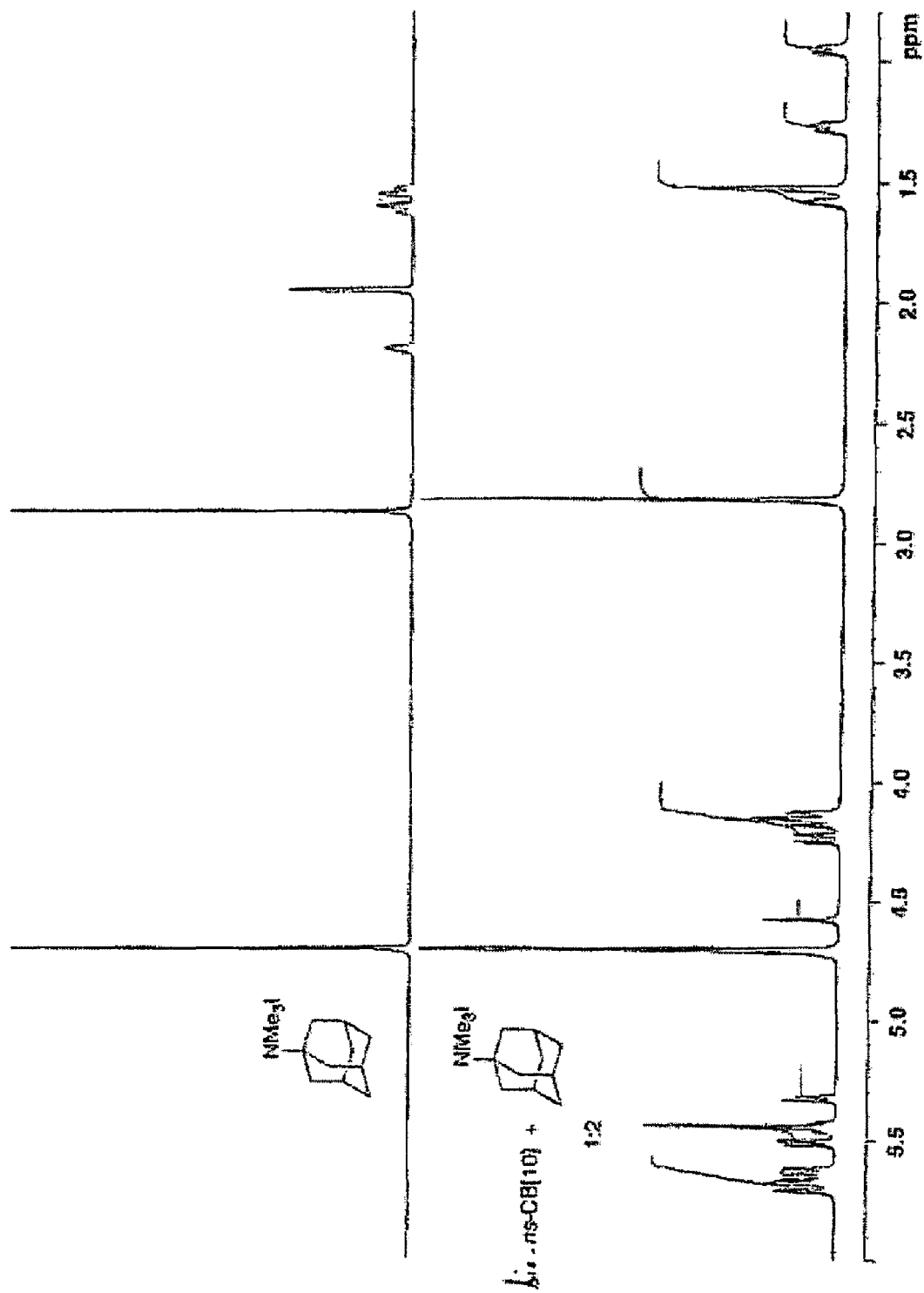
FIG. 18 is a $^1$H NMR spectrum recorded for trimethylammonium iodide and its complex with bis-ns-CB[10] (500 MHz, $D_2O$, RT).
Figure 19:
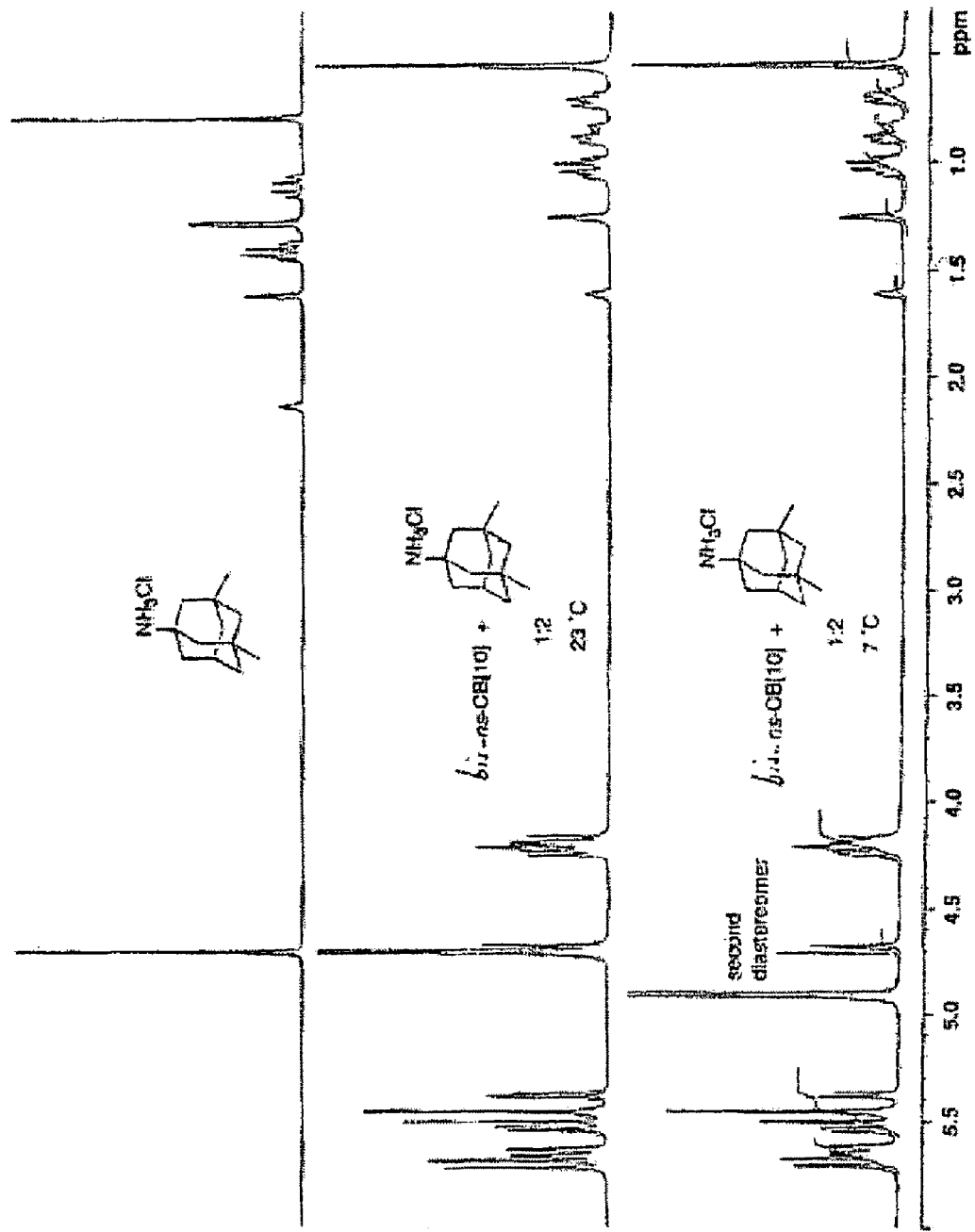
FIG. 19 is a $^1$H NMR spectrum recorded for 1-amino-3,5-dimethyladamantane and its complex with bis-ns-CB[10] (500 MHz, $D_2O$, RT).
Figure 20:
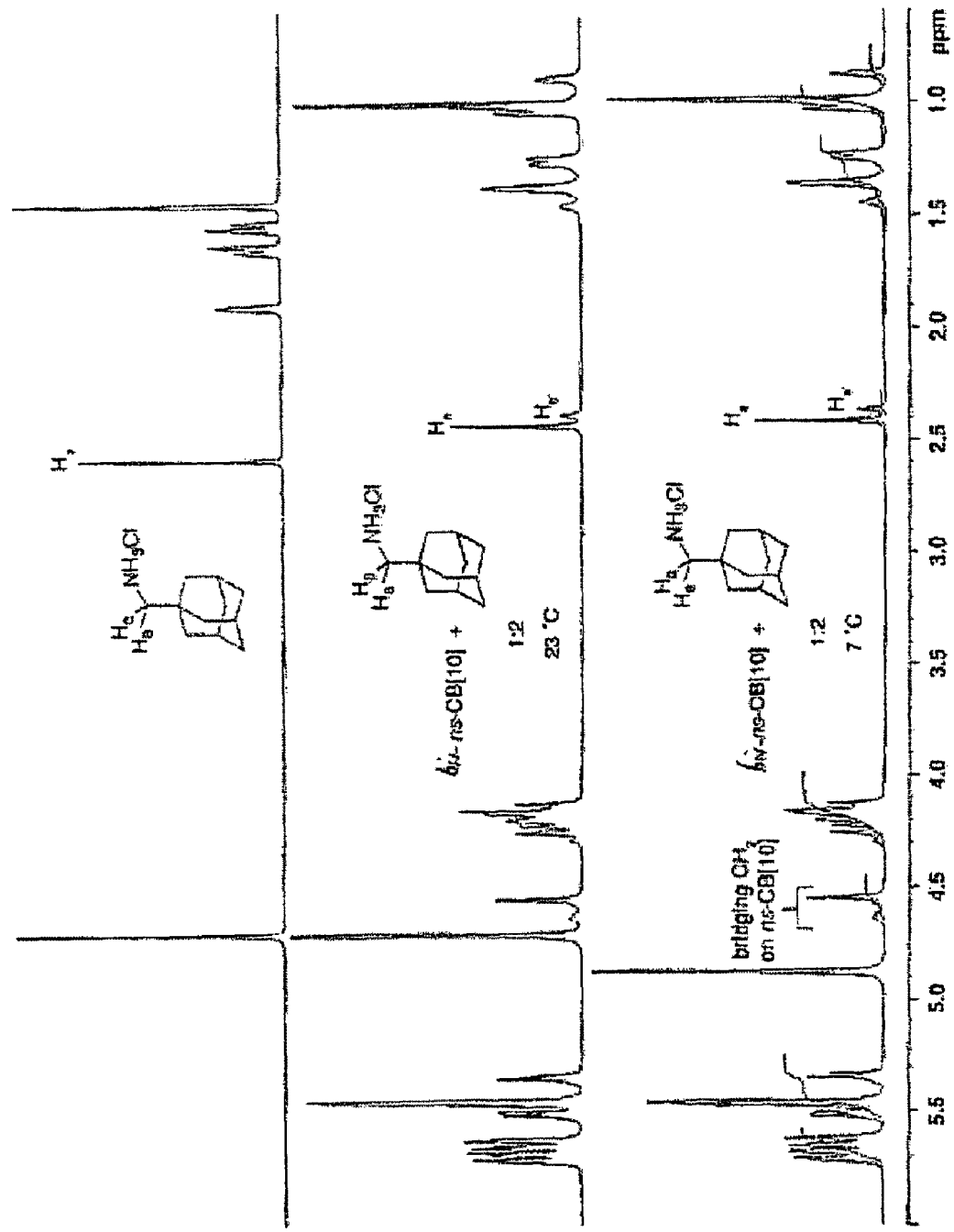
FIG. 20 is a $^1$H NMR spectrum recorded for methylamine and its complex with bis-ns-CB[10] (500 MHz, $D_2O$, RT).
Figure 21:
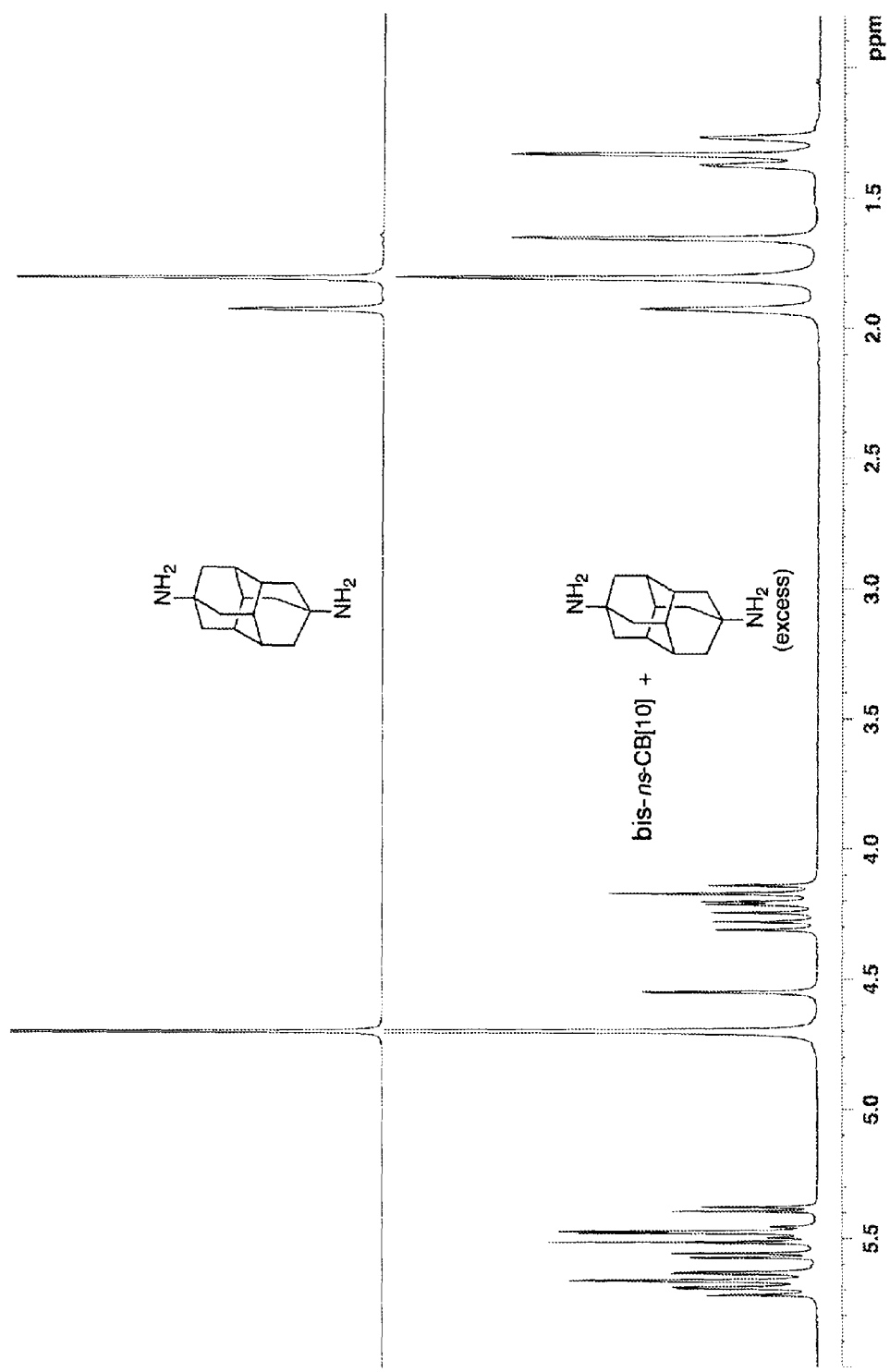
FIG. 21 is a $^1$H NMR spectrum recorded for diamantanediamine and its complex with bis-ns-CB[10] (500 MHz, $D_2O$, RT).
Figure 22:
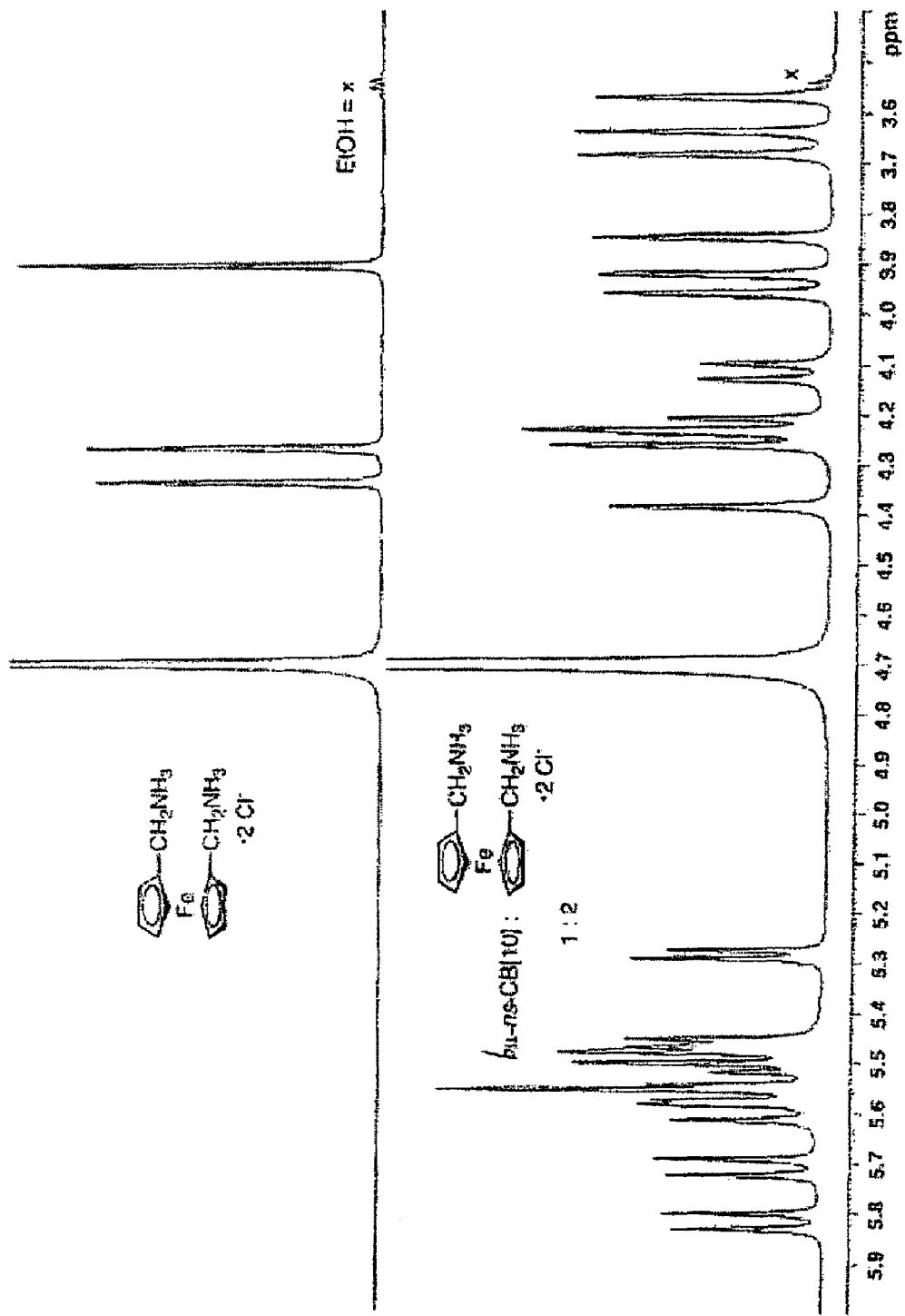
FIG. 22 is a $^1$H NMR spectrum recorded for bis(aminomethyl) ferrocene and its complex with bis-ns-CB[10] (500 MHz, $D_2O$, RT).
Figure 23:
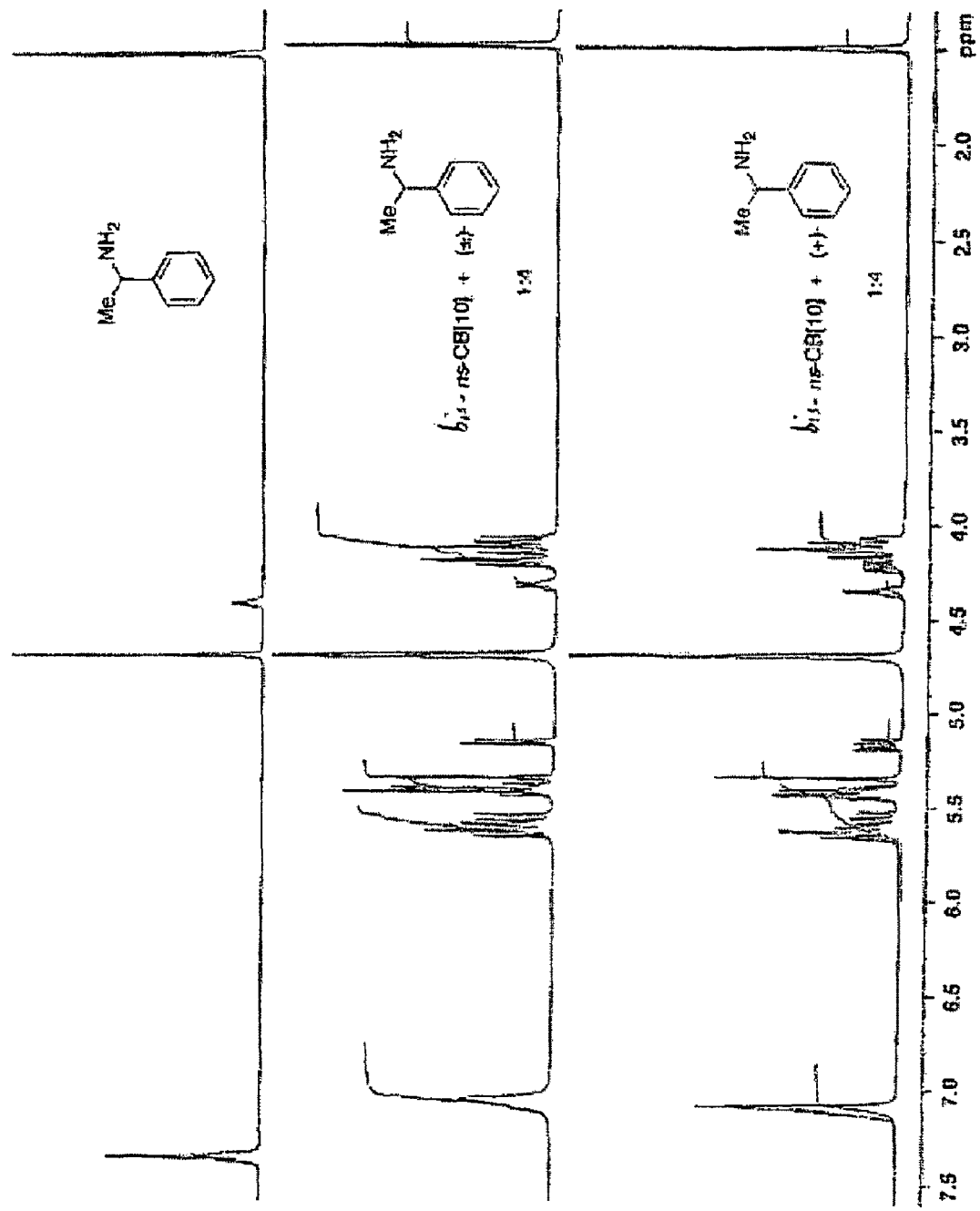
FIG. 23 is a ¹H NMR spectrum recorded for racemic phenethylamine, its complex with bis-ns-CB[10] (500 MHz, D₂O, RT).
Figure 24:
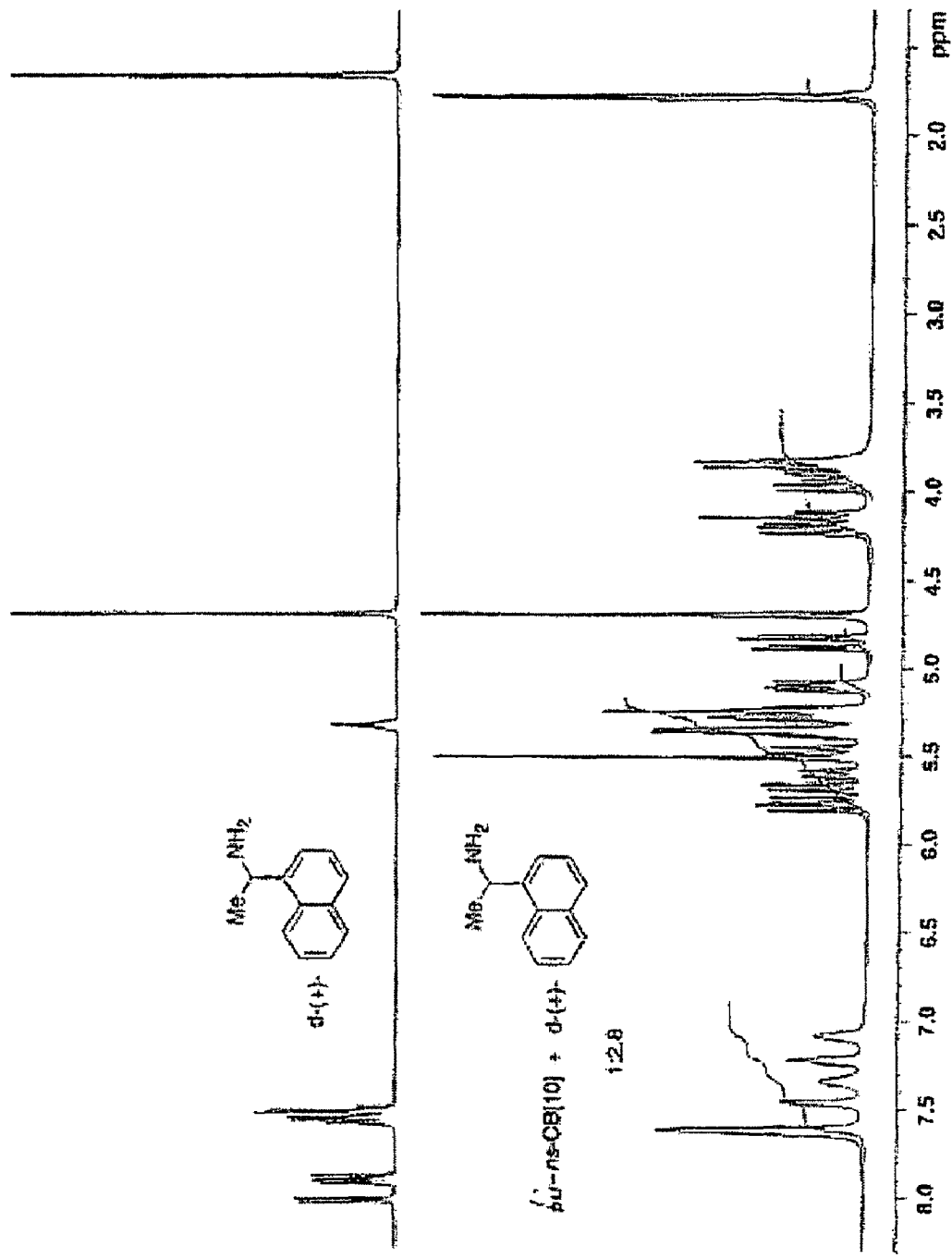
FIG. 24 is a ¹H NMR spectrum recorded for enantiomerically pure (±)-naphthylethylamine and its complex with bis-ns-CB[10] (500 MHz, D₂O, RT).
Figure 25:
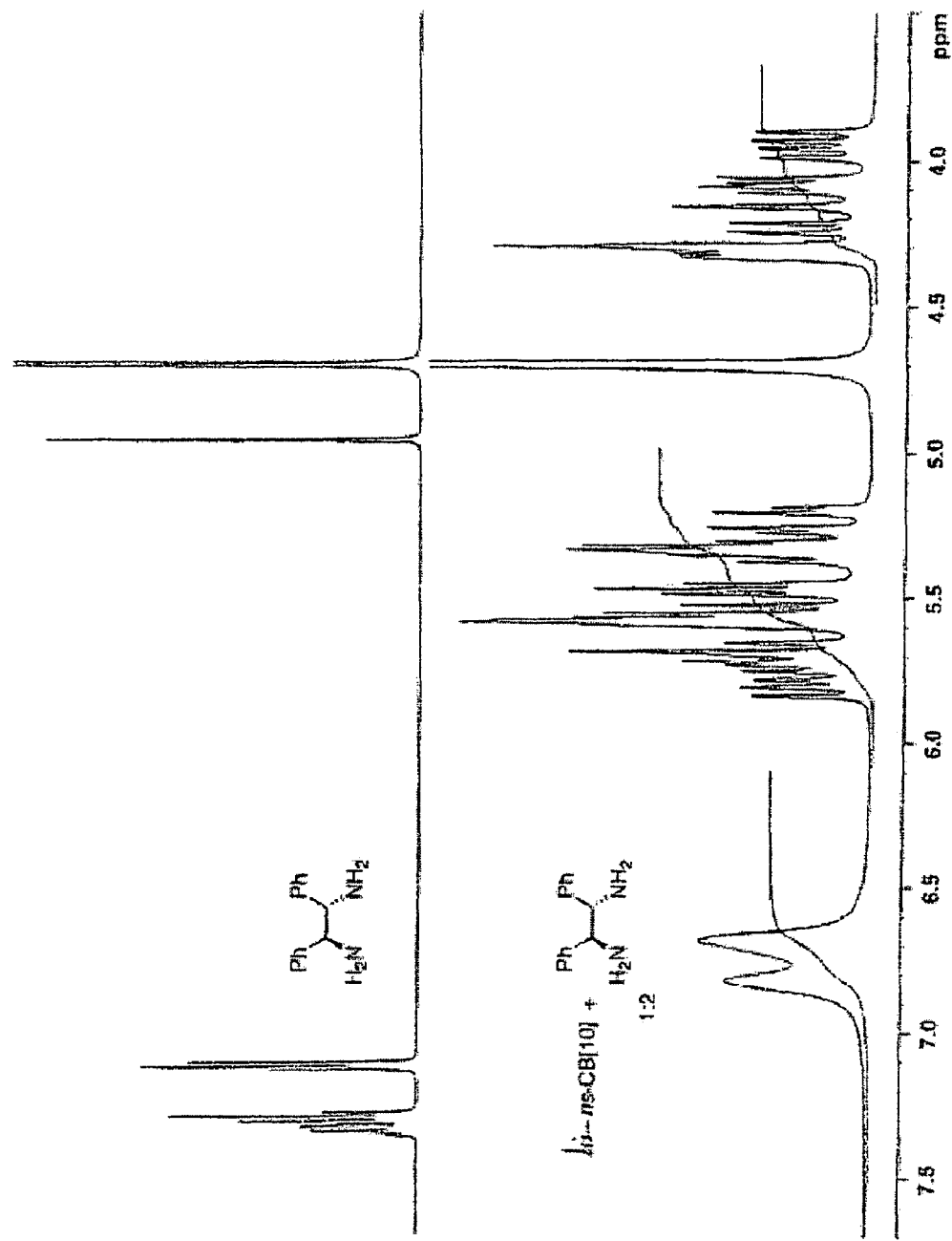
FIG. 25 is a ¹H NMR spectrum recorded for (S,S)-diphenylethylene diamine and its complex with bis-ns-CB[10] (500 MHz, D₂O, RT).
Figure 26:
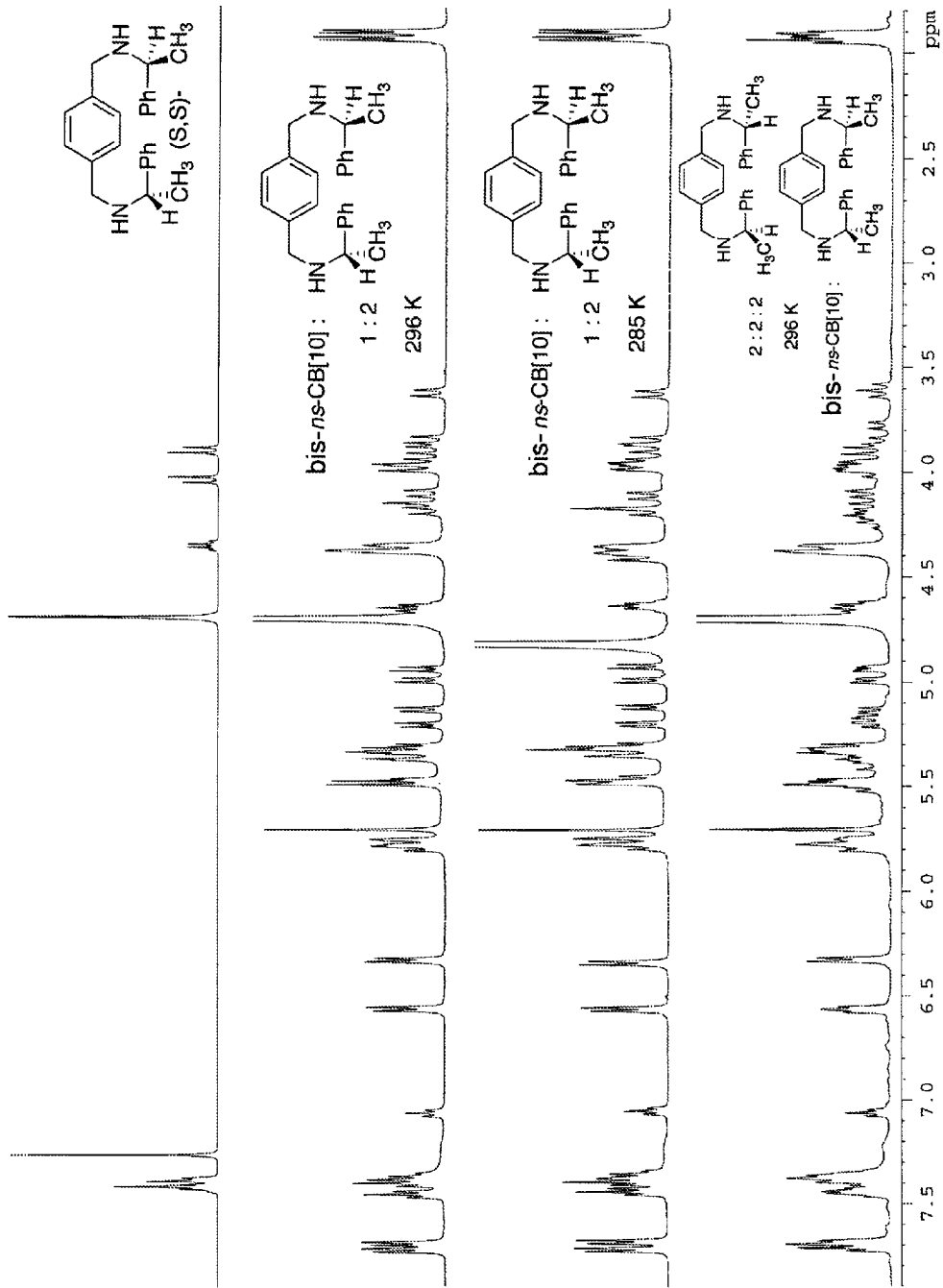
FIG. 26 is a ¹H NMR spectrum recorded for the (S,S)-chiral diamine, its complex with bis-ns-CB[10] at 285° K and 296° K, and for the bis-ns-CB[10] complex with the racemate (500 MHz, D₂O).

FIG. 16 shows bis-ns-CB[10] binding to a lipid. Such lipids often form vesicles. This experiment indicates that nor-seco-type CB[n] compounds are useful in the preparation of nanoparticles by aggregation that are useful in drug delivery.

FIG. 17-22 show the 1:2 binding inside bis-ns-CB[10]. The 1:2 binding evidences the use of bis-ns-CB[10] as a non-covalent inducer of protein dimerization based on suitably tagged proteins and for related applications where two or more entities perform chemical or biological function when brought into close proximity.

FIG. 23-26 show binding with chiral amines. This establishes utility as sensors for amines (e.g. amino acids, peptide, proteins, alkaloids of abuse, neurotransmitters, etc.).

Figure 32:
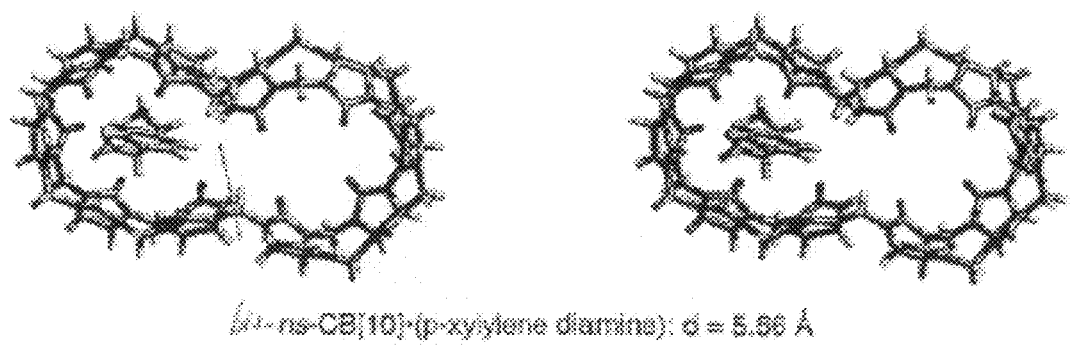
FIG. 32 illustrates an MMFF minimized model (Spartan) of bis-ns-CB[10]•(p-xylylene diamine): d=5.66 Å.

FIG. 32 illustrates a MMFF minimized model (Spartan) of bis-ns-CB[10]•(p-xylylene diamine): d=5.66 Å, rendered with CrystalMaker. The value given for d refers to the non-bonded $H_2C \cdots CH_2$ distance.

Example 2

Synthesis Example of nor-seco-type CB [n] in Methanesulfonic Acid

A solution of glycoluril (1.420 g, 9.99 mmol) in methanesulfonic acid (8 mL) was heated to 80° C. Then, paraformaldehyde (0.500 g, 16.69 mmol) was added and the reaction was stirred for two hours. The reaction mixture was cooled to room temperature and poured into methanol to give a precipitate. The precipitate was collected and washed with acetone to give a yellow solid. The solid was dried overnight under high vacuum. Analysis of the crude reaction mixture using p-xylylenediamine as probe revealed the presence of glycoluril oligomers 6-9 and n-mer, Type 5 (±)-bis-ns-CB[6], Type 5 (±)-bis-ns-CB[8], Type 3 ns-CB[6], and additional nor-seco-type CB[n] compounds. Additional nor-seco-type CB[n] compounds become apparent only after fractionation performed by Dowex ion exchange chromatography.

Example 3

Synthesis Example of nor-seco-type CB[n] in Hydrochloric Acid

A mixture of glycoluril (1.420 g, 9.99 mmo), paraformaldehyde (0.450 g, 14.99 mmol), and conc. HCl (8 mL) was heated at 80° C. for 30 minutes. The reaction mixture was cooled to room temperature and poured into methanol to give a precipitate. The precipitate was collected and washed with acetone to give an off-white solid. The solid was dried overnight under high vacuum. Analysis of the crude reaction mixture using p-xylylenediamine as probe reveals the presence of 6-9, Type 4 bis-ns-CB[10], Type 5 (±)-bis-ns-CB[6], Type 5 (±)-bis-ns-CB[8], Type 3 ns-CB[6], and additional nor-seco-type CB[n] compounds. Additional nor-seco-type CB[n] compounds become apparent only after fractionation performed by Dowex ion exchange chromatography.

Example 4

Synthesis of Glycoluril Oligomers

Procedure is the same as for nor-seco-type CB[n] compounds: A mixture of glycoluril (1.420 g, 9.99 mmol), paraformaldehyde (0.450 g, 14.99 mmol), and conc. HCl (8 mL) was heated at 80° C. for 30 minutes. The reaction mixture was cooled to room temperature and poured into methanol to give a precipitate. The precipitate was collected and washed with acetone to give an off-white solid. The solid was dried overnight under high vacuum. Dowex chromatography (1:1 formic acid:HCl (aq.)) gave pure samples of 6, 7, 8, 9 and 10 (shown in Scheme 2) in modest yield. Each of pure samples 7, 8 and 9 was then characterized by $^1H$ NMR.

Characterization data for 7 (R=H): $^1H$ NMR (400 MHz, 35% DC1): 5.69 (d, J=9, 2H), 5.58 (d. J=9, 2H), 5.53 (s, 2H), 5.38 (d, J=15.6, 4H), 4.36 (d, J=15.6, 4H), ES-MS: m/z 475 (100, $[M+H]^+$), HR-MS (ES-MS): m/z 475.1540 ($[M+H]^+$, $C_{16}H_{19}N_{12}O_6$, calcd 475.1551).

Characterization data for 8 (R=H): $^1H$ NMR (400 MHz, $D_2O$): 5.69 (d, J=16, 2H), 5.52 (d, J=16, 4H), 5.48 (d, J=9, 2H), 5.43 (d, J=9, 2H), 5.38 (d, J=9, 2H), 5.27 (d, J=9, 2H) 4.23 (d, J=16, 2H), 4.10 (d, J=16, 4H).

Characterization data for 9 (R=H): $^1H$ NMR (400 MHz, $D_2O$): 5.67 (d, J=16, 4H), 5.60 (s, 2H), 5.42 (d, J=9, 2H), 5.38 (d, J=16, 4H), 5.28 (d., J=9, 2H), 5.40-5.25 (ABq, 4H), 4.27 (d, J=16, 4H), 3.90 (d, J=16, 4H). ES-MS: m/z 472 (100, [M+ guest #2,]$^{2+}$; 0.5 spacing of $M^+$ confirmed).

Effect of Templates and Salts on the Formation of Nor-Seco-Type CB[n].

It is known that various organic templates and salts effect the ratio of CB[n] compounds produced. Similarly, the choice of templates and salts have an effect on the ratio of the various nor-seco-type CB[n] produced. That is, the effect of templates and salts upon the relative amounts of various nor-seco-type CB[n] compounds produced appears to be similar to the effect thereof on known cucurbit[n]urils. For example, bis-ns-CB[10] is produced in good quantities in HCl as solvent, but not in $MeSO_3H$ as solvent. We explicitly recognize the importance of these choices in the context of the present invention.

Notably, the addition of salts or other templating compounds to the reactant mixture appears to provide an ion templating effect. This effect causes the relative amount of produced nor-seco-type CB[n] compounds of differing unit sizes to be altered if a salt and/or templating compound is added to the reactant mixture. For convenience, both salts and other compounds are referred to herein as "templating compounds."

The templating compounds can be selected from a large number of compounds and indeed any compound that can alter the ratio of nor-seco-cucurbit[n]urils of different unit sizes produced in the method of the present invention can be used as a templating compound. The templating compound may be an organic compound, a salt of an organic compound, or an inorganic compound. Suitable compounds that may be used as a templating compound include ammonium chloride, lithium chloride, sodium chloridie, potassium chloride, rubidium chloride, cesium chloride, ammonium chloride, lithium bromide, sodium bromide, potassium bromide, rubidium bromide, caesium bromide, lithium iodide, sodium iodide, potassium iodide, rubidium iodide, caesium iodide, potassium sulfate, lithium sulfate, tetrabutylammonium chloride, tetraethylammonium chloride, o-carborane, thioacetamide, N-(1 napthyl)ethylenediamine, 2,2'-biquinoyl, p-bromoanaline, taurine, blue tetrazolium, 2-amino-3-methyl benzoic acid, indol-3-, cystine, p-acetamidoanitine, p-aminophenol, acetamide, 4-, p-aminophenol, acetamide, 4-aminoacetophenone, 4-dimethylaminobenzaldehyde, 2-aminobenzimadazol, bis-(4-4'-bipyridyl))-α,α'-p-xylene, red phosphorus, and lithium p-toluenesulfonate. The present inventors believe that a large number of other compounds could be suitable for use as templating compounds and therefore the above list should not be considered to be exhaustive. The anions of the acid may also be considered to be a template.

The templating compounds may be added singly to the reaction mixture or two or more templating compounds may be simultaneously added to the reaction mixture.

If a salt is used as the templating compound salt that is added to the mixture is preferably a metal halide, ammonium halide, or the corresponding sulfates, or metal tosylates. It is preferred that the anion of the salt corresponds to the anion of the acid used. For example, where the acid used is hydrochloric acid, a metal chloride or ammonium chloride is the preferred salt. If sulfuric acid is used, metal sulfate or ammonium sulfate is the preferred salt. Similarly, iodide containing salts are preferably used where hydriodic acid is the acid, and bromide-containing salts are preferably used where hydrobromic acid is used.

The acid is preferably a strong mineral acid or a strong organic acid. In principle, any acid can be used. The acid acts to catalyse the reactions taking place.

Preferred acids for use in the method of the first aspect of the present invention include sulfuric acid, hydrochloric acid, hydrobromic acid, hydroiodic acid, deuterated sulfuric acid, phosphoric acid, p-toluenesulfonic acid, trifluoroacetic acid and methane sulfonic acid. It will be appreciated that this list is not exhaustive and that any acid that can catalyse the reaction may be used in the method of the first aspect of the present invention.

Day and co-workers have previously investigated the influence of both molecular and ionic templates on the relative ratio of CB[5]:CB[6]:CB[7]:CB[8] formed from glycoluril and formaldehyde upon hearing under acidic conditions. Molecules and ions that act as templates can do so in two different ways—either as kinetic templates or thermodynamic templates or as both. A species is a kinetic template if it makes certain reaction channels go faster which leads to a higher proportion of a particular product. A species is a thermodynamic template if the system is under thermodynamic equilibrium and the template binds to and thereby stabilizes a particular product which enhances its yield. Day and co-workers have also reported that CB[5]-CB[7] are stable to the CB[n] forming reaction conditions. Therefore, all of the templates investigated by Day must act as kinetic templates rather than thermodynamic templates because the CB[n] forming reaction conditions are not under thermodynamic control. That explains why the template effects reported by Day are modest. Later, Day reported the use of various metal ions in the separation of a mixture of CB[5]-CB[8] by the dissolution in 0.1 M $Na_2SO_4$. Upon addition of $BaSO_4$, CB[6] precipitates which allows efficient separation of CB[6] and CB[7]. The $Na_2SO_4$ insoluble CB[5] and CB[8] can be fractionally recrystallized from HCl which yields crystalline CB[8] and soluble CB[5].

In sharp contrast to the CB[n] forming reaction reported by Day, the nor-seco-type CB[n] forming reaction is under thermodynamic control. As such, the opportunity for efficient thermodynamic temptation is realized. Therefore, the selective formation of a single nor-seco-type CB[n] in an nor-seco-type CB]n] forming reaction is reduced to the problem of using a template (either guest molecule or ion) that either induces the selective precipitation of a specific nor-seco-type CB[n] or one that selectively binds to and thereby stabilizes a single nor-seco-type product. Based on previous work in the field and in our laboratory, the discovery of such templates will be straightforward. For example, $Ba^{2+}$ which induces the selective crystallization of CB[6] also induces the crystallization of hexamer 10, ns-CB[6], and bis-ns-CB[6]. Similarly, $NH_4^+$ ions are known to precipitate CB[5]-shaped cavities, and ns-CB[5]. Efficient temptation is also possible through thermodynamic temptation which requires a guest molecule as template which binds to a specific nor-seco-type CB[n]. Through our binding studies we have determined that large guests like 3,5-dimethylaminoadamantane bind selectively to bis-ns-CB[10] and (±)-bis-ns-CB[8]. Similarly, smaller guests like hexanediamine bind to the smaller nor-seco-type CB[n] like ns-CB[6], and bis-ns-CB[6]. By including these guests in the nor-seco-type CB[n] forming reaction it is possible to bias the reaction toward those particular products. The selection of specific guests for the stabilization of specific other nor-seco-type CB[n] is straightforward by measuring the values of $K_a$ of the various nor-seco-type CB[n] toward those guests. The selection of guest of such studies is guided by previous experience in the field and by molecular modeling based on MMFF force field calculations.

Mechanistic Description of Nor-Seco-Type-CB[n] Formation.

In CB[n]-forming reactions conducted with a deficiency of formaldehyde (e.g. glycoluril:formaldehyde 1:<2), a series of methylene bridged glycoluril oligomers (e.g. 6-11) form initially. Although these oligomers $C_{2v}$-symmetrical and all the free NH groups appear to be identical, there is in fact a subtle stereochemical difference between them that influences their subsequent reactions (Scheme 3). In fact, the NH groups of oligomers 6-11 can be grouped into homotopic and enantiotopic pairs. Subsequently, molecules of oligomers 6-11 may react with other oligomers of identical or different length to yield a wide variety of nor-seco-cucurbiturils. For example, two molecules of a given length oligomer can condense with a single molecule of formaldehyde to yield either the achiral intermediate 12 by connection of enantiotopic groups or the chiral intermediate 13 by connection of homotopic groups. Subsequently, intermediate 12 can react with an additional equivalent of formaldehyde to yield Type 1 and Type 2 bis-nor-seco-CB[n] that lack two $CH_2$ groups. Type 1 and Type 2 nor-seco-CB[n] both serve as intermediates for the formation of Type 3 nor-seco-CB[n] which lack a single $CH_2$. The successful isolation of Type 3 ns-CB[6] establishes the presence of Type 1-3 ns-CB[n] as components of the CB[n] forming reaction when less than two equivalents of formaldehyde are used. Similarly, intermediate 13 reacts with an additional molecule of formaldehyde by connections between homotopic groups to yield Type 4 and type 5 bis-ns-CB[n], respectively. The successful isolation of Type 4 bis-ns-CB[10] and Type 5 (±)-bis-ns-CB[6] and Type 5 (±)-bis-ns-CB[8] firmly establish the presence of Type 4 and Type 5 bis-ns-CB[n] in the nor-seco-type CB[n] forming reaction when less than two equivalents of formaldehyde are used. Lastly, intermediates 12 and 13 can both give rise to Type 6 bis-ns-CB[n] by either homotopic or enantiotopic connection of two NH groups. Type 6 bis-ns-CB[n] can react with one molecule of formaldehyde to yield Type 7 ns-CB[n], a compound that can also be formed by end-to-end connection of two homotopic groups of a sufficiently longer oligomer (e.g. $n \geq 4$). For the sake of simplicity all of the examples shown in Scheme 3 use the glycoluril trimer (7, n=3) as both building blocks. All other pairwise combinations of building blocks (1 and 6-11) are also possible and specifically contemplated and enabled by this invention. See Table 1. These nor-seco-type CB[n] may be referred to as nor-seco-type CB[x,y] where x and y refer to the length of the glycoluril oligomer building blocks (1, 6-11, and n-mer of Scheme 2). The compounds described in Table 1 are exemplary and provided solely for purposes of illustration.

TABLE 1

| | Types 1, 2, 4, 5, and 6 are actually bis-nor-seco CB[n]. | | | | | | |
|---|---|---|---|---|---|---|---|
| | Type 1 ns-CB[x,y] | Type 2[a) ns-CB[x,y] | Type 3 ns-CB[n] | Type 4 ns-CB[x,y] | Type 5 ns-CB[x,y] | Type 6[b) ns-CB[x,y] | Type 7 ns-CB[x,y] |
| x,y x + y = 4 | 3.1 2.2 | 3.1 2.2 | n = 4 | 3.1 2.2 | 3.1 2.2 | 3.1 2.2 | n = 4 |
| x,y x + y = 5 | 4.1 3.2 | 4.1 3.2 | n = 5 | 4.1 3.2 | 4.1 3.2 | 4.1 3.2 | n = 5 |
| x,y x + y = 6 | 5.1 4.2 3.3 | 5.1 4.2 3.3 | n = 6 | 5.1 4.2 3.3 | 5.1 4.2 3.3 | 5.1 4.2 3.3 | n = 6 |
| x,y x + y = 7 | 6.1 5.2 4.3 | 6.1 5.2 4.3 | n = 7 | 6.1 5.2 4.3 | 6.1 5.2 4.3 | 6.1 5.2 4.3 | n = 7 |
| x,y x + y = 8 | 7.1 6.2 5.3 4.4 | 7.1 6.2 5.3 4.4 | n = 8 | 7.1 6.2 5.3 4.4 | 7.1 6.2 5.3 4.4 | 7.1 6.2 5.3 4.4 | n = 8 |
| x,y x + y = 9 | 8.1 7.2 6.3 5.4 | 8.1 7.2 6.3 5.4 | n = 9 | 8.1 7.2 6.3 5.4 | 8.1 7.2 6.3 5.4 | 8.1 7.2 6.3 5.4 | n = 9 |
| x,y x + y = 10 | 9.1 8.2 7.3 6.4 5.5 | 9.1 8.2 7.3 6.4 5.5 | n = 10 | 9.1 8.2 7.3 6.4 5.5 | 9.1 8.2 7.3 6.4 5.5 | 9.1 8.2 7.3 6.4 5.5 | n = 10 |
| x,y x + y = 11 | 10.1 9.2 8.3 7.4 6.5 | 10.1 9.2 8.3 7.4 6.5 | n = 11 | 10.1 9.2 8.3 7.4 6.5 | 10.1 9.2 8.3 7.4 6.5 | 10.1 9.2 8.3 7.4 6.5 | n = 11 |
| x,y x + y = 12 | 11.1 10.2 9.3 8.4 7.5 6.6 | 11.1 10.2 9.3 8.4 7.5 6.6 | n = 12 | 11.1 10.2 9.3 8.4 7.5 6.6 | 11.1 10.2 9.3 8.4 7.5 6.6 | 11.1 10.2 9.3 8.4 7.5 6.6 | n = 12 |
| x,y x + y = 13 | 12.1 11.2 10.3 9.4 8.5 7.6 | 12.1 11.2 10.3 9.4 8.5 7.6 | n = 13 | 12.1 11.2 10.3 9.4 8.5 7.6 | 12.1 11.2 10.3 9.4 8.5 7.6 | 12.1 11.2 10.3 9.4 8.5 7.6 | n = 13 |
| x,y x + y = 14 | 13.1 12.2 11.3 10.4 9.5 8.6 7.7 | 13.1 12.2 11.3 10.4 9.5 8.6 7.7 | n = 14 | 13.1 12.2 11.3 10.4 9.5 8.6 7.7 | 13.1 12.2 11.3 10.4 9.5 8.6 7.7 | 13.1 12.2 11.3 10.4 9.5 8.6 7.7 | n = 14 |
| x,y x + y = 15 | 14.1 13.2 12.3 11.4 10.5 9.6 8.7 | 14.1 13.2 12.3 11.4 10.5 9.6 8.7 | n = 15 | 14.1 13.2 12.3 11.4 10.5 9.6 8.7 | 14.1 13.2 12.3 11.4 10.5 9.6 8.7 | 14.1 13.2 12.3 11.4 10.5 9.6 8.7 | n = 15 |
| x,y x + y = 16 | 15.1 14.2 13.3 12.4 11.5 10.6 9.7 8.8 | 15.1 14.2 13.3 12.4 11.5 10.6 9.7 8.8 | n = 16 | 15.1 14.2 13.3 12.4 11.5 10.6 9.7 8.8 | 15.1 14.2 13.3 12.4 11.5 10.6 9.7 8.8 | 15.1 14.2 13.3 12.4 11.5 10.6 9.7 8.8 | n = 16 |

[a)]When x ≠ y, Type 2 bis-ns-CB[x,y] are chiral.

[b)]Two different structures are possible for Type 6 bis-ns-CB[n]. For example, when x ≠ y both Type 6 bis-ns-CB[x,y] and Type 6 bis-ns-CB[y,x] are possible.

Transformation of Type 4 ns-CB[n,1] into Inverted CB[n+1].

We have previously described the isolation of inverted CB[6] (i-CB[6]) and inverted CB[7] (i-CB[7]) from reaction mixtures containing a 1:2 mixture of glycoluril:formaldehyde. One of the interesting outcomes of the mechanism depicted in Scheme 3 is that Type 4 bis-ns-CB[n,1] is converted into inverted CB[n+1] by reaction with two molecules of formaldehyde (Scheme 4). The present invention therefore also enables the preparation of additional i-CB[n] compounds as depicted in Scheme 4.

Scheme 4. Transformation of Type 4 ns-CN[n,1] to i-CB[n+1]

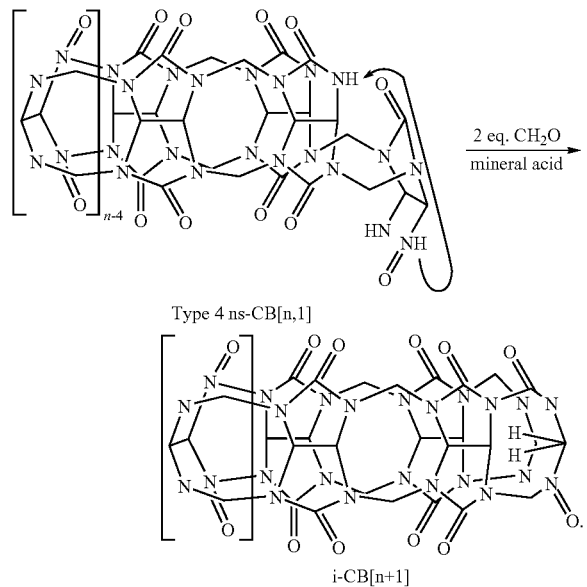

Use of Purified Oligomeric Building Blocks to Improve the Yield of Nor-Seco-CB[n] that Lack Three, Four, or More $CH_2$ Groups.

Although it is possible to bias the nor-seco-type CB[n] forming reactions toward smaller or larger oligomers and nor-seco-type CB[n] by changing the input ratio of glycoluril:formaldehyde the yields of the larger nor-seco-type CB[n] and nor-seco-type CB[n] that are missing three or more methylene bridges are modest because the idealized glycoluril:formaldehyde ratios are close to 1:2. However, these compounds, can be targeted by using a preformed oligomer as the building block. For example, as noted above, tetrakis-ns-CB[20] which lacks four $CH_2$ groups contains 20 glycoluril rings and 36 methylene groups and would therefore be favored during a CB[n] forming reaction consisting of a 1:1.8 ratio of glycoluril:formaldehyde. Alternatively, tetrakis-ns-CB[20] can be formed by the reaction of pentamer 9 with 1 equivalent of formaldehyde. Scheme 5 shows the structures of nor-seco-type CB[20] (i.e., Type 1-tetrakis-ns-CB-[20] (n=5, P=4); Type 2-tetrakis-ns-CB[20] (n=5, P=2); Type 4-tetrakis-ns-CB[20] (n-5, P=2); Type 5-tetrakis-ns-CB[20] (n=5, P=4)) and other macrocycles with a ratio of glycoluril pentamer 9:formaldehyde of 1:1 that also form in the reaction mixture. Although we specifically draw compounds composed of entirely Type 1, Type 2, Type 4 and Type 5 linkages, compounds that contain Type 3, Type 6, or Type 7 linkages are also specifically envisioned as are compounds that contain two or more different types of linkages (Type 1-Type 7) between the glycoluril oligomer building blocks. Similar reactions with different oligomeric building blocks (e.g. 6, 7, 8, 10, 11, n-mer (Scheme 2)) and 1 equivalent of formaldehyde give rise to related products.

Scheme 5. Higher nor-seco cucurbit[n]urils.

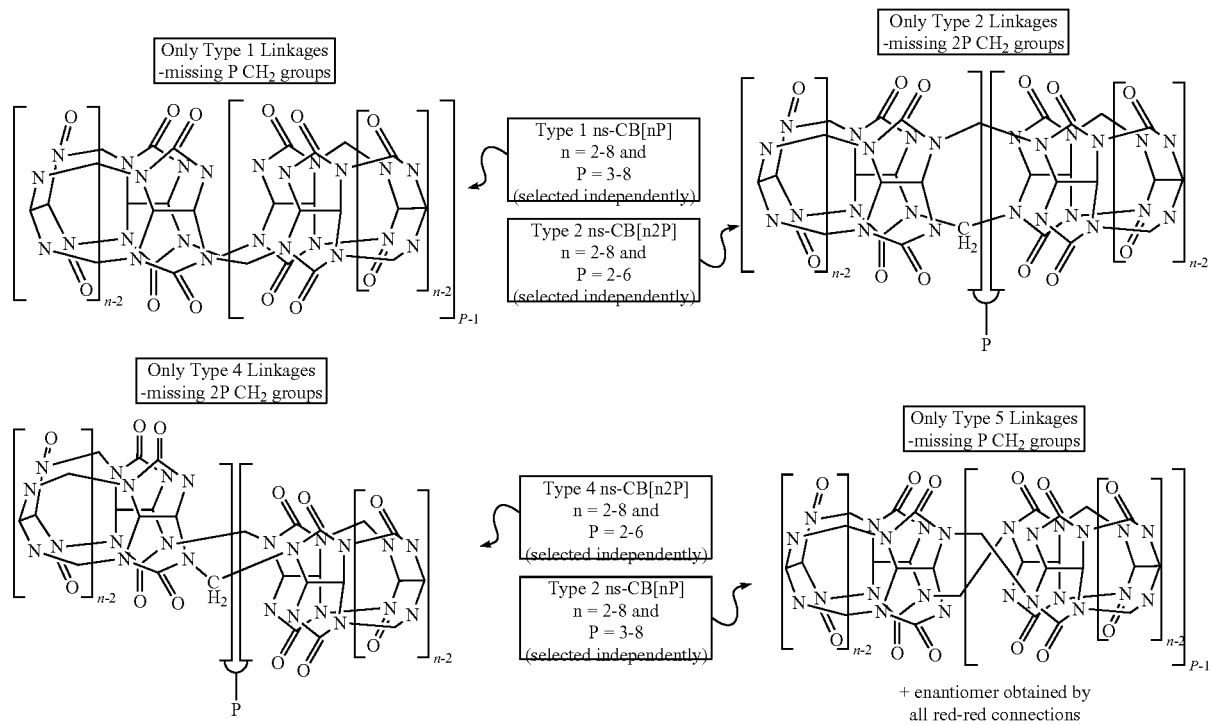

From the above description, it will readily be appreciated that many varieties of nor-seco-type CB[n] type compounds may be made. Generally, these compounds may be described by 1) type of linkage, 2) nor-seco number, i.e., number of missing $CH_2$ groups, and 3) the total number of glycoluril rings, i.e., CB[n].

In order to more clearly illustrate the type of higher nor-seco-type CB[n] compounds which are provided by the present invention, attention is directed to Scheme 6 below.

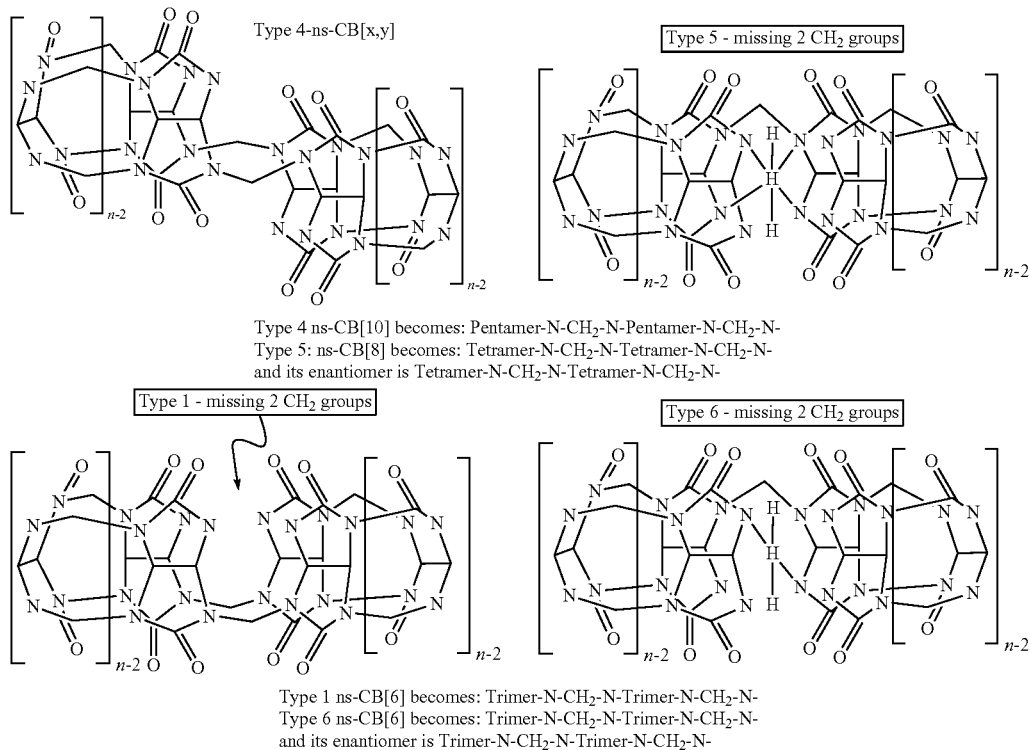

Type 4 ns-CB[10] becomes: Pentamer-N-$CH_2$-N-Pentamer-N-$CH_2$-N-
Type 5: ns-CB[8] becomes: Tetramer-N-$CH_2$-N-Tetramer-N-$CH_2$-N-
and its enantiomer is Tetramer-N-$CH_2$-N-Tetramer-N-$CH_2$-N-

Type 1 ns-CB[6] becomes: Trimer-N-$CH_2$-N-Trimer-N-$CH_2$-N-
Type 6 ns-CB[6] becomes: Trimer-N-$CH_2$-N-Trimer-N-$CH_2$-N-
and its enantiomer is Trimer-N-$CH_2$-N-Trimer-N-$CH_2$-N-

Scheme 6 above illustrates the nomenclature used in the present specification as well as exemplary types of nor-seco-type CB[n] compounds afforded by the present invention: Scheme 6 clarifies that Type 4 bis-ns-CB[10] becomes—Pentamer-N—$CH_2$—N-Pentamer-N—$CH_2$—N—.

Probe Compounds

Although p-xylylene diamine has been described in the above examples as a probe compound, it is explicitly contemplated that both N-lower alkylated and N,N-lower dialkylated derivatives of xylylene diamine may also be used as probes. As used herein, the term "lower alkyl" means $C_1$-$C_8$ alkyl, either linear or branched.

Additionally, also explicitly contemplated are the substituted R derivatives of p-xylylene diamine, i.e., with one or both amino groups bearing a R substituent (for example, guest #14), where R may be a sterically-hindered group, such as tert-butyl or triphenylmethyl, in order to reduce the rate of exchange between the probe compound and the host ns-type-CB[n] compound.

Exemplary Use:

The various uses of the nor-seco-type CB[n] compounds of the present invention encompass those of the previously known members of the CB[n] family and those of the cyclodextrin series of macrocycles. For example, any of the following uses may be noted: removal of heavy metals from waste water, sequestration of radioactive metals, removal of certain gases from air (e.g. CO, $NO_x$, $SO_x$), to deodorize animal waste, as additives to cosmetics, foods, and polymers, as carriers for pesticides, herbicides, and drugs, as sensors for amines (e.g. amino acids, peptide, proteins, alkaloids of abuse, neurotransmitters, etc.), as a slow release agent for drug formulations, as a pleasant odor releasing material, as a beverage flavor enhancer, as an additive in paints, as a component of a stationary phase for chromatographic applications, as a component of dialysis tubing, as an active component in gas masks, as an affinity agent in affinity chromatography, as a component of an ion-selective electrode, as a delivery agent for Pt based anticancer agents, as catalysts for certain organic reactions, as an additive in capillary electrophoresis, as an immobilization element for the preparation of biochips (e.g. gene-chips, protein-chips, etc.), for the preparation of liposomes that release pharmaceutical agents, as an additive in poly acrylamide gel electrophoresis, to modify by encapsulation the properties (e.g. stability, conductivity) of molecular wires, for the preparation of cucurbituril nanoparticles by aggregation phenomena that encapsulate pharmaceuticals, for the preparation of ion channels in biomembranes, as a component of a calorimetric or fluorometric chemical sensing ensemble, in the preparation of polymer films, and photostabilization of fluorescent dyes and stimuli responsive supramolecular polymers.

Additional uses for the present nor-seco-type CB[n] compounds include: phase transfer catalyst, modification of the properties of ionic liquids by complexation of the organic cation, use of bis-ns-CB [10] as a non-covalent chemical inducer of protein dimerization (CID), as a platform to bring together catalyst and substrate for various organic reactions. Perhaps most importantly, the chiral nor-seco-CB[n] compounds have the ability to interact diastereoselectively with one enantiomer in a racemic mixture which would be very important for many chemical sensing and separation, biological, and pharmaceutical applications. That is, the present nor-seco-type CB[n] compounds have the ability to sense and detect, and/or separate a single enantiomer from a racemic mixture.

The present invention also enables the preparation of CB[n] derivatives, CB[n] derivatives that contain more than one cucurbit[n]uril groups, and surface immobilized nor-seco-type CB[n] and CB[n] compounds/derivatives. These new compounds and materials enable new applications and/or improve upon previous systems. For example, Type 3 ns-CB[n] may be reacted with aldehydes (RHO) under acidic conditions to yield R—CB[n] derivatives where one of the bridging C-atoms has been substituted with an R group (Scheme 7). Similarly, Type 1 ns-CB[n] or Type 2 ns-CB[n] (not shown) can be transformed into isomers of $R_2$—CB[n]. These compounds are particularly advantageous since they place new functionality (R-group) at the entrance to the CB[n] cavity which strongly influences its recognition properties. Type 3 ns-CB[n] can also be transformed into compounds containing two or more CB[n] groups by reaction with compounds containing two or more aldehyde groups (e.g. CB[n]-R—CB[n']) where n and n' may be selected independently. Such dimeric compounds have great potential as components for nanoscale architectures (e.g. stimuli responsive supramolecular polymers), for affinity purification (e.g. two cavities gives very tight but easily reversible binding), and as transmembrane ion channels. Scheme 7 also shows the reaction of glycoluril oligomers 8-1 and n-mer with glycoluril cyclic ethers which selectively gives the disubstituted $R_2$—CB[n] and $R_2$-i-CB[n] compounds which are not easily accessible otherwise.

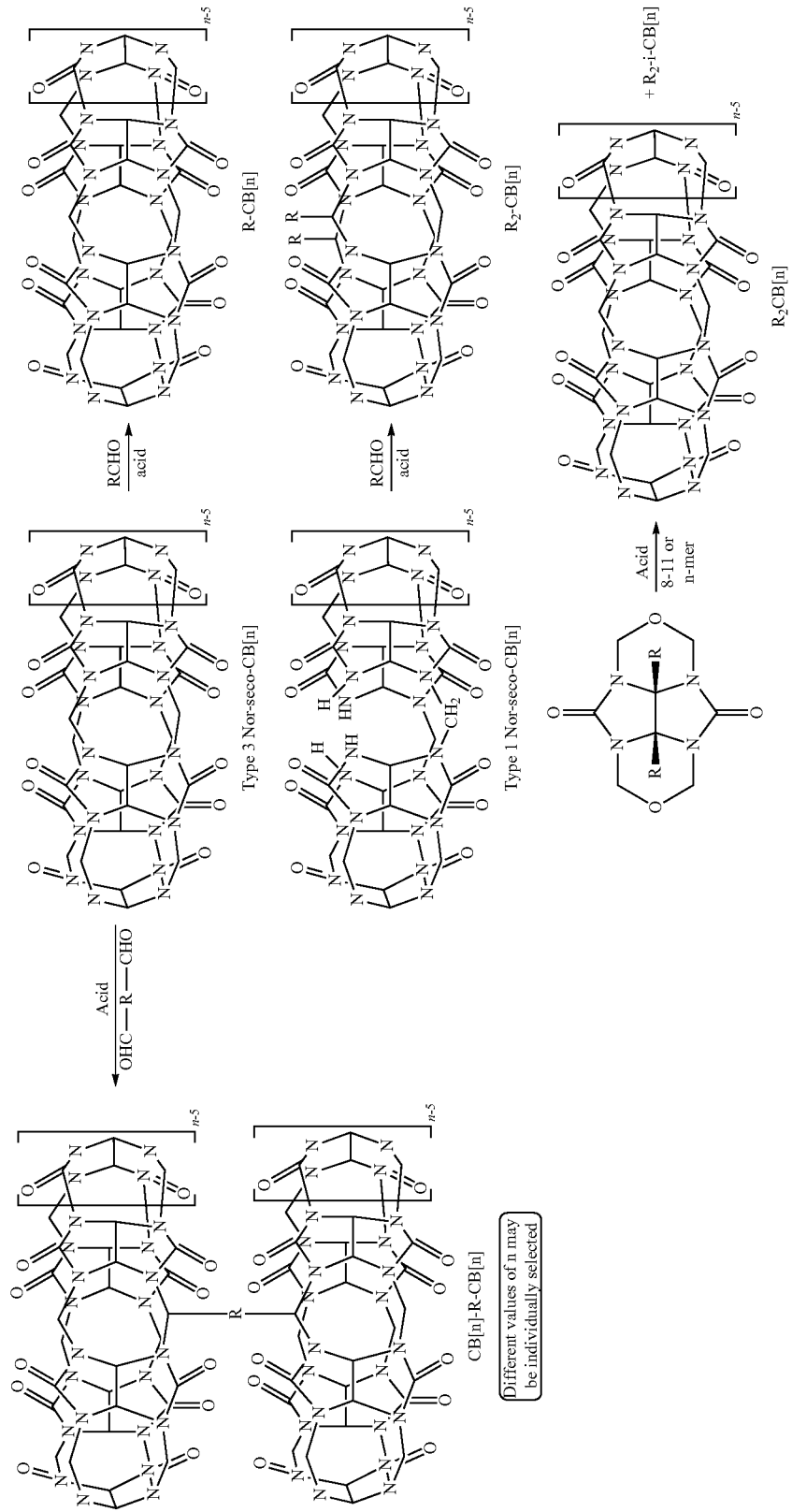

Figure 27:
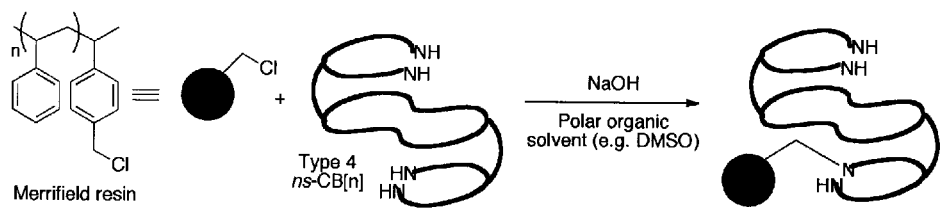
FIG. 27 depicts the immobilization of Type 4 bis-ns-CB [10] to resin beads.
Figure 28:
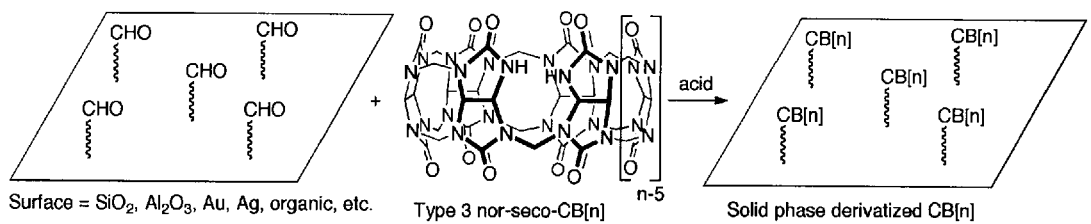
FIG. 28 depicts the reaction of Type 3 bis-ns-CB[n] with a glass slide or other surface substrate derivatized with CHO groups.
Figure 29:
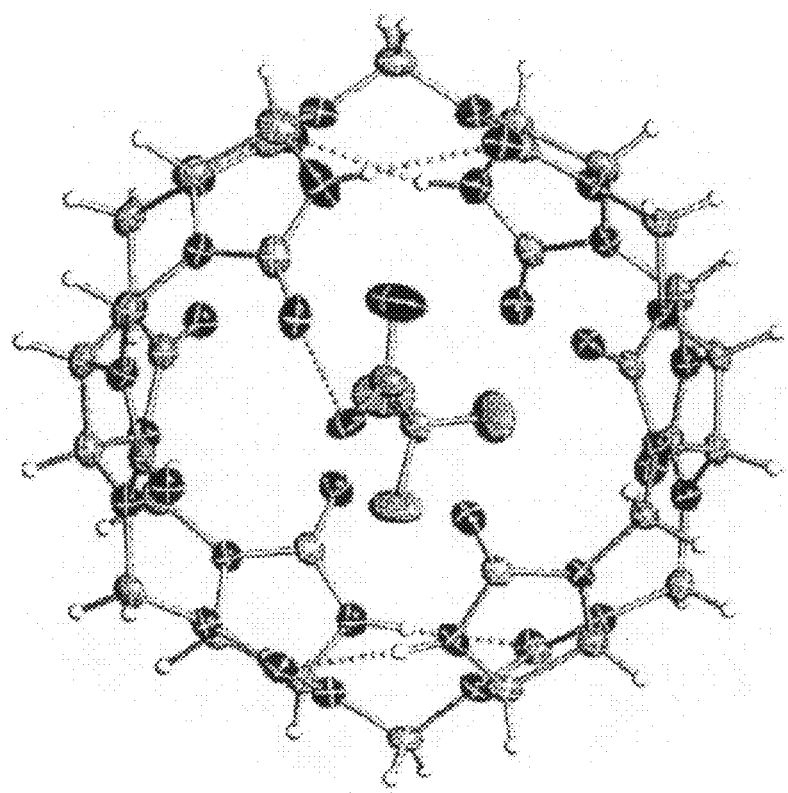
FIG. 29 illustrates the x-ray crystal structure of (±)-bis-ns-CB[6] (the trifluoroacetate). The dotted lines highlight the H-bonds between N—H and O=C groups.
Figure 30:
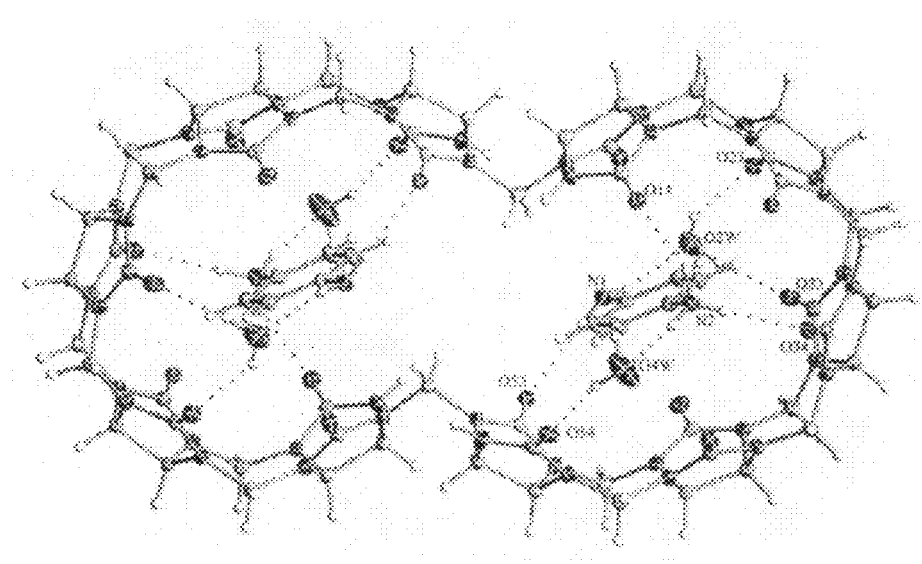
FIG. 30 illustrates the x-ray crystal structure of bis-ns-CB [10].

In addition to solution phase aldehydes, Type 1-3 nor-seco-type CB[n] may also be reacted with aldehydes bound to a solid phase or a surface. FIG. 28 depicts the reaction of Type 3 ns-CB[n] with a glass slide derivatized with CHO groups although the reaction is equally applicable for CHO groups bound to resin beads or other solid substrates. In a related manner, the free NH groups of the various nor-seco-type CB[n], particularly Type 4 bis-ns-CB[n] whose NH groups are not intramolecularly hydrogen bonded may be reacted with alkyl halides (R—X) under basic conditions. FIG. 27 depicts the immobilization of Type 4 bis-ns-CB [10] to Merrifield resin although reactive alkyl halides attached to other solid phases are equally applicable. These new immobilized CB[n] and nor-seco-type CB[n] can be used for applications including chromatographic stationary phases, bio-chips (e.g. gene-chip, protein chip), affinity column purification, and non-covalent surface immobilization chemistry for non-fouling surfaces. Advantages of using the nor-seco-type CB[n] in these applications include the chirality of certain of these macrocycles, their enhanced dissociation rates (useful for chromatography), the enhanced size of the nor-seco-type CB[n] cavity and the homogeneity of the immobilized macrocycle.

Additional Examples are provided below to merely further illustrate the present invention.

Example 5

(±)-Bis-nor-seco-CB[6] was prepared and isolated using the procedures described above.

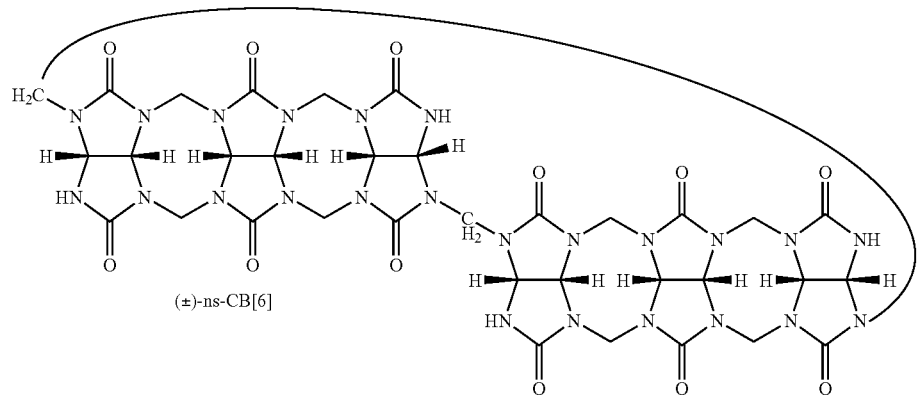

(±)-ns-CB[6]

Characterization of (±)-bis-nor-seco-CB[6]. $^1$H NMR (400 MHz, D$_2$O): 5.61 (d, J=16, 4H), 5.55 (d, J=16, 4H), 5.50-5.40 (m, 12H), 4.58 (s, 4H), 4.17 (d, J=16, 4H), 4.15 (d, J=16, 4H). MS (ES): m/z 973 (100, [M=H]$^+$). HR-MS (ES): m/z 1105.2031 ([M+Cs]$^+$), C$_{34}$H$_{36}$N$_{24}$O$_{12}$Cs, calcd. 1105.1999. X-ray crystal structure of Type 5 (±)-bis-ns-CB[6]•CF$_3$CO$_2$H.

Example 6

Enantioselective Complexation with (±)-bis-nor-seco-CB [6]. A mixture of (±)-bis-ns-CB[6] (2.0 mg) and (±)-methylbenzylamine (excess) was dissolved in D$_2$O and transferred to an NMR tube for analysis. The $^1$H NMR spectrum shows 2 sets of resonances which correspond to approximately a 66:33 ratio of the sets of diastereomers (e.g. (+)-bis-ns-CB [6]•(+) methylbenzylamine (and its enantiomer (−)-bis-ns-CB[6]•(−)-methylbenzylamine) as well as (+)-bis-ns-CB[6]•(−)-methylbenzylamine (and its enantiomer (−)bis-ns-CB[6]•(+)-methylbenzylamine)). This is the first example of an enantioselective recognition process within a chiral cucurbituril.

Example 7

(±)-bis-ns-CB [8] was prepared and isolated using the procedures described above.

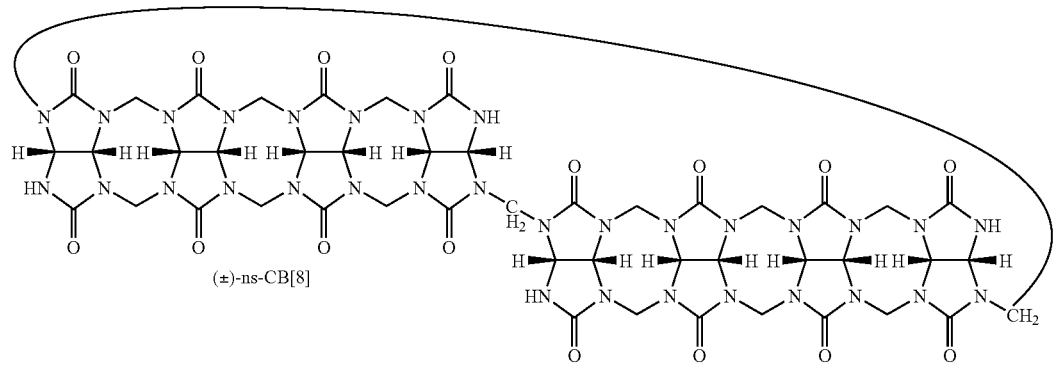

(±)-ns-CB[8]

Characterization of (±)-bis-nor-seco-CB[8]. $^1$H NMR (400 MHz, D$_2$O) for (±)-bis-ns-CB[8]•p-xylylenediamine: 6.73 (s, 4H), 5.78 (d, J=16, 2H), 5.65-5.55 (m, 6H), 5.50-5.40 (m, 4H), 5.38-5.30 (m, 6H), 5.20-5.15 (ABq, 4H), 4.61 (s, 4H), 4.42 (d, J=16, 2H), 4.13 (d, J=16, 2H), 4.03 (d, J=16, 2H), 4.03 (d, J=16, 2H), 3.97 (d, J=16, 2H), 3.93 (d, J=16, 2H), 3.80 (s, 4H).

Example 8

Achiral Type 3 ns-CB[6] was prepared and isolated using the procedures described above.

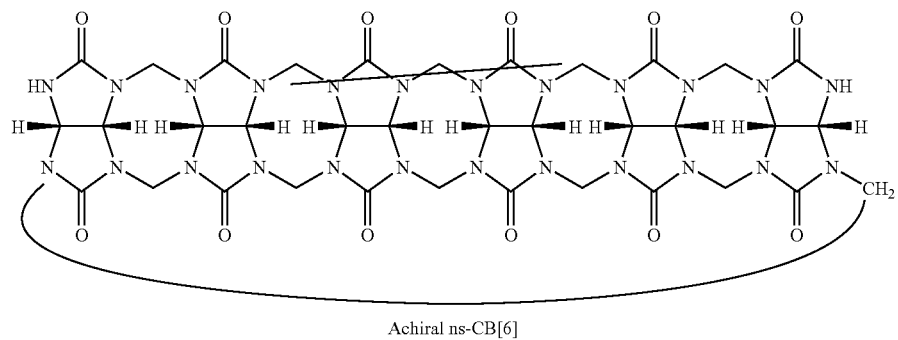

Achiral ns-CB[6]

Characterization of achiral nor-seco-CB[6]. $^1$H NMR (400 MHz, D$_2$O) for achiral ns-CB[6]•p-xylylenediamine: 6.57 (d, J=8, 2H), 6.43 (d, J=8, 4H), 5.75-5.25 (m, 23H), 4.25-4.00 (m, 13H), 3.88 (d, J=16, 2H). MS (ES): m/z 562 (100, [M•p-xylylenediammonium]$^{2+}$, m/z spacing=0.5 confirmed for molecular ion).

Example 9

A mixture of glycoluril and paraformaldehyde at 50° C., in concentrated HCl to afford a reaction mixture that contains CB[n] and nor-seco-type CB[n]. Bis-ns-CB[10] was isolated as a white solid in 15% yield by washing and recrystallization. The $^1$H NMR spectra of free bis-ns-CB[10] was not informative due to significant signal overlap although the resonance for the inwardly directly CH$_2$ bridge (H$_a$) appeared in a distinctive region of the spectrum. In contrast, the NMR spectra of bis-ns-CB[10]•guest #2$_2$ was relatively well dispersed which allowed unambiguous assignment of its structure by 2D NMR methods. Of particular diagnostic utility are the resonances for H$_a$ and H$_n$ which appear as singlets due to the overall C$_{2h}$-symmetry of bis-ns-CB[10]•guest #2$_2$.

Fortunately, we obtained single crystals of bis-ns-CB[10] as its p-phenylenediamine (guest #3) complex (bis-ns-CB[10]•guest #3$_2$) which were suitable for x-ray structure determination. Several structural features are intriguing including: 1) the absence of two CH$_2$ bridges and the internal disposition of the two single CH$_2$ bridges, 2) two symmetry equivalent cavities and their lack of vertical registration, and 3) infinite guest filled channels defined by the stacking of bis-ns-CB[10]•guest #3$_2$ in the crystal. Interesting, the solvating H$_2$O molecules in the ureidyl carbonyl region of bis-ns-CB[10]•guest #3$_2$ act as bridges between guest NH and host C=O groups.

After the structure of bis-ns-CB[10] was elucidated, we investigated its recognition properties. The two cavities of bis-ns-CB[10] are caparable in size to those of CB[6] and CB[7] and therefore bind guests commonly used with these hosts. For example, bis-ns-CB[10] forms ternary (1:2) complexes with alkyl, cycloalkyl, aryl, and adamantyl amines although some of these complexes display fast exchange on the NMR timescale. Bis-ns-CB[10] also binds some more chemically and biologically interesting species like dyes (e.g. coumarins, acridines, nile blue), amino acids (tryptophan, 4-aminophenylalanine, and arginine), and electrochemically active substances (ferrocenes and viologens). More sizable guests (e.g. guest #12 and guest #13) which are too large for the individual CB[6]-CB[7] sized cavities of bis-ns-CB[10] instead form binary (1:1) complexes that fill both cavities simultaneously.

Several types of selectivity are observed within ternary complexes of bis-ns-CB[10]. For example when unsymmetrical guest are bound within bis-ns-CB[10] three diastereomers are possible. For some guests a single diastereomer is observed (e.g. bis-ns-CB[10]•guest #7$_2$) which we tentatively assign the top-top conformation. In the top-top conformation, the NH$_3^+$ groups bind at the more flexible C=O portals which lack a CH$_2$-bridge. For other guests all three conformations can be observed by $^1$H NMR. A second type of selectivity is possible during the binding of chiral but racemic guests. For example, when a mixture of guest #14 and ent-guest #14 is offered to bis-ns-CB[10], two homochiral forms (bis-ns-CB[10]•guest #14$_2$ and bis-ns-CB[10]•ent-guest #14$_2$) and one heterochiral form (bis-ns-CB[10]•guest #14.ent-guest #14) are observed as a statistical mixture.

Example 10

X-ray Crystallography of bis-ns-CB[10] (UM#1313)

A colorless prism of [C$_{58}$H$_{60}$N$_{40}$O$_{20}$), (NH$_2$C$_6$H$_4$NH$_3$)$_2$] I$_2$•22.78H$_2$O, approximate dimensions 0.17×0.26×0.395 mm$^3$, was used for the X-ray crystallographic analysis. The X-ray intensity data was measured at 223(2) I on a three-circle diffractometer system e quipped with Bruker Smart1000 CCD area detector using a graphite monochromator and a MoKα fine-focus sealed tube (λ=0.71073 Å) operated at 50 kV and 30 mA. The detector was placed at a distance of 4.958 cm from the crystal. A total of 1493 frames were collected with a scan width of 0.3° in ω and an exposure time of 23 sec/frame using SMART (Bruker, 1999). The total data collection time was 12.50 hours. The frames were integrated with SAINT software package using a narrow-frame integration algorithm. The integration of the data using a Monoclinic unit cell yielded a total of 36913 reflections to a maximum θ angle of 27.50°, of which 11123 were independent (completeness=95.1%, R$_{int}$=2.19%, R$_{sig}$=2.05%) and 9258 were greater than 2σ(I). The final cell dimensions of α=12.3614(6) Å, α=90°, β=95.7440(10)°. Γ=90°, V=5097.7 (4) Å$^3$, are based upon the refinement of the XYZ-centroids of 8401 reflections with 2.2<θ<28.3° using SAINT. Analysis of the data showed 0.00% decay during data collection. Data were corrected for absorption effects with the Semi-empirical from equivalents method using SADABS (Sheldrick, 1996). The minimum and maximum transmission coefficients were 0.784 and 0.883. The structure was solved and refined using the SHELXS-97 (Sheldrick, 1990) and SHELXL-97 (Sheldrick, 1997) software in the space group P2$_1$/n with Z-2 for the formula unit [(C$_{58}$H$_{60}$N$_{40}$O$_{20}$)•(NH$_2$C$_6$H$_4$NH$_3$)$_2$] I$_2$•22.78H$_2$O. The final anisotropic full-matrix least-squares refinement on F$^2$ with 813 variables converged at R$_1$=4.33% for the observed data and wR$_2$=9.69% for all data. The goodness-of-fit was 1.000. The largest peak on the final difference map was 0.930ē/Å$^3$ and the largest hole was −1.048ē/Å$^3$. On the basis of the final model, the calculated density was 1.642 g/cm$^3$ and F(000), 2600ē.

Crystallographic Comments:
Data set quality: strong.
Twinning: none.
Disorder: occupational disorder of more than 50% of water of crystallization.
H-atoms refinement: in CH—H-atoms rides on C atom, in N—H and O—H only distance is restrained.
Residual density: near heavy atoms & near disordered groups.
Structure quality: very good.
Check CIF: Platon—all warning due to the disorder of water.

TABLE 2

Crystal data and structure refinement for UM #1313.

| | |
|---|---|
| X-ray labbook No. | 1313 |
| Crystal. ID | Isaacs/Huang 119 PDA KI |
| Empirical formula | C$_{70}$H$_{123.56}$I$_2$N$_{44}$O$_{42.78}$ |
| Formula weight | 2519.97 |
| Temperature | 223(2) K |
| Wavelength | 0.71073 Å |
| Crystal size | 0.395 × 0.26 × 0.17 mm$^3$ (see FIG. 3) |
| Crystal habit | colorless prism |
| Crystal system | Monoclinic |
| Space group | P2$_1$/n |
| Unit cell dimensions | a = 12.3614(6) Å   α = 90° |
| | b = 21.3847(11) Å   β = 95744(1)° |
| | c = 19.3817(10) Å   γ = 90° |
| Volume | 5097.7(4) Å$^3$ |
| Z | 2 |
| Density, ρ$_{calc}$ | 1.642 g/cm$^3$ |
| Absorption coefficient, μ | 0.730 mm$^{-1}$ |
| F(000) | 2600e |
| Diffractometer | Bruker Smart1000 CCD area detector |
| Radiation source | fine-focus sealed tube. MoK$_α$ |
| Generator power | 50 kV, 30 ma |
| Detector distance | 4.958 cm |
| Detector resolution | 8.33 pixels/mm |
| Total frames | 1493 |
| Frame size | 512 pixels |
| Frame width | 0.3° |
| Exposure per frame | 23 sec |
| Total measurement time | 12.50 hours |
| Data collection method | ω and φ scans |
| θ range for data collection | 2.11 to 27.50° |
| Index ranges | −14 ≤ h ≤ 15, |
| | −27 ≤ k ≤ 27, |
| | −23 ≤ l ≤ 24 |
| Reflections collected | 36913 |
| Independent reflections | 11123 |
| Observed reflection, 1 > 2σ(1) | 9258 |
| Coverage of independent reflections | 95.1% |
| Variation in check reflections | 0.00% |
| Absorption correction | Semi-empirical from equivalents SADABS (Sheldrick, 1996) |
| Max. and min. transmission | 0.883 and 0.784 |
| Structure solution technique | direct |
| Structure solution program | SHELXS-97 (Sheldrick, 1990) |
| Refinement technique | Full-matrix least-squares on F$^2$ |
| Refinement program | SHELXL-97 (Sheldrick, 1997) |
| Function minimized | Σw(F$_o^2$ − F$_c^2$)$^2$ |
| Data/restraints/parameters | 11123/100/813 |
| Goodness-of-fit on F$^2$ | 1.021 |
| Δ/σ$_{max}$ | 0.002 |
| Final R indices: | |
| R$_1$, I > 2σ(I) | 0.0433 |
| wR$_2$, all data | 0.0969 |
| R$_{int}$ | 0.0219 |
| R$_{sit}$ | 0.0205 |
| Weighting scheme | w = 1/[σ$^2$(F$_o^2$) + (0.02P)$^2$ + 10.02P], P = [max(F$_o^2$, 0) + 2F$_c^2$]/3 |
| Largest diff. peak and hole | 0.930 and −1.048e/Å$^3$ |

R$_1$ = Σ||F$_o$| − |F$_c$||/Σ|F$_o$|, wR2 = [Σw(F$_o^2$ − F$_c^2$)$^2$/Σw(F$_o^2$)$^2$]$^{1/2}$

Experimental Detail Section.
General.

The guests used in this study were prepared by the literature procedures or purchased from commercial suppliers and were used without further purification. Melting points were measured on a Meltemp apparatus in open capillary tubes and are uncorrected. IR spectra were recorded on a commercial spectrophotometersas as KBr pellets and are reported in cm$^{-1}$. NMR spectra were measured on spectrometers operating at 400 or 500 MHz for $^1$H and 100 or 125 MHz for $^{13}$C. Mass spectrometry was performed using a VG 707E magnetic sector instrument by fast atom bombardment (FAB)

using the indicated matrix or on a JEOL AccuTOF electrospray instrument. Computational results were obtained using Spartan 02 running on a Macintosh personal computer.

Preparation and Purification of Xylylene Diamine Derivative, Guest Compound #14.

A mixture of α,α'-dibromo-p-xylene (396 mg, 1.50 mmol), (S)-(−)-α-methylbenzylamine (550 mg, 4.50 mmol) and $K_2CO_3$ (620 mg. 4.50 mmol) in MeCN (10 mL) and $H_2O$ (0.4 mL) was stirred at room temperature for 24 h. The reaction mixture was filtered and the solvent was removed by rotary evaporation. The residue was dissolved in $CHCl_3$, washed with saturated $Na_2CO_3$ and dried over an h. $Na_2SO_4$. Flash chromatography ($SiO_2$, $CHCl_3/CH_3OH/NH_4OH$ 9:0.5:0.05) gave 14 (240 mg, 47%) as a colorless oil. The preparation of ent-guest #14 proceeds similarly. TLC ($CHCl_3/CH_3OH/NH_4OH$ 9:0.5:0.05): $R_f$ 0.26. IR (neat $cm^{-1}$): 3323 w, 3057 w, 3023 m, 2966 m, 2863 w, 2826 w, 1602 m, 1512 m, 1492 s, 1450 s, 1368 m, 1202 w, 1120 s. $^1H$ NMR (400 MHz, $CDCl_3$): 7:35-7.20 (m, 10H), 7.22 (s, 4H), 3.80 (q, J=6.6, 2H), 3.63 (d, J=13.1, 2H), 3.56 (d, J=13.1, 2H), 1.64 (br. s, 2H), 1.36 (d, J=6.6, 6H). $^{13}C$ NMR (100 MHz, $CDCl_3$): 145.9, 139.6, 128.9, 128.6, 127.4, 127.2, 57.9, 51.8, 24.9. ES-MS: m/z 345 (100, $[M+H]^+$). HR-MS (ES-MS): m/z 345:2325 ($[M+H]^+$, $C_{24}H_{29}N_2$, calcd 345.2331).

Preparatory Procedure for Dowex Ion-Exchange Chromatography.

Dowex 50WX2 resin was equilibrated with 1:1 formic acid:$H_2O$ and packed into a chromatographic column (6 cm×30 cm). The column was loaded with 18 g of the crude reaction mixture dissolved in 1:1 formic acid:water. The column was subsequently eluted with a gradient containing increasing amounts of HCl in the mobile phase (0.2 to 0.8 M). The individual fractions from the column are concentrated on the rotovap and dried under high vacuum. A small amount of the solid is dissolved in $D_2O$ containing an excess of p-xylylene diamine as probe and a 1H NMR spectrum is recorded. The 6-7 ppm region of the 1H NMR spectrum is diagnostic for each given nor-seco-type CB[n] compound. For example, the achiral nor-seco-type CB[n] compounds show pairs of doublets for the aromatic protons whereas the chiral compounds typically show a singlet for the 4 equivalent aromatic protons. In this manner, fractions enriched in a given nor-seco-type CB[n] compound are combined and can be resubmitted for further purification by Dowex chromatography, recrystallization, and/or gel permeation chromatography. Typically, the order of elution from the Dowex column is dimer (6), trimer (7), tetramer (8), Pentamer (9), Type 5-(±)-ns-CB[6], hexamer (10), Type 5-(±)-ns-CB[8], Type 3-ns-CB[6], Type 4 bis-ns-CB[10], CB[6], CB[7].

Additional Observations.

Interestingly, during our binding studies with bis-ns-CB[10] the formation of binary complexes concomitant with ternary complexes was never observed, which establishes a sizable positive homotropic allosterism in the system. To demonstrate its potential in allostery, we offered bis-ns-CB[10] guest mixtures containing two (e.g. guest compounds #2 and 11, 5 and 7, 2 and 5, or 7 and 10) different guests. When guests of quite different sizes are used allosteric control leads to a mixture of homomeric complexes (e.g. bis-ns-CB[10]•guest $\#2_2$ and bis-ns-CB[10]•guest $\#11_2$). In contrast, mixtures of similarly sized guests (e.g. 2 and 5 or 7 and 10) result in mixtures of the homomeric and heteromeric ternary complexes. These results show that binding of the first guest to bis-ns-CB[10] preorganizes the second cavity for binding of a similarly sized guest. Computational results suggest that the allosteric control is transmitted between binding sites in the putative 1:1 complex via the central $H_2C\cdots CH_2$ separation which varies systematically with the size of the guest.

Nor-seco-type CB[n] compounds exhibit a unique structural and functional topology. For example, nor-seco-type CB[n] compounds bind larger guest molecules than the corresponding CB[n] host due to the less rigid and structurally more responsive nor-seco-type ns-CB[n] cavity. Nor-seco-type CB[n] compounds also display an unusual top-center isomerism as well as a positive homotropic allostery based upon a guest size induced preorganization mechanism.

For example, as an intermediate in the formation of CB[n] with reactive NH groups, bis-ns-CB[10] affords straightforward access to CB[n] derivatives, surface immobilized CB[n], and CB[n] dimers. The isolation of bis-ns-CB[10], for example, affords insight into the mechanism of CB[n] formation and enables the formation of CB[n] hosts of even higher complexity. Thus, the present invention extends both the structural range of CB[n] that can be accessed and the applications (e.g. biomimetic allosteric systems, supramolecular polymers, and covalent multivalent CB[n] scaffolds) to which CB[n] can be applied.

As used herein, the following definitions apply.

By "strong" organic or inorganic acid is meant as an organic or inorganic acid generally having a $pK_a$ value of about 1.0 or less. For example, the following $pK_a$ values at 25° C. have been reported: HI (−7), HCl (−10), $MeSO_3H$ (−2), and trifluoroacetic acid (TFA) (0.5).

By the phrase "not precluding formation of the oligomer" for R groups is meant any substituent which does not prohibit an oligomerization of glycoluril monomer. Exemplary substituents are noted for Scheme 2, wherein each R is independently hydrogen or a substituent which may be lower alkyl, aryl, heteroaryl, alkoxy, or carboxylic acid derivatives, such as esters, amides or imides. Exemplary esters are lower alkyl esters, such as methyl- or ethyl esters. Exemplary amides are amido or lower alkyl or lower di-alkyl amido. Exemplary imides are imido or lower alkyl imido. By "lower" is meant $C_1$-$C_8$.

Additionally, as used throughout the specification, the term "nor-seco-type" CB[n] means all nor-seco-, bis-nor-seco-tris-nor-seco- and higher nor-seco-CB[n] compounds which are the subject of the present invention. This is distinguished from the term "nor-seco" CB[n] which refers to only the nor-seco CB[n] compounds per se.

Further, as used herein the term "higher nor-seco CB[n] compounds" means any or all of tetrakis-ns-CB[n], pentakis-ns-CB[n], hexakis-ns-CB[n], heptakis-ns-CB[n], octakis-ns-CB[n], nonakis-ns-CB[n] or decakis-ns-CB[n] compounds.

Finally, as used herein the term "spacer group" may be any R group that is used to link nor-seco-type CB[n] or CB[n] compounds. Exemplary spacer groups are lower alkylene, aryl, carboxyl, heteroaryl, or cycloalkyl. Examples of lower alkylene are $(—CH_2—)_3$, wherein x is an integer of 1 to 20. Examples of aryl are phenyl, biphenyl or naphthyl. Examples of heteroaryl are furyl, pyrroyl, pyridinyl, pyrimidinyl, etc. The term "organic group" may be any organic group of either a functional or non-functional nature, including the group mentioned for the spacer groups. For the glycoluril n-mers in Scheme 2, "n" may have a value of an integer up to about 20, preferably up to about 12. Thus, where "n" is 10, for example, the glycoluril decamer is indicated.

Generally, the time of reaction for the preparation of any of the nor-seco-type CB[n] compounds of the present invention is from about 5 minutes at about 120° C. to as long as 60 days at about room temperature. In general, the higher the reaction temperature used in the range of from room temperature to 120° C., the shorter the required time of reaction.

Further, in general the concentration of glycoluril or glycoluril oligomer used in the preparation of the nor-seco-type CB[n] compounds may be low, such as, for example, 1.4 g of glycoluril in 32 ml of solvent, or as high as, for example, 1.4 g of glycoluril or glycoluril oligomer is acceptable.

Additionally, it is explicitly contemplated herein to use more than one glycoluril oligomer at a time in producing nor-seco-type CB[n] compounds. For example, the use of a combination of glycoluril pentamer (compound 9 of Scheme 2) and glycoluril tetramer (compound 8 of Scheme 2) is useful to obtain ns-CB[9] for example.

Further, the glycoluril oligomers used herein are generally those having all H-atoms or substituents on the same side of the compound. These are called "C-shaped." Oligomers having 4H-atoms or substituents on opposite side may also be present. These are called "S-shaped."

Moreover, for the compounds $R_2$—CB[n], $R_2$ CB[n] and $R_2$-i-CB[n], each R is independently the same definition as for the substituents as defined above for substituents in Scheme 2 or the "spacer group" as defined above.

Finally, in addition to the templating compounds noted above, it is further disclosed herein that adamantane amine compounds may also be used advantageously as templating compounds and to precipitate n-CB[n] (exverted) and ns-type-CB[n] compounds from reaction mixtures. Of particular note, is adamantane amine, any of the various singly-lower alkyl-substituted adamantane amines and any of the various di-lower-alkyl-substituted adamantane amines. For example, 3-methyl-, or 5-methyl-, or 3,5-dimethyl adamantane amine may be mentioned.

Having described the present invention, it will now be apparent that many changes and modifications can be made to the above-described embodiments without departing from the scope of the claimed invention.

What is claimed is:

1. A nor-seco cucurbit[n]uril compound or bis-nor-seco cucurbit[n]uril compound, each of which optionally contains a guest compound therein, wherein n has a value of from 5 to 10.

2. The compound of claim 1, which is a (±) nor-seco-CB[n] compound not containing the guest compound therein.

3. The compound of claim 1, which is a (±) nor-seco CB[n] compound containing the guest compound therein.

4. The compound of claim 3, wherein the guest compound comprises a dye molecule, an amino acid, a drug or a lipid.

5. The compound of claim 3, wherein the guest compound is chiral and non-racemic.

6. The compound of claim 5, wherein the guest compound is a chiral amino acid.

7. The compound of claim 1, which is a (±)bis-nor-seco-CB[n] compound not containing the guest compound therein.

8. The compound of claim 1, which is a (±)bis-nor-seco-CB[n] compound containing the guest compound therein.

9. The compound of claim 8, wherein the guest compound comprises a dye molecule, an amino acid, a drug or a lipid.

10. The compound of claim 8, wherein the guest compound is chiral and non-racemic.

11. The compound of claim 10, wherein the guest compound is a chiral amino acid.

12. Isolated and purified enantiomers of chiral [CB]n compounds, the chiral CB[n] compounds being selected from the group consisting of chiral nor-seco-CB[n] and chiral bis-nor-seco-CB[n] compounds, wherein n is from 5 to 10.

13. The isolated and purified enantiomers of claim 12, which are enantiomers of chiral nor-seco-CB[n] compounds, wherein n is from 5 to 10.

14. The isolated and purified enantiomers of claim 12, which are enantiomers of chiral bis-nor-seco-CB[n] compounds, wherein n is from 5 to 10.

* * * * *